1

United States Patent
Kolesky et al.

(10) Patent No.: US 11,559,607 B2
(45) Date of Patent: Jan. 24, 2023

(54) LIVING DEVICES FOR REPLACEMENT OF ORGANS OR SPECIFIC ORGAN FUNCTIONS, METHODS AND USES OF THE SAME

(71) Applicant: President and Fellows of Harvard College, Cambridge, MA (US)

(72) Inventors: David B. Kolesky, Cambridge, MA (US); Kimberly A. Homan, Somerville, MA (US); Jennifer A. Lewis, Cambridge, MA (US); Yen-Chih Lin, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 50 days.

(21) Appl. No.: 16/330,974

(22) PCT Filed: Sep. 6, 2017

(86) PCT No.: PCT/US2017/050279
§ 371 (c)(1),
(2) Date: Mar. 6, 2019

(87) PCT Pub. No.: WO2018/048900
PCT Pub. Date: Mar. 15, 2018

(65) Prior Publication Data
US 2019/0224370 A1    Jul. 25, 2019

Related U.S. Application Data

(60) Provisional application No. 62/383,928, filed on Sep. 6, 2016.

(51) Int. Cl.
*A61L 27/38* (2006.01)
*A61M 1/34* (2006.01)
(Continued)

(52) U.S. Cl.
CPC ........ *A61L 27/3804* (2013.01); *A01N 1/0278* (2013.01); *A61M 1/3489* (2014.02);
(Continued)

(58) Field of Classification Search
CPC ............. A61L 27/3804; A01N 1/0278; A61M 1/3489; A61M 1/3689; A61M 2202/09;
(Continued)

(56) References Cited

U.S. PATENT DOCUMENTS 4,817,600 A    4/1989   Herms et al.
5,059,205 A   10/1991   El-Nounou et al.
(Continued)

FOREIGN PATENT DOCUMENTS

WO    WO 2000/064510       11/2000
WO    WO 2003/020104 A1    1/2003
(Continued)

OTHER PUBLICATIONS

International Search Report received in PCT Application No. PCT/US2017/050279 dated Jan. 4, 2018.
(Continued)

*Primary Examiner* — Jennifer Dieterle
*Assistant Examiner* — Rebecca Lynee Zimmerman
(74) *Attorney, Agent, or Firm* — Crowell & Moring LLP

(57) ABSTRACT

Described are devices and methods for use in connection with organ replacement or organ assist therapy in a patient.

29 Claims, 23 Drawing Sheets

(51) Int. Cl.
     *A61M 1/36*      (2006.01)
     *A01N 1/02*      (2006.01)
(52) U.S. Cl.
     CPC ....... *A61M 1/3689* (2014.02); *A61M 2202/09* (2013.01); *A61M 2205/0244* (2013.01)
(58) Field of Classification Search
     CPC .. A61M 2205/0244; A61M 2210/1082; A61M 1/3472; A61M 1/34–3496
     See application file for complete search history.

(56) References Cited

U.S. PATENT DOCUMENTS

| | | | |
|---|---|---|---|
| 5,549,674 A * | 8/1996 | Humes | C12M 25/02 623/23.65 |
| 5,741,334 A | 4/1998 | Mullon et al. | |
| 6,150,164 A * | 11/2000 | Humes | C12N 5/0697 435/400 |
| 6,561,997 B1 | 5/2003 | Weitzel et al. | |
| 6,582,955 B2 | 6/2003 | Martinez et al. | |
| 6,913,588 B2 | 7/2005 | Weitzel et al. | |
| 7,048,856 B2 | 5/2006 | Fissell, IV et al. | |
| 7,540,963 B2 | 6/2009 | Fissell, IV et al. | |
| 8,048,419 B2 | 11/2011 | Humes | |
| 2003/0118559 A1 | 6/2003 | Humes | |
| 2003/0119184 A1 | 6/2003 | Humes | |
| 2004/0024342 A1* | 2/2004 | Weitzel | A61M 1/341 435/284.1 |
| 2004/0124147 A1 | 7/2004 | Fissel, IV et al. | |
| 2006/0213836 A1 | 9/2006 | Fissel, IV et al. | |
| 2006/0286078 A1* | 12/2006 | Humes | A61M 1/36 424/93.7 |
| 2007/0269489 A1 | 11/2007 | Humes | |
| 2008/0112995 A1 | 5/2008 | Shalev | |
| 2012/0058174 A1 | 3/2012 | West et al. | |
| 2014/0074007 A1* | 3/2014 | McNeil | B01J 20/3212 604/4.01 |
| 2015/0076066 A1* | 3/2015 | Zink | A61M 1/3417 210/646 |
| 2016/0287756 A1 | 10/2016 | Lewis et al. | |
| 2018/0214614 A1* | 8/2018 | Yoo | A61K 35/44 |

FOREIGN PATENT DOCUMENTS

| | | | | |
|---|---|---|---|---|
| WO | WO 2004/024300 A1 | 3/2004 | | |
| WO | WO 2006/138537 A2 | 12/2006 | | |
| WO | WO 2007/092735 | 8/2007 | | |
| WO | WO 2015/069619 | 5/2015 | | |
| WO | WO-2015069619 A1 * | 5/2015 | ............ | B33Y 10/00 |
| WO | WO 2016/141137 A1 | 9/2016 | | |
| WO | WO 2016/179242 A1 | 11/2016 | | |
| WO | WO 2018/048900 | 3/2018 | | |

OTHER PUBLICATIONS

Written Opinion of the International Searching Authority received in PCT Application No. PCT/US2017/050279 completed Oct. 11, 2017 and dated Jan. 4, 2018.
Song et al., "The Direct Differentiation of Human iPS Cells into Kidney Podocxtes," *PLOS One*, 7(9):1-9 (2012).
Du et al., "Functional Kidney Bioengineering with Pluripotent Stem-Cell-Derived Renal Progenitor Cells and Decellularized Kidney Scaffolds," *Adv. Healthcare Mater.*, 5:2080-2091 (2016).
Ko et al., "Bioengineered transplantable porcine livers with re-endothelialized vasculature," *Biomaterials*, 40:72-79 (2015).
Yang et al. "Genome-wide inactivation of porcine endogenous retroviruses (PERVs)," *Science*, 350(6264):1101-1104 (2015).
Perkel, J. M., "Xenotransplantation makes a comeback," *Nat. Biotechnol.*, 34(1):3-4 (2016).
Freedman et al., "Modelling kidney disease with CRISPR-mutant kidney organoids derived from human pluripotent epiblast spheroids," *Nat Commun*, 6(8715):1-13 (2015).
Morizane et al., "Nephron organoids derived from human pluripotent stem cells model kidney development and injury," *Nat. Biotechnol.*, 33(11):1193-1200 (2015).
Takasato, M. et al., "Kidney organoids from human iPS cells contain multiple lineages and model human neghrogenesis," *Nature*, 526:564-568 (2015).
Xia, Y. et al., "The generation of kidney organoids by differentiation of human pluripotent cells to ureteric bud progenitor-like cells," *Nat Protoc*, 9(11):2693-2704 (2014).
Tiong, H. Y. et al., "Drug-Induced Nephrotoxicity: Clinical Impact and Preclinical in Vitro Models," *Mol. Pharmaceutics*, 11:1933-1948 (2014).
Decloedt, E. et al., "Drug-Induced Renal Injury," *CME*, 29(6):252-255 (2011).
Choudhury, D. & Ahmed, Z., "Drug-associated renal dysfunction and injury," *Nat Clin Pract Nephrol*, 2(2):80-91 (2006).
Naughton, C. A., "Drug-Induced Nephrotoxicity," *Am. Fam. Physician*, 78(6):743-750 (2008).
Redfern, W. S. et al., "Impact and prevalence of safety pharmacology-related toxicities throughout the pharmaceutical life cycle" *J Pharmacol. Toxicol. Methods* Abstracts; Poster No. 94 (2010).
Jenkinson, S. E. et al., "The limitations of renal epithelial cell line HK-2 as a model of drug transporter expression and function in the proximal tubule," *Pflugers Arch—Eur J Physiol*, 464:601-611 (2012).
DesRochers, T. M. et al., "Tissue-Engineered Kidney Disease Models," *Adv Drug Deliv Rev*, 67-80:1-32 (2014).
Jansen, J. et al., "Human proximal tubule epithelial cells cultured on hollow fibers: living membranes that actively transport organic cations," *Scientific Reports*, 5(16702):1-12 (2015).
Jansen, J. et al., "Bioengineered kidney tubules efficiently excrete uremic toxins," *Scientific Reports*, 6(26715):1-12 (2016).
Oo, Z. Y. et al., "A novel design of bioartificial kidneys with improved cell performance and haemocompatibility," *J. Cell. Mol. Med*, 17(4):497-507 (2013).
Schophuizen, C. M. S. et al., "Development of a living membrane comprising a functional human renal proximal tubule cell monolayer on polyethersulfone polymeric membrane," *Acta Biomater*, 14:22-32 (2015).
Jansen, J. et al., "Biotechnological challenges of bioartificial kidney engineering," *Biotechnol Adv*, 32:1317-1327 (2014).
Zhang, H. et al., "The impact of extracellular matrix coatings on the performance of human renal cells applied in bioartificial kidneys," *Biomaterials*, 30:2899-2911 (2009).
Zhang, H. et al., "Generation of easily accessible human kidney tubules on two-dimensional surfaces in vitro," *J. Cell. Mol. Med.*, 15(6):1287-1298 (2011).
Guimaraes-Souza, N. K. et al., "In vitro reconstitution of human kidney structures for renal cell therapy," *Nephrol. Dial. Transplant.*, 27:3082-3090 (2012).
DesRochers, T. M. et al., "Bioengineered 3D Human Kidney Tissue, a Platform for the Determination of Nephrotoxicity," *PLOS One*, 8(3):1-12 (2013).
Takasato, M. et al., "Directing human embryonic stem cell differentiation towards a renal lineage generates a self-organizing kidney," *Nat Cell Biol*, 16(1):118-126 (2014).
Takasato, M. et al., "Recreating kidney progenitors from pluripotent cells," *Pediatr. Nephrol.*, 29(4):543-552 (2014).
Jang, K.-J. et al., "Human kidney proximal tubule-on-a-chip for drug transport and nephrotoxicity assessment," *Integrative Biology*, 5(9):1089-1198 (2013).
Grabias, B. M. & Konstantopoulos, K., "Epithelial-mesenchymal transition and fibrosis are mutually exclusive responses in shear-activated proximal tubular epithelial cells," *FASEB J*, 26:4131-4141 (2012).
Little, M. H. et al., "Defining Kidney Biology to Understand Renal Disease," *Clin J Am Soc Nephrol.*, 9(4):809-811 (2014).
Kolesky, D. B., et al., "Three-dimensional bioprinting of thick vascularized tissues," *Proc. Natl. Acad. Sci. USA*, 113:3179-3184 (2016).
Kolesky, D. B. et al., "3D Bioprinting of Vascularized, Heterogeneous Cell-Laden Tissue Constructs," *Adv. Mater.*, 26:3124-3130 (2014).

(56) References Cited

OTHER PUBLICATIONS

Bensamoun, S. F. et al., "Stiffness imaging of the kidney and adjacent abdominal tissues measured simultaneously using magnetic resonance elastography," *Clin. Imaging*, 35:284-287 (2011).

Furness, P. N., "Extracellular matrix and the kidney," *J Clin. Pathol.*, 49:355-359 (1996).

Wu, W. et al., "Omnidirectional printing of 3D Microvascular Networks," *Adv. Mater.*, XX, 1-6 (2011).

Wieser, M. et al., "hTERT alone immortalizes epithelial cells of renal proximal tubules without changing their functional characteristics," *Am J Physiol Renal Physiol*, 295:F1365-1375 (2008).

Adler, M. et al., "A Quantitative Approach to Screen for Nephrotoxic Compounds In Vitro," *J Am Soc Nephrol.*, 27(4):1015-1028 (2016); Published online 2015.

Pearson, A. L. et al., Albumin induces interleukin-6 release from primary human proximal tubule epithelial cells, *J. Nephrol.*, 21:887-893 (2008).

Hara-Chikuma, M. et al., "Aquaporin-I Facilitates Epithelial Cell Migration in Kidney Proximal Tubule," *J. Am. Soc. Nephrol.*, 17:39-45 (2006).

Price, G. et al., "Methods for Forming Human Microvascular Tubes In Vitro and Measuring Their Macromolecular Permeability," *Biological Microarrays: Methods and Protocols, Methods in Molecular Biolog*, 671(17): 281-293 (2011).

Cui, S. et al., "Megalin/gp330 mediates uptake of albumin in renal proximal tubule," *Am. J. Physiol.*, 271(4):F900-F907 (1996).

Gekle, M., "Renal Proximal Tubular Albumin Reabsorption: Daily Prevention of Albuminuria," *News Physiol. Sci.*, 13:5-11 (1998).

Norden, A.G.W. et al., "Urinary Megalin Deficiency Implicates Abnormal Tubular Endocytic Function in Fanconi Syndrome," *J Am. Soc. Nephrol.*, 13:125-133 (2002).

Miller, J. S. et al., "Rapid casting of patterned vascular networks for perfusable engineered three-dimensional tissues," (including supplementary information) *Nature Materials*, 11:1-13 (2012).

Wang, Y. et al., "CIC-5: role in endocytosis in the proximal tubule," *Am. J. Physiol Renal Physiol*, 289:F850-F862 (2005).

Miller, K. et al., *Prentice Hall Biology*, 38:985-989 (2008).

Mescher, A., "Junqueira's Basic Histology Text & Atlas," Reference Textbook, 13th Edition, Title Page, Table of Contents, McGraw-Hill Education (2013).

Musah et al., "Mature induced-pluripotent-stem-cell-derived human podocytes reconstitute kidney glomerular-capillary-wall function on a chip," *Nat Biomed Eng*, 1-25 (2017).

Johnson, R. et al., "Renal Physiology," *Comprehensive Clinical Nephrology E-Book*, Title Page, Table of Contents, Elsevier Health Sciences, 2:14-27 (2014).

International Preliminary Report in Patentability for PCT/US2017/050279 dated Mar. 12, 2019 including Written Opinion dated Jan. 4, 2018.

Extended European Search Report dated Mar. 30, 2020 issued in European Application No. 17849454.8.

Little, M.H., "Generating kidney tissue from pluripotent stem cells," *Cell Death Discovery*, 2, 16053, 4 pages (2016).

* cited by examiner

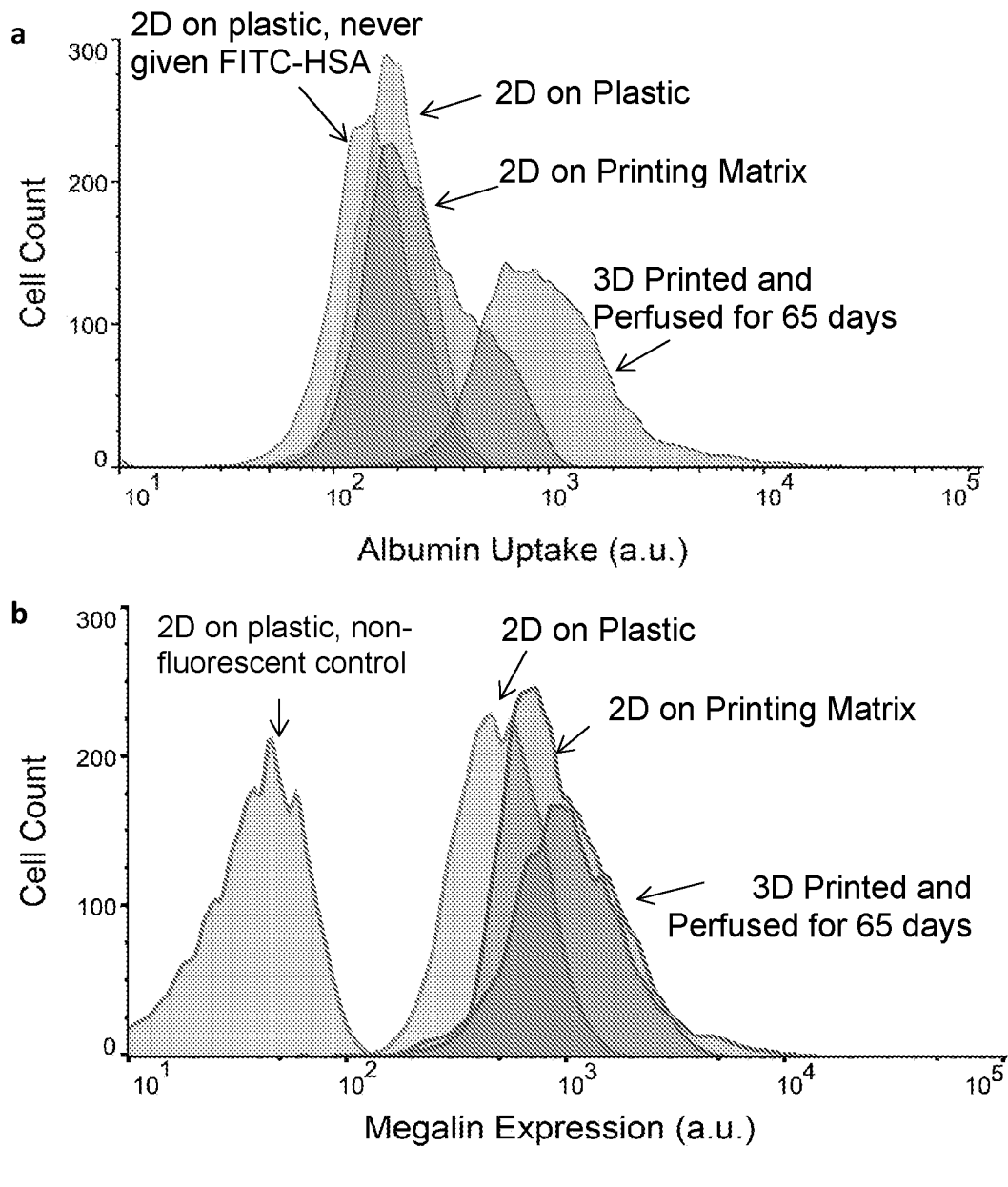
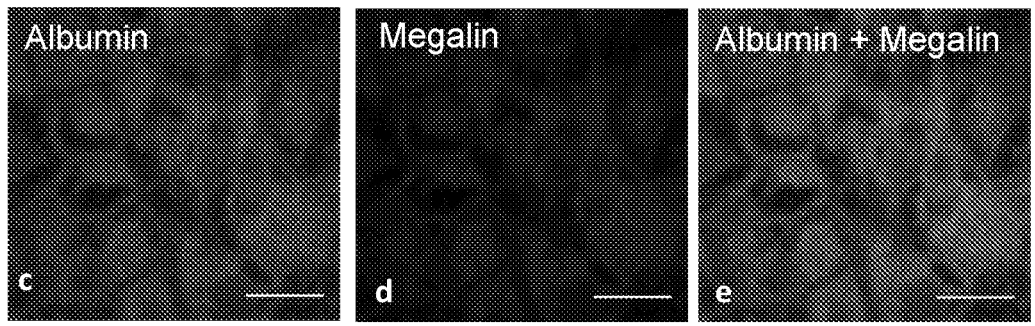
Figure 6

LIVING DEVICES FOR REPLACEMENT OF ORGANS OR SPECIFIC ORGAN FUNCTIONS, METHODS AND USES OF THE SAME

RELATED APPLICATIONS

The present patent document is a § 371 filing based on PCT Application Serial No. PCT/US2017/050279, filed Sep. 6, 2017, which claims the benefit of the filing date under 35 U.S.C. § 119(e) of Provisional U.S. Patent Application Ser. No. 62/383,928, filed Sep. 6, 2016, which is hereby incorporated by reference.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

FEDERALLY SPONSORED RESEARCH OR DEVELOPMENT

This invention was made with Government support under Grant No. CMMI-1548261, awarded by the National Science Foundation (NSF). The Government has certain rights in this invention.

BACKGROUND

1. Technical Field

Devices for replacement of organs or specific organ functions, methods or making and using of the same are described herein.

2. Background Information

Currently, the only curative solution for end stage organ failure in most cases is a transplant from a living human donor. The pool of available donors has remained constant in the last few decades while demand steadily rises. Several solutions to the organ donor shortage are being investigated, such as decellularizing deceased donor organs and recellularizing them with patient-specific cells (Du, C. et al. Functional Kidney Bioengineering with Pluripotent Stem-Cell-Derived Renal Progenitor Cells and Decellularized Kidney Scaffolds. *Advanced healthcare materials*, doi:10.1002/adhm.201600120 (2016); and Ko, I. K. et al. Bioengineered transplantable porcine livers with re-endothelialized vasculature. *Biomaterials* 40, 72-79, doi:10.1016/j.biomaterials.2014.11.027 (2015)). Also, growing organs for xenotransplantation has made a resurgence (Yang, L. et al. Genome-wide inactivation of porcine endogenous retroviruses (PERVs). Science 350, 1101-1104, doi:10.1126/science.aad1191 (2015); and Perkel, J. M. Xenotransplantation makes a comeback. *Nat. Biotechnol.* 34, 3-4, doi:10.1038/nbt0116-3 (2016)). Lastly, small organoids differentiated in vitro (Freedman, B. S. et al. Modelling kidney disease with CRISPR-mutant kidney organoids derived from human pluripotent epiblast spheroids. *Nat Commun* 6, 8715, doi: 10.1038/ncomms9715 (2015); Morizane, R. et al. Nephron organoids derived from human pluripotent stem cells model kidney development and injury. *Nat. Biotechnol.* 33, 1193-1200, doi:10.1038/nbt.3392 (2015); Takasato, M. et al. Kidney organoids from human iPS cells contain multiple lineages and model human nephrogenesis. *Nature* 526, 564-568, doi:10.1038/nature15695 (2015); and Xia, Y. et al. The generation of kidney organoids by differentiation of human pluripotent cells to ureteric bud progenitor-like cells. *Nat Protoc* 9, 2693-2704, doi:10.1038/nprot.2014.182 (2014)) are a promising start for replicating cellular heterogeneity of organs, but they are limited in size, structurally disorganized, and cannot be perfused with blood using current technologies.

Therapeutics have evolved from small molecules, to nucleic acids, to proteins, to cell-based, yet tissue-based therapeutics remains limited to thin tissues such as skin or hollow structures such as the bladder. Solid organ (e.g., heart, kidney, liver, lungs, or brain) tissue replacement remains allusive due to the cellular heterogeneity, lack of perfusable vasculature, patient-specific cell sources and suitable fabrication methodologies.

Further, a practical challenge of using tissues as therapeutic agents lies in the difficulties with interfacing fluids (blood, urine, etc.) of the human body with manufactured tissues, necessitating novel fluid handling devices and designs.

For example, U.S. Pat. No. 8,048,419 to Humes describes extracorporeal cell-based therapeutic devices and delivery systems, which provide a method for therapeutic delivery of biologically active molecules produced by living cells. However, the devices described by this and other Humes patents and applications are limited by their structure, cell-type, most importantly, their function.

As such, there is need for alternative solutions to organ transplant and organ assist.

SUMMARY

Described is an apparatus capable of housing a living perfused tissue construct that can condition the blood and act as a full or partial organ replacement as well as methods of creating the same. The living tissue construct housed in the apparatus can be implanted in vivo and act as a full or partial organ replacement in mammalian patients (human, dog, cat, etc.). This solution to organ transplant does not rely on living human donors or animals to supplant or replace organ function.

Certain embodiments relate to an apparatus for use in connection with organ replacement or organ assist therapy in a patient, comprising: (a) a housing defining an interior cavity; (b) a programmable mammalian tissue construct comprising viable cells disposed in the housing, the tissue construct adapted for and capable of at least one of the following when in use: organ-like function selected from one or more of filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; or production, secretion, and transfer of at least one of the same or another essential component or cell product into the patient's bodily fluid; and (c) a patient interface device for communication of fluids between the patient and the tissue construct disposed in the housing. The tissue construct comprises one or more tissue patterns, each tissue pattern comprising a plurality of viable cells of one or more predetermined cell types; a network of channels interpenetrating the one or more tissue patterns, said interpenetrating channels being 3D-printed with the tissue pattern; and, optionally, an extracellular matrix composition at least partially surrounding the one or more tissue patterns and the network of vascular channels. The viable cells of one or more cell types may be patient-derived cells. The viable cells may comprise at least one of renal proximal tubule cells, loop of Henle cells, renal distal tubule cells, collecting duct cells, mesangial cells, renal microvascular cells, renal cell progenitors, pluri or multipotent stem cells, other endothelial lineage cells, endothelial cells, fenestrated glomerular endothelial cells, or iPSCs-derived patient-specific cell lines. The tissue construct may be selected from the group consisting of viable cells, organoids, embryoid bodies, endothelial sprouts, autologous tissue, allogeneic tissue, xenogeneic tissue, and a three-dimensional-printed tissue constructs. The tissue construct may comprise embedded vasculature. The tissue construct may be a tubular tissue construct with embedded vasculature. The tubular tissue construct may be a nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph. The tubular tissue construct may be a human proximal tubule with embedded vasculature. The tissue construct may be an epithelial tissue construct. The tissue construct may comprise a tissue construct having an interpenetrating vascular network integrated with a cellular glomerular filtration unit and a patient interface device. The cellular glomerular filtration unit may comprise iPSC-derived intermediate mesoderm cells. The cellular glomerular filtration unit may comprise iPSC-derived podocytes. The tissue construct may comprise perfusable renal tissues with a nephron-like functionality. The patient interface may comprise an extracorporeal circuit, the housing being coupled with the extracorporeal circuit. The extracorporeal circuit may comprises a first tube configured for communication with an organ of the patient and allowing the flow of patient's bodily fluid from the patient's organ through the first tube to the tissue construct; and a second tube configured for communication with a blood vessel or a bioduct of the patient and allowing the flow of patient's bodily fluids from the tissue construct through the second tube to the patient. The apparatus may comprise a porous barrier between the tissue construct and the bodily fluid present when in use. The porous barrier may be a filter that produces an ultrafiltrate. The porous barrier may be a hemofilter. The porous barrier may be a cellular filter. The apparatus may be adapted to remove the immunogens from the bodily fluids before returning a filtrate to the patient's bodily fluids. The apparatus may further comprise at least one pump to simulate patient's blood pressure and flow rates. The apparatus may be configured so that the tissue construct can be exposed to one or more biological agents, a biological agent gradient, a pressure, and/or an oxygen tension gradient. The housing may be configured and dimensioned to be carried or worn by the patient. The apparatus may be configured to be implanted into the patient's body. The patient interface may comprise an inlet manifold on an inlet side of the housing for distributing the bodily fluid to a plurality of inlet ports of the network of interpenetrating channels and an outlet manifold on the outlet side of the housing for collecting the bodily fluid from a plurality of outlet ports of the network of interpenetrating channels. The network of interpenetrating channels may comprise a first channel for communication of arterial blood supply to the tissue construct, a second channel for communication of venous blood away from the tissue construct and a third channel for communication of material extracted by the tissue construct from the arterial blood supply. The outlet manifold may comprise at least three sections, a first section coupled with the first channel of the network of interpenetrating channels, a second section coupled with the second channel of the network of interpenetrating channels, and a third section coupled with the third channel of the network of interpenetrating channels. The tissue construct may be at least partially surrounded by a biocompatible material, wherein the biocompatible material may be in a form of a liquid, gel, paste, or a matrix. The biocompatible material may be an extracellular matrix material. The biocompatible material may comprise one or more of gelatin, fibrin, matrigel, collagen, elastin, alginate, PEG hydrogels, hyaluronic acid, and gelatin methacrylate.

Certain further embodiments relate to an apparatus for use in connection with renal replacement or assist therapy in a patient in need of renal therapy or assist comprising: (a) a housing defining an interior space; (b) a programmable mammalian tissue construct disposed in the housing, the tissue construct comprising: a plurality of proximal epithelial tubules, a plurality of endothelial tubules, a plurality of viable cells, and a biocompatible material; wherein the epithelial tubules and endothelial tubules are in a close proximity to each other, and at least partially surrounded by the extracellular matrix material; the proximal epithelial tubules are adapted for and capable of resorption of at least one essential component of the patient's bodily fluid excreted due to a disease or dysfunction of the patient's kidney, and transfer of the resorbed at least one essential component or cell product back to the patient's bodily fluid; and the proximal epithelial tubules and the endothelial tubules are capable of production, secretion, and transfer of at least one of the same or another essential component or cell product into the patient's bodily fluid; and (c) a patient interface for communication of fluid between the patient and the tissue construct disposed in the housing. The tissue construct may further comprise a plurality of capillaries of glomerulus. The plurality of capillaries of glomerulus may be integrated with the programmable tissue construct and forms a cellular filter. The biocompatible material may be in a form of a liquid, gel, paste, or a matrix. The biocompatible material may be an extracellular matrix material. The biocompatible material may comprise one or more of gelatin, fibrin, matrigel, collagen, elastin, alginate, PEG hydrogels, cellulose, glycosaminoglycan, proteoglycans, hyaluronic acid, and gelatin methacrylate. The viable cells may comprise at least one of renal proximal tubule cells, loop of Henle cells, renal distal tubule cells, collecting duct cells, mesangial cells, renal microvascular cells, renal cell progenitors, pluri or multipotent stem cells, other endothelial lineage cells, endothelial cells, fenestrated glomerular endothelial cells, or iPSCs-derived patent-specific cell lines.

Certain further embodiments relate to a method for treating a patient with a Fanconi's Syndrome comprising treating the patient with the apparatus described herein.

Yet further embodiments relate to a method for the extracorporeal extraction of toxic material from mammalian body fluids in connection with diagnosis or treatment of a mammalian condition or disease in the patient, wherein the toxic material is completely or partially cleared from the blood circulation by passing the mammalian blood or plasma through the apparatus described herein.

Additional embodiments relate to a method of treating a patient in need of organ replacement or organ assist, comprising: (a) providing the apparatus of any of claims 1 to 39 having an extracorporeal circuit adapted for bodily fluid exchange between the patient and the apparatus; (b) passing bodily fluid withdrawn from the patient through the apparatus; and (c) reinserting the withdrawn bodily fluid as a re-conditioned bodily fluid back into the patient's body; thereby treating the patient in need of organ replacement or organ assist.

Certain further embodiments relate to a method of treating a patient in need of organ replacement or organ assist, comprising: (a) implanting into the patient the apparatus of any of claims 1 to 36 adapted for bodily fluid exchange between the patient and the apparatus; (b) passing bodily fluid from the patient through the apparatus; and (c) returning to the patient the passed bodily fluid as a re-conditioned bodily fluid; thereby treating the patient in need of organ replacement or organ assist.

Yet further embodiments relate to a method of making an apparatus for use in connection with organ replacement or organ assist therapy in a patient comprising: (a) providing a housing defining an interior cavity; (b) disposing a programmable, living mammalian tissue construct comprising a plurality of viable cells into the housing; wherein the tissue construct is adapted for and capable of at least one of the following when in use: organ-like function selected from one or more of filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; or production, secretion, and transfer of at least one of the same or another essential component or cell product into the patient's bodily fluid; and (c) providing a patient interface for communication of fluids between the patient and the tissue construct disposed in the housing. The programmable, living mammalian tissue construct may be disposed into the housing by printing the programmable, living mammalian tissue construct with embedded vasculature or by molding the channels. The printing comprises: (a) depositing one or more cell-laden filaments each comprising a plurality of viable cells to form one or more tissue patterns, each of the tissue patterns comprising one or more predetermined cell types; (b) depositing one or more sacrificial filaments to form a vascular pattern interpenetrating the one or more tissue patterns, each of the sacrificial filaments comprising a fugitive ink; (c) optionally, at least partially surrounding the one or more tissue patterns and the vascular pattern with an extracellular matrix composition, (d) removing the fugitive ink to create vascular channels in the extracellular matrix composition, thereby forming a tissue construct having an interpenetrating vascular network. The method may further comprise: (e) depositing a layer of a macroporous material to form a base layer; (f) 3D printing tubular, multi-layered structures having a fugitive core onto the base layer; (g) casting additional macroporous material around the 3D printed, hollow, tubular multi-layered structures; (h) cross-linking the macroporous material; (i) removing the fugitive core to create hollow, tubular multi-layered structures; (j) seeding an iPSC-derived intermediate mesoderm cells in the 3D printed, hollow, tubular multi-layered structures; (k) differentiating the iPSCs into podocytes within the 3D printed, hollow, tubular multi-layered structures to create a podocyte layer; thereby creating a cellular glomerular filtration unit. The method may further comprise a step of integrating the tissue construct having interpenetrating vascular network and the cellular glomerular filtration unit and a patient interface device. In the method, the depositing steps may be onto a substrate. The plurality of viable cells may be patient-derived cells or from allogenic sources. The plurality of viable cells may be engineered iPSCs. The plurality of viable cells may comprise at least one of renal proximal tubule cells, loop of Henle cells, renal distal tubule cells, collecting duct cells, mesangial cells, renal microvascular cells, renal cell progenitors, pluri or multipotent stem cells, other endothelial lineage cells, endothelial cells, fenestrated glomerular endothelial cells, or iPSCs-derived patent-specific cell lines. The tissue construct may be selected from the group consisting of viable cells, organoids, embryoid bodies, endothelial sprouts, autologous tissue, allogeneic tissue, xenogeneic tissue and a tree-dimensional-printed tissue constructs. The tissue construct may comprise embedded vasculature. The tissue construct may be a tubular tissue construct having embedded vasculature integrated with a cellular glomerular filtration unit and unit and a patient interface device. The tissue construct may be a nephron, intestine, milk duct, sweat gland, colon, esophagus, stomach, eustachian tube, airway epithelium, epididymis, semi-niferous tubules, urethra, liver bile duct, pancreatic duct, common bile duct, cerebro-spinal ventricles and aquaducts, parotid glands, oral mucosa, fallopian tube, vas deferens, or lymph.

Certain other embodiments relate to a method of making an apparatus configured to be implanted into a patient's body for use in connection with organ replacement or organ assist therapy in the patient comprising: (a) providing a housing defining an interior cavity; (b) disposing a programmable mammalian tissue construct comprising a plurality of viable cells into the housing; wherein the tissue construct is adapted for and capable of at least one of the following when in use: organ-like function selected from one or more of filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; or production, secretion, and transfer of at least one of the same or another essential component or cell product into the patient's bodily fluid; (c) providing a patient interface for communication of fluids between the patient and the tissue construct disposed in the housing once the apparatus is implanted into the patient's body. The tissue construct may be created in vitro prior to disposing into the housing. The tissue construct may be allowed to mature in vitro prior to disposing into the housing.

BRIEF DESCRIPTION OF THE DRAWINGS

The patent or application file contains at least one drawing executed in color. Copies of this patent or patent application publication with color drawings will be provided by the Office upon request and payment of the necessary fee.

the white dotted line denotes the location of the cross-sectional view shown below in which PTEC cells circumscribe the open lumens in 3D, scale bar=500 μm, (E) higher magnification view of the region in (d) denoted by the white rectangle, scale bar=200 μm, (F) a 3D rendering of the convoluted renal proximal tubule where an open lumen circumscribed with an epithelial lining is directionally perfused on chip and Na/K ATPase is stained in red, acetylated tubulin is orange highlighting the primary cilia, and nuclei are blue, scale bar=50 μm.

Figure 4:
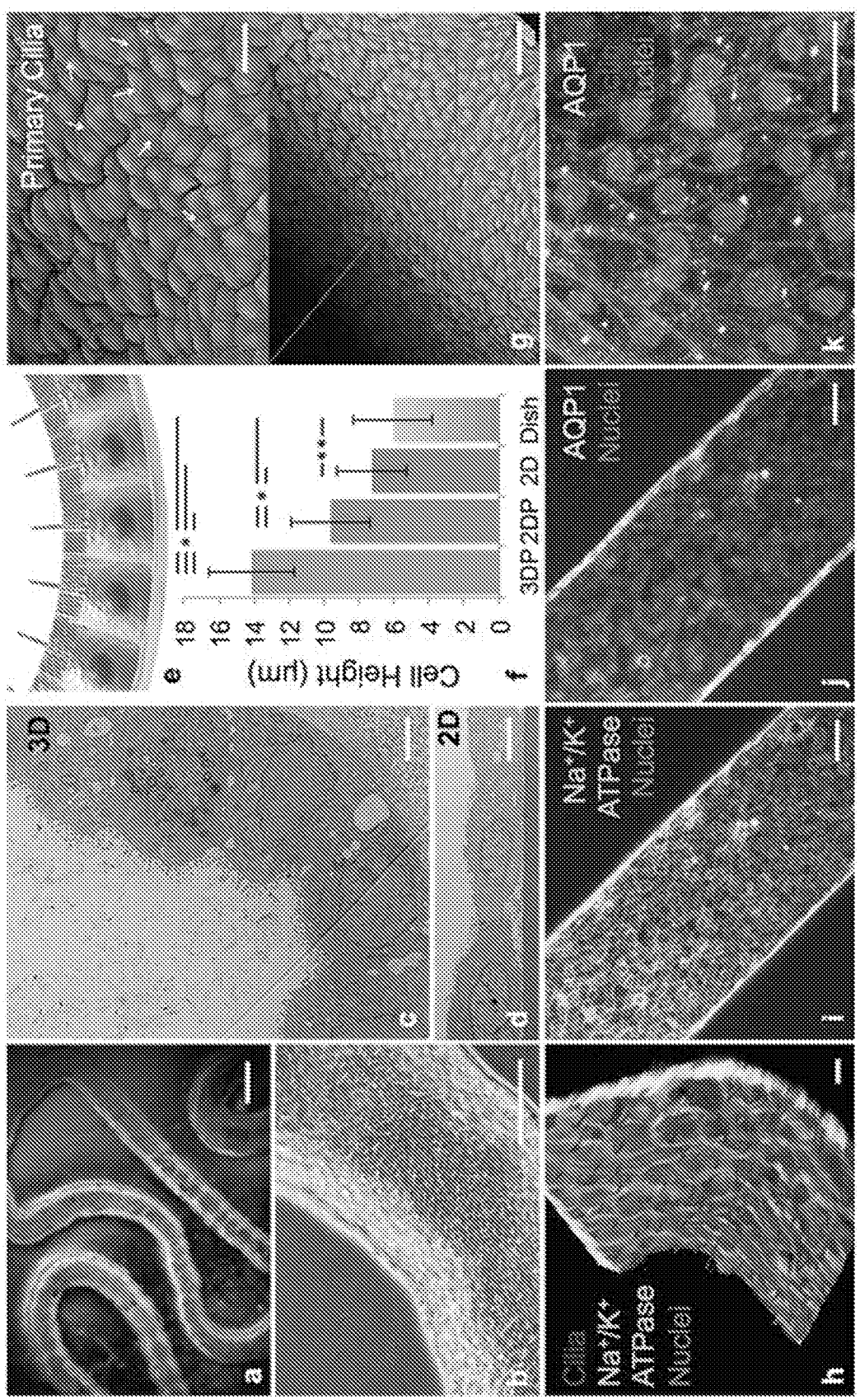

FIG. 4 depicts: (A) A phase contrast image of a mature 3D PT construct taken at 6 weeks, scale bar=500 μm, (B) phase contrast image of the 3D PT construct at 6 weeks, scale bar=250 μm, (C) TEM image of the PTECs within the tubule at 5 weeks, scale bar=5 μm, (D) TEM image of the PTECs grown on a 2D dish coated with ECM with no perfusion, scale bar=5 μm, (E) schematic view of the columnar epithelium seen in native tissue, in which PTECs pack together closely and exhibit a dense brush border on the apical side, tight junctions, and a solid basement membrane, (F) PTEC cell height as measured from TEM images of the 3D PT constructs (3DP) as well as three 2D controls (2DP=PTECs on ECM in 2D with perfusion, 2D=PTECs on ECM in 2D not perfused, Dish=bare tissue culture dish not perfused), *p<0.001, **p<0.02, (G) SEM images at low (scale bar=50 μm) and higher (scale bar=20 μm) magnifications showing a confluent layer of PTECs within the 3D PT, white arrows highlight the presence of primary cilia at a density of one per cell, (H) 3D rendering of a partial tubule showing the apical side, which highlights the primary cilia (red), scale bar=20 μm, (I) image of the PT highlighting the presence of Na/K ATPase in green, scale bar=100 μm, (J) image of the 3D PT highlighting the presence of AQP1 in yellow, scale bar=100 μm, (K) high magnification view of the image in (K) highlighting actin in red and showing AQP1 in yellow, scale bar=20 μm.

Figure 5:
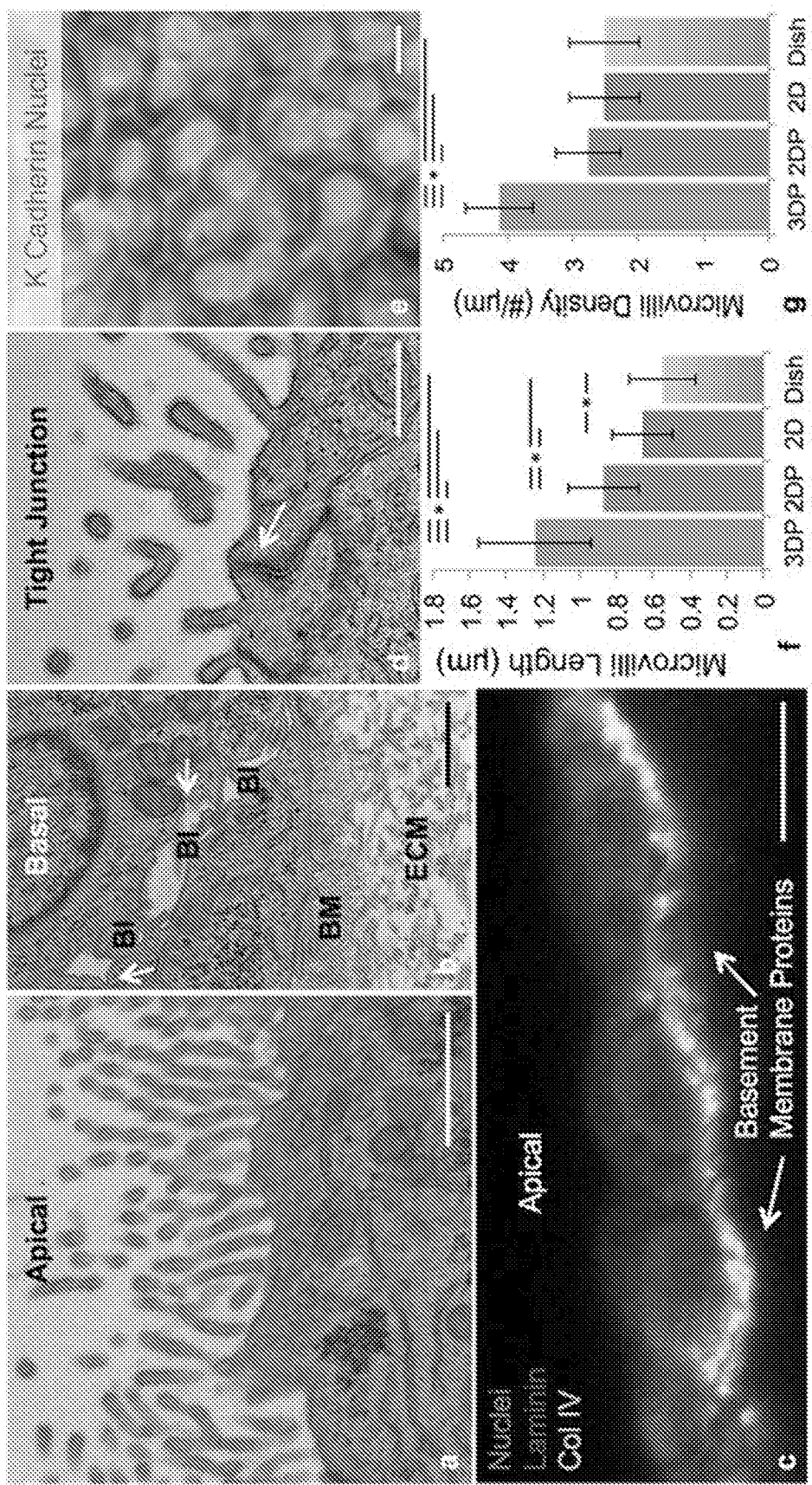

FIG. 5 depicts: (A) TEM image of the brush border on the apical side of PTECs at 6 weeks, scale bar=1 μm, (B) TEM image of the basal side of PTECs at 6 weeks highlighting the presence of the engineered extracellular matrix (ECM), basement membrane proteins secreted by the cells (BM), basolateral interdigitations (BI), and circular invaginations in the membrane marked with white arrows, scale bar=1 μm, (C) PTECs at 6 weeks showing the basement membrane proteins the cells secreted, namely laminin (predominant protein in red) and collagen IV (green), scale bar=10 μm, (D) tight junction (white arrow) between PTECs in the bioprinted tubule, scale bar=500 nm, (E) the cell junction protein K Cadherin (magenta) stained in the PT, scale bar=10 μm, (F) microvilli length and (G) microvilli density quantified through TEM images of the 3D PT constructs (3DP) as well as three 2D controls (2DP=PTECs on ECM in 2D with perfusion, 2D=PTECs on ECM in 2D without perfusion, Dish=bare tissue culture dish without perfusion), p<0.001.

FIG. 6 depicts: (A) Albumin uptake assay in 3D proximal tubules. Flow cytometry data comparing the fluorescence intensity of PTECs fed FITC-labeled human serum albumin for 2 h under several conditions, including 2D controls on bare (blue) and ECM-coated (green) plastic dishes and in 3D PTs perfused for 65 days (magenta). (B) Flow cytometry data comparing the fluorescence intensity of megalin for the same PTEC samples as shown in (A,C) fluorescence image of the 3D PT constructs stained for FITC-labeled albumin (red), (D) megalin (blue), and (E) combined, scale bars=20 μm.

Figure 7:
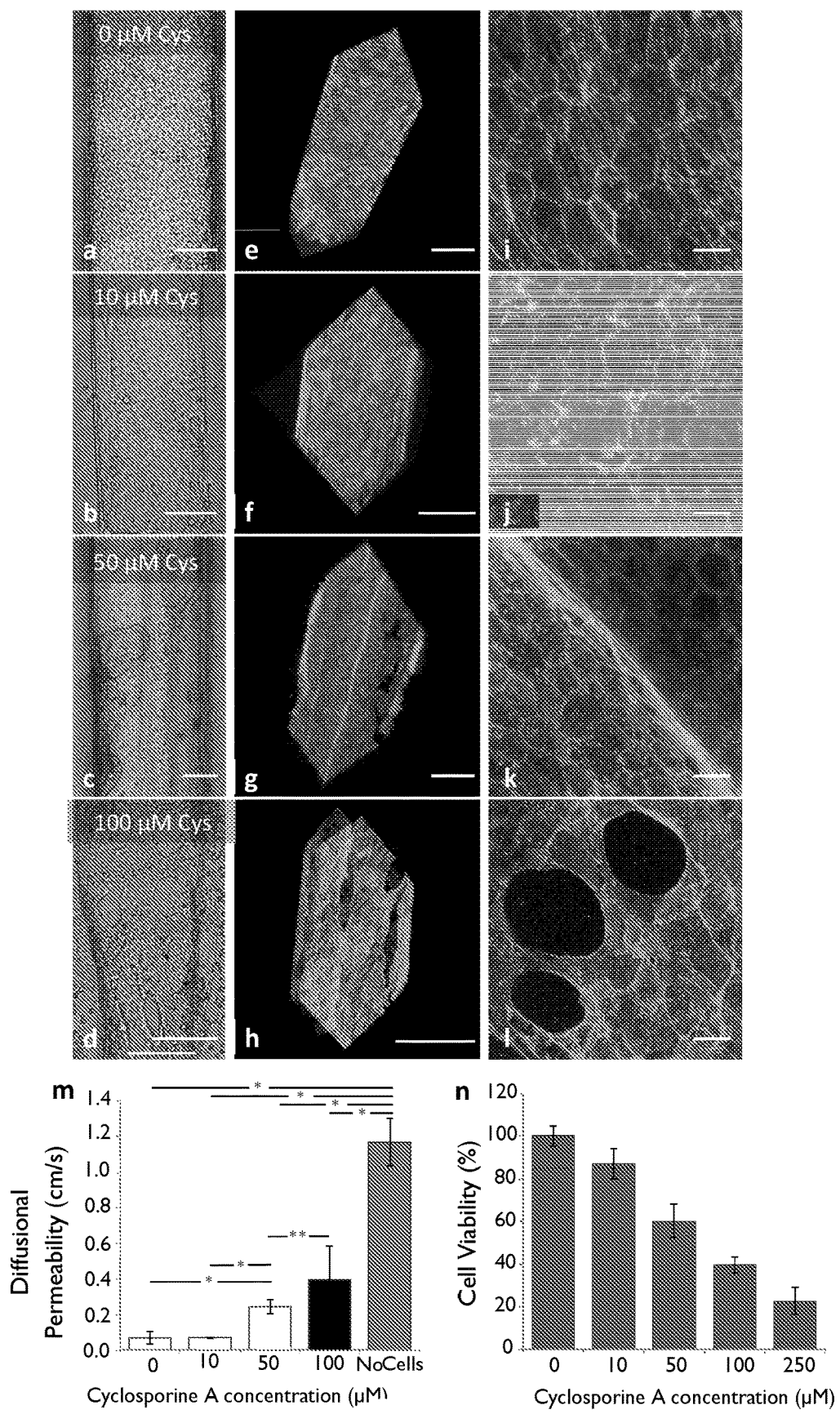

FIG. 7 depicts Cyclosporine A-induced cytotoxicity: (A-D) Brightfield images, (E-H) 3D renderings, and (I-L) high magnification images of printed and perfused 3D PTs dosed with varying concentrations of Cyclosporine A for 24 h, where actin (green) and nuclei (blue) are stained, scale bars=200 μm (A-H) and scale bars=20 μm (I-L), respectively, (M) Diffusional permeability measurements taken after dosing with Cyclosporine A, *p<0.003, **p<0.02, (N) Cell viability measured for the 2D control (on bare dish) after dosing with Cyclosporine A (all populations shown are statistically significantly different with a p<0.005).

Figure 8:
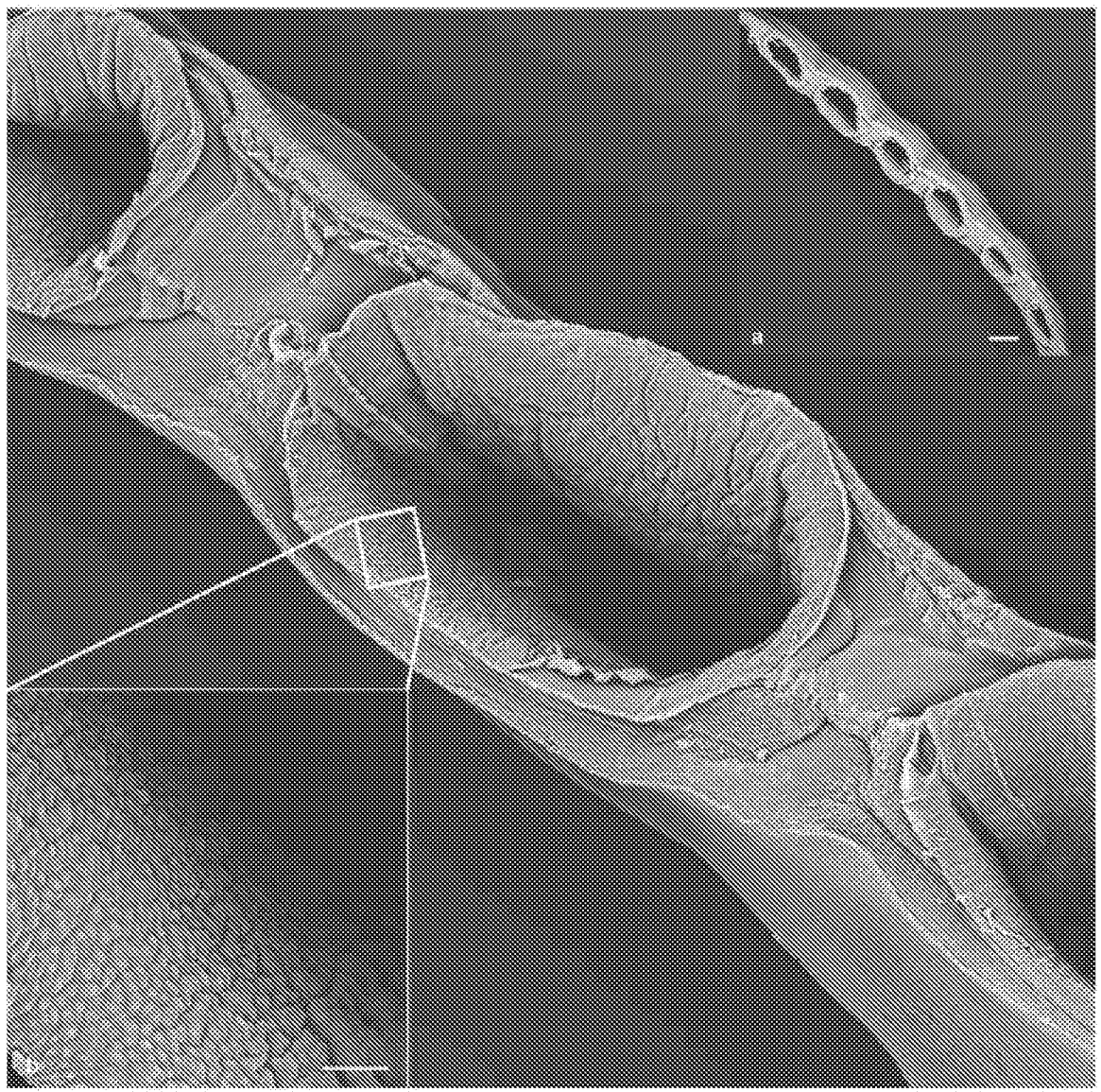

FIG. 8 depicts multiplexed 3D proximal tubules: (A) SEM image of 6 PTs printed adjacent to one another, scale bar=500 μm. [Note: The image is acquired on a thin dried slice cut from the printed sample.], (B) High magnification image taken inside the larger 3D PT shown in the background, scale bar=50 μm. As shown here, multiple PTs can be printed in parallel and lined with PTEC cells that grow to confluency.

Figure 9:
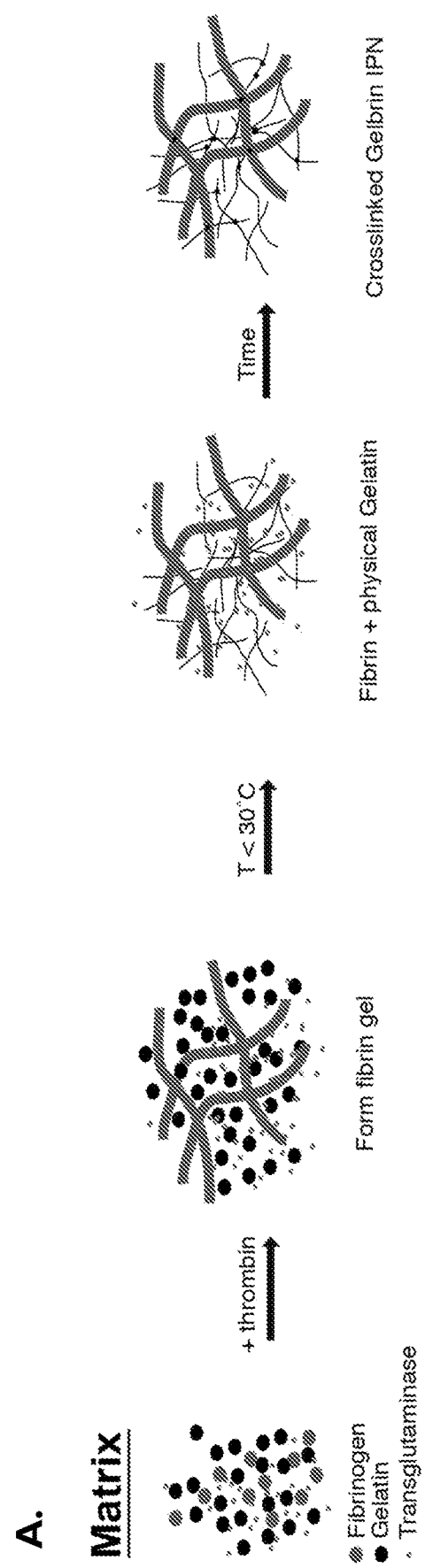
Figure 9:
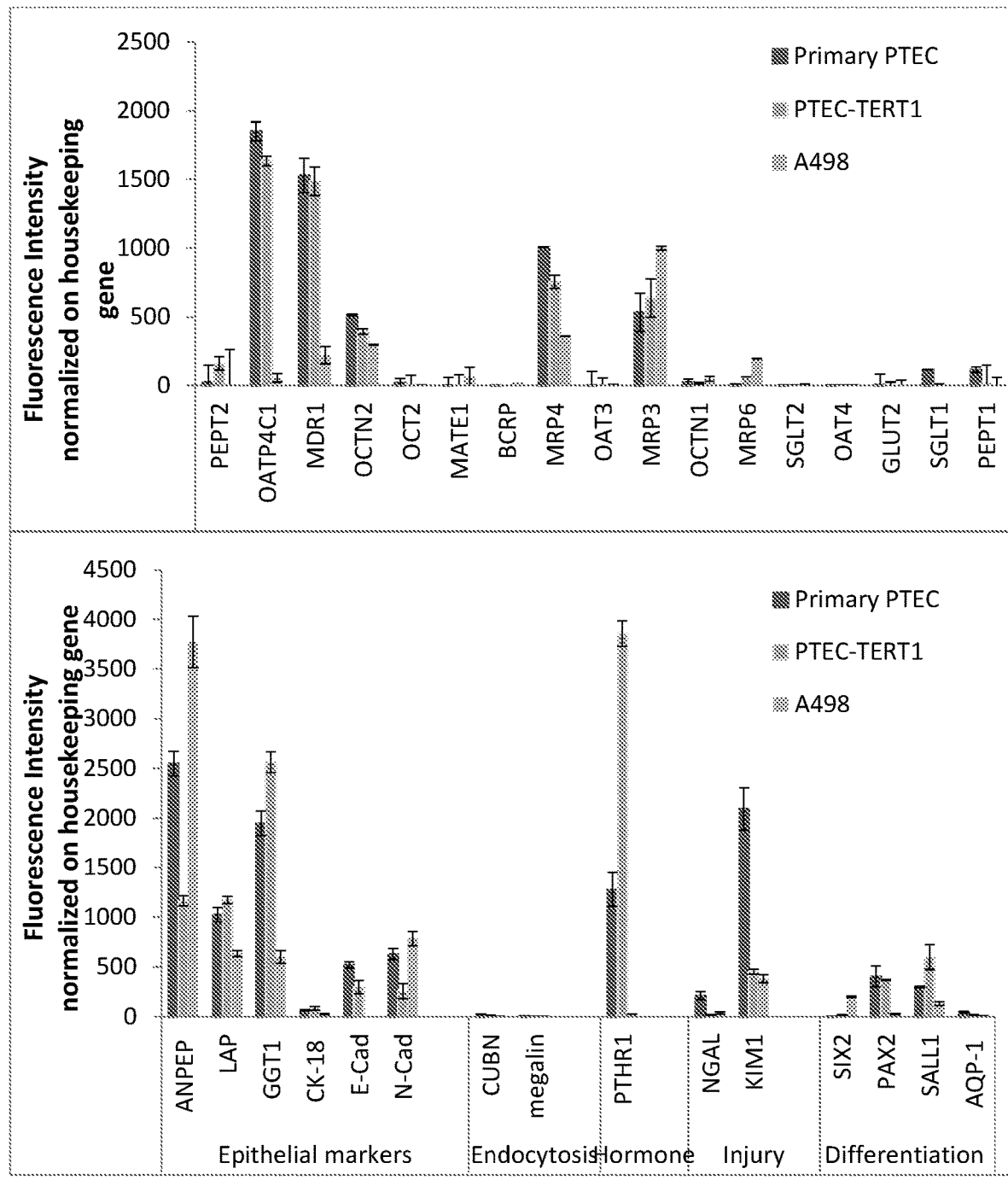

FIG. 9 depicts engineered extracellular matrix (ECM) and gene expression profiles for various PTEC lines: (A) Schematic representation of the ECM constituents and their gelation and crosslinking as a function of different stimuli, (B) relative mRNA levels of 33 selected genes related to renal epithelial function, transport, endocytosis, hormone response, injury response, and cell differentiation for three cell lines (primary renal PTEC, PTEC-TERT1, and the A498 cancer renal cell line). PTEC-TERT1 cells are transcriptionally similar to primary PTEC and different from the A498 renal cancer epithelial cell line.

Figure 10:
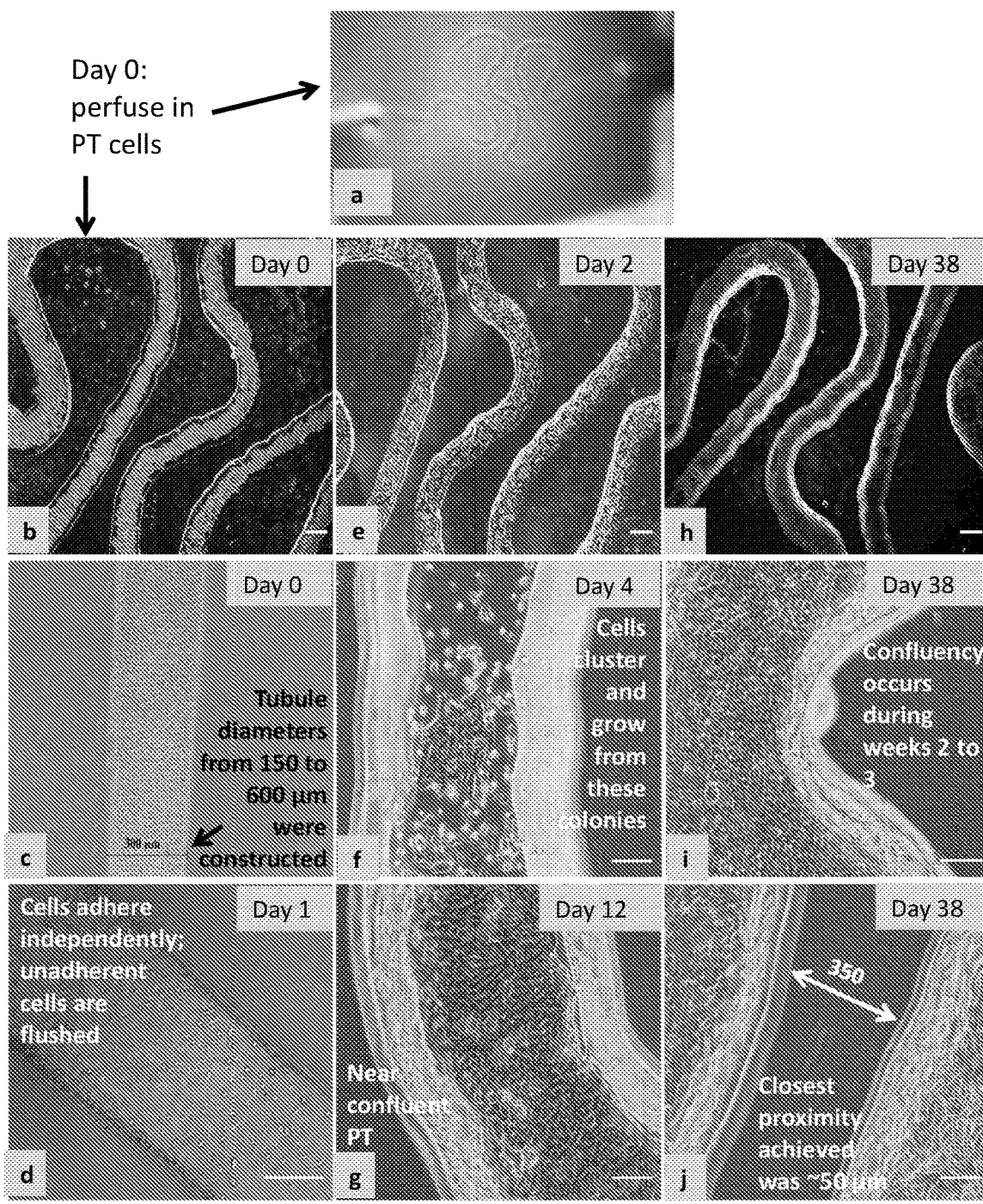

FIG. 10 depicts 3D proximal tubule maturation process: (A) A photo of a mature (fully confluent) tubule, (B) PTEC loading at Day 0, scale bar=500 μm, (c) higher magnification view of PTEC loading, scale bar=300 μm, (d) PTECs adhering to the tubule at Day 1 after non-adherent cells are flushed away, scale bar=200 μm, (e) low magnification view of PTECs growing into the tubule at Day 2, scale bar=500 μm, (f) image at Day 4 where cells grow from colonies or clusters, scale bar=100 μm, (g) image at Day 4 where cells are near confluency, scale bar=100 μm, (h) image of a mature tubule at Day 38, scale bar=500 μm, (i) higher magnification view of the confluent tubule at Day 38, scale bar=100 μm, (j) image of the tubule, which approaches within 350 μm of itself due to its convoluted architecture, scale bar=100 μm, (k) timeline of construction and maturation of the PT model.

Figure 11:
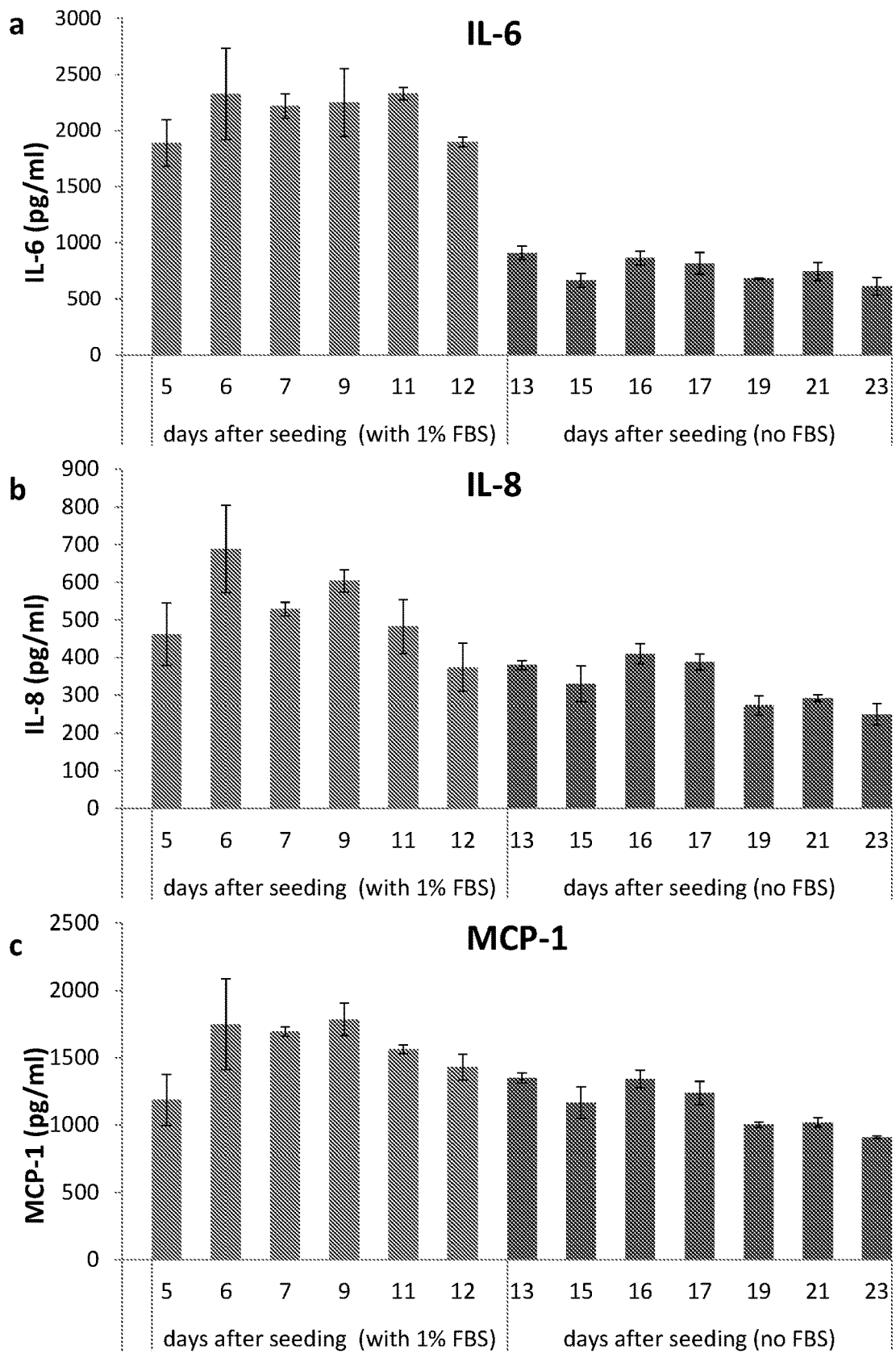

FIG. 11 depicts 3D proximal tubule perfusate analysis. The relative concentration of (A) IL-6, (B) IL-8, and (C) MCP-1, shed in the media perfusing through the tubule with time. The light grey bars represent the growth phase of the tubule. At Day 12, the tubule is near confluency, FBS is removed from the media, and the profile of the confluent tubule is shown in dark grey bars. Note that once confluency is reached and FBS is removed, cytokine levels stabilize.

Figure 12:
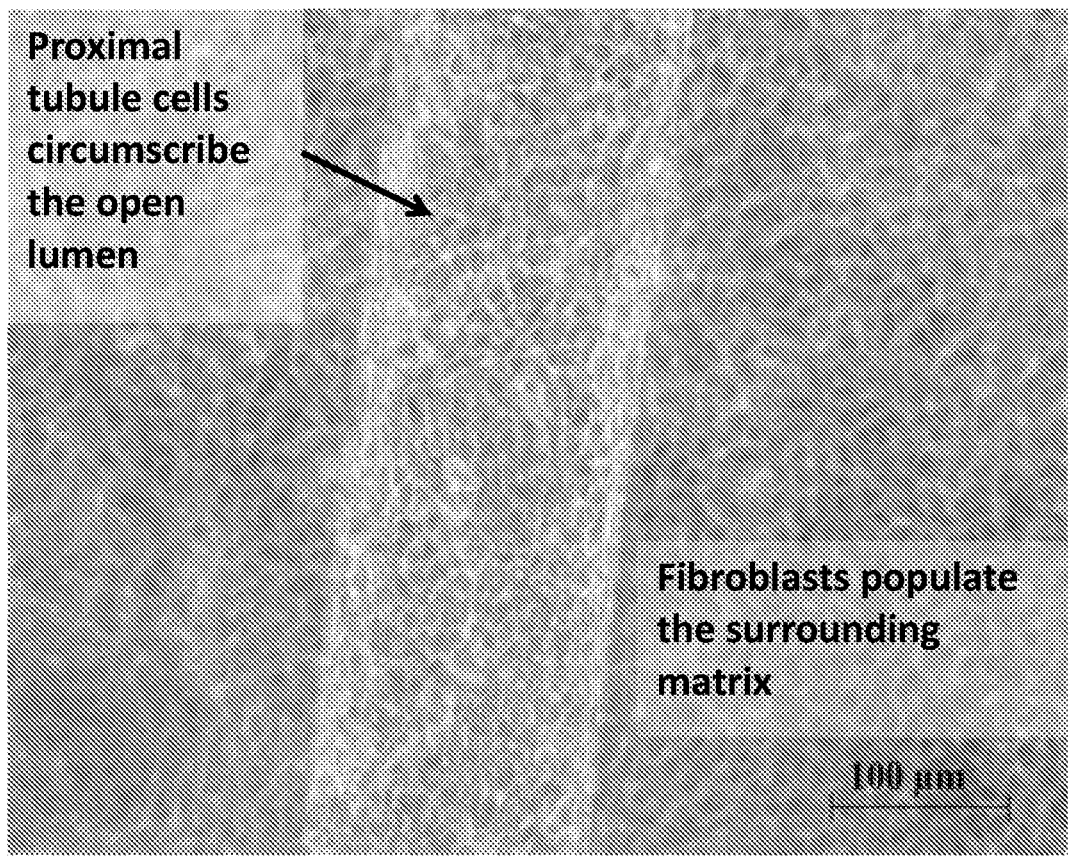

FIG. 12 depicts 3D proximal tubule lined with PTEC cells and embedded in a fibroblast-laden extracellular matrix. Phase contrast image of a 3D PT grown to a confluent epithelium, in which fibroblasts thrive in the surrounding ECM, scale bar=100 μm.

Figure 13:
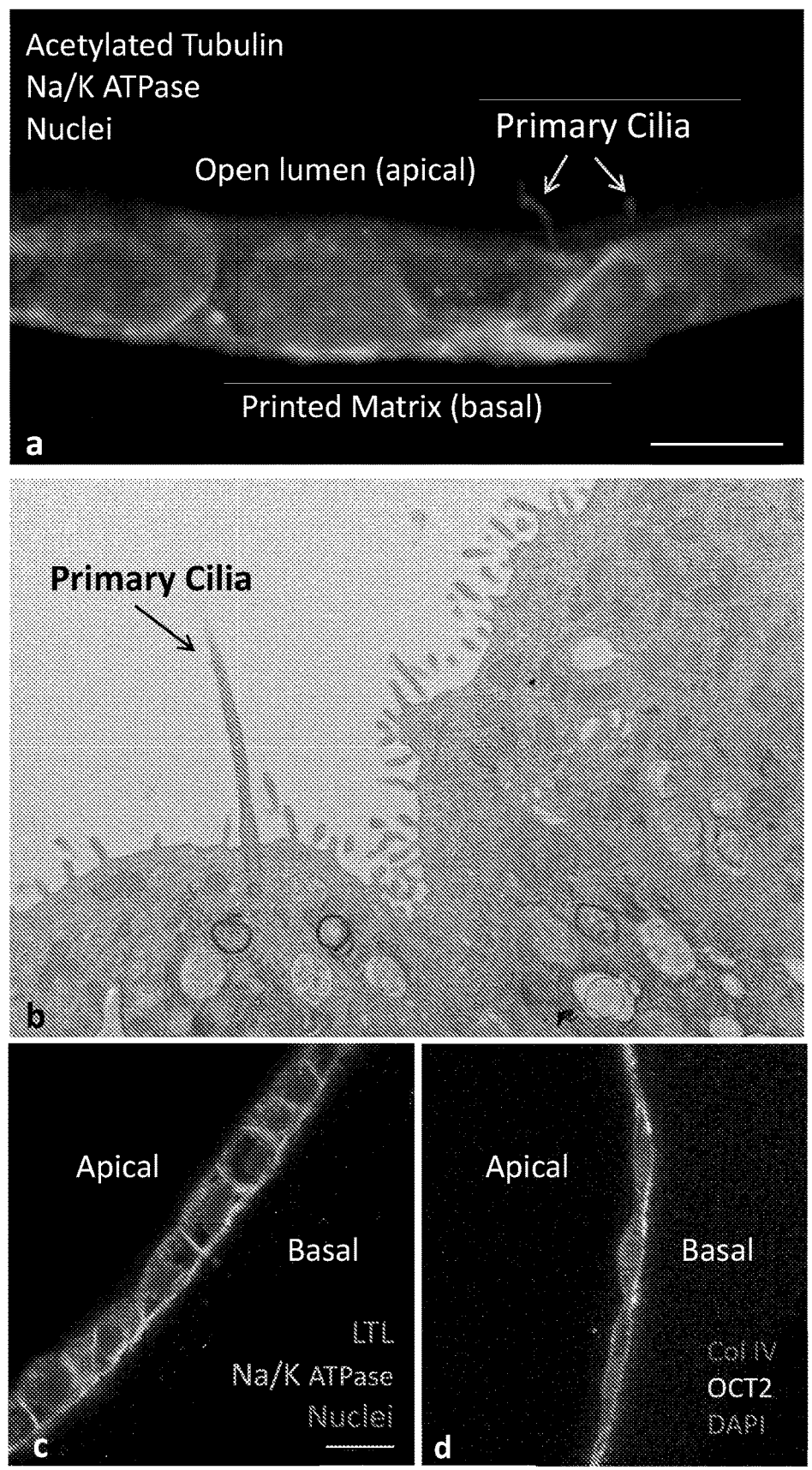

FIG. 13 depicts PTEC characterization within printed and perfused 3D proximal tubules. (A) 3D reconstruction of PTECs stained for Na+/K+ ATPase (green) and acetylated tubulin (red) where basal-lateral expression of Na+/K+ ATPase is apparent and two primary cilia are visible on the apical side, scale bar=10 μm and (B) TEM image of primary cilia, scale bar=1 μm. (C) Cross-section of the tubule showing apical expression of LTL (magenta) and basal expression of Na/K ATPase (green), scale bar=15 µm, (d) Cross-section of the tubule showing basal expression of OCT2 (yellow) and collagen IV (red), scale bar=15 µm.

Figure 14:
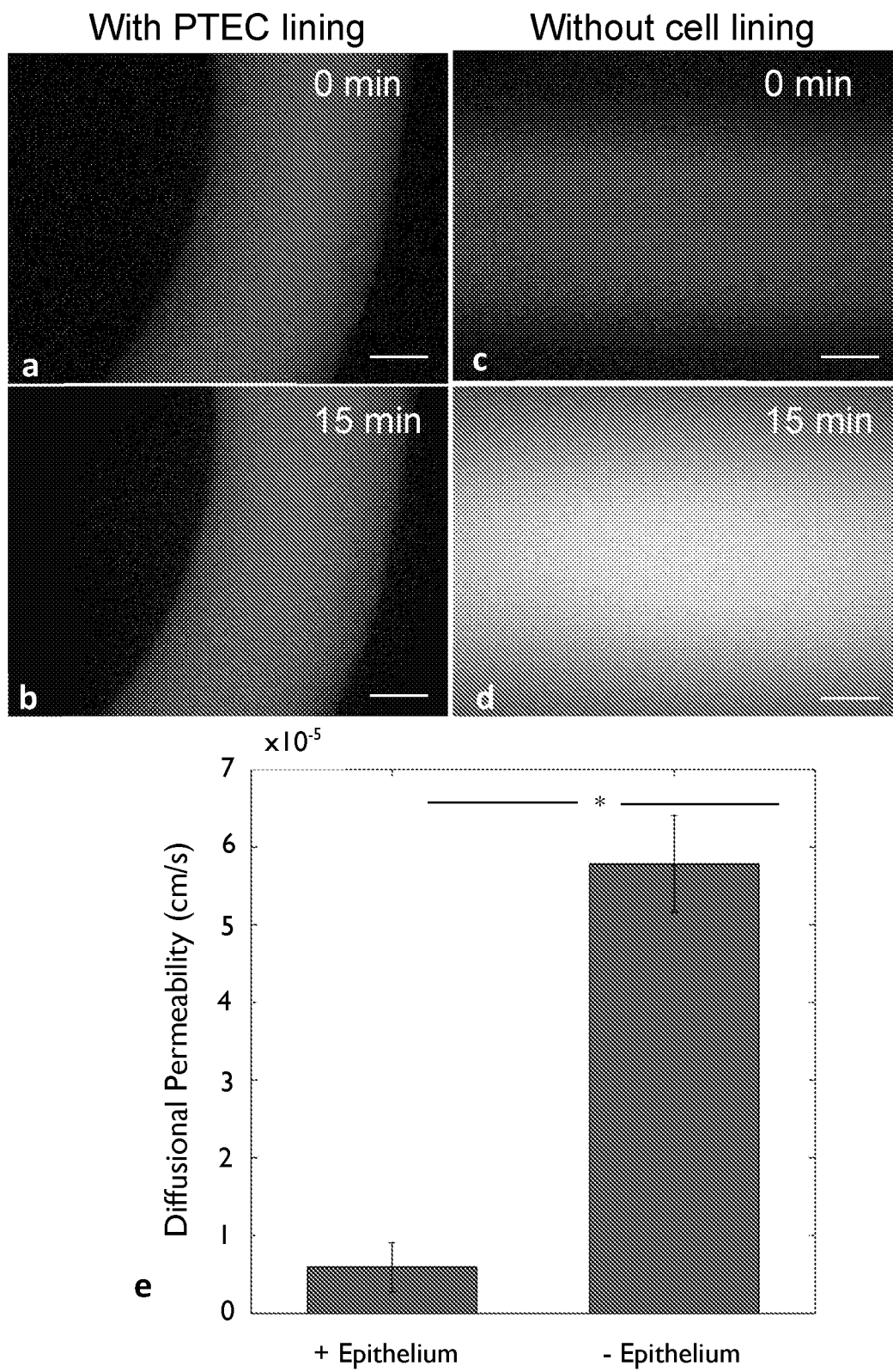

FIG. 14 depicts diffusional permeability measurements. FITC-labeled inulin (4.5 kDa) suspended in cell media is perfused through the 3D PT lined with confluent PTECs and fluorescent images are captured at varying times: (A) t=0 min and (B) t=15 min for cell lined channels, and (C, D) t=0 min and 15 min, respectively, for control samples composed of a bare 3D PT (without PTECs), in which the FITC-labeled inulin diffuses much faster into the surrounding ECM, scale bars=100 µm. (E) Measured diffusional permeability of 3D PT channels with and without proximal tubule epithelium, *p>0.001.

Figure 15:
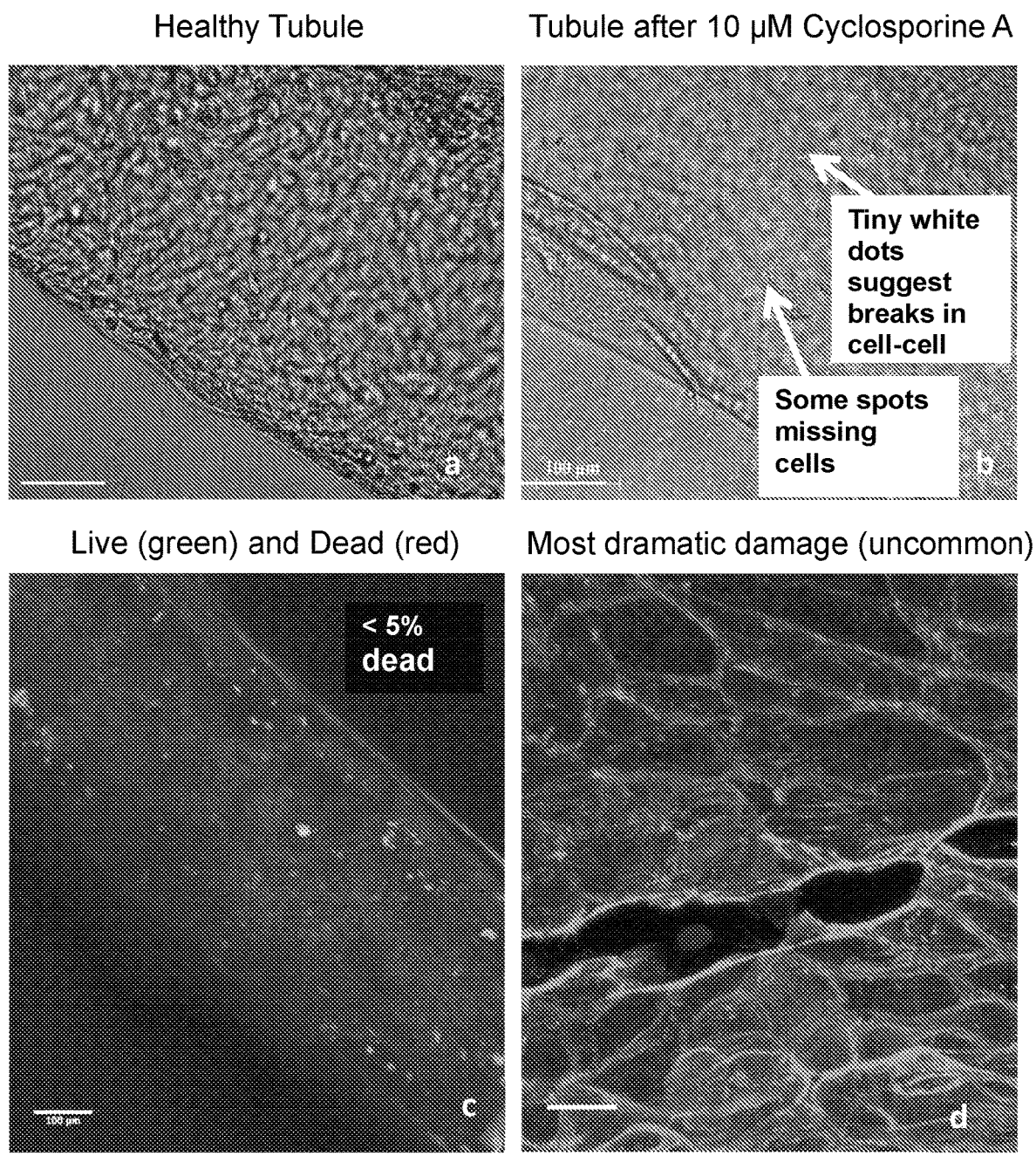

FIG. 15 depicts observed damage for printed and perfused 3D proximal tubules dosed with 10 µM cyclosporine A. (A) Brightfield image of a healthy proximal tubule at 4 weeks, scale bar=100 µm, (B) brightfield image of a tubule after 24 h of cyclosporine A exposure, scale bar=100 µm, (C) live (green) and dead (red) staining of the tubule at 24 h after cyclosporine A exposure showing that <5% of the total cells are dead, scale bar=100 µm, (D) high magnification image showing the most dramatic, but quite uncommon, damage observed under these conditions, where actin (green) and nuclei (blue) are stained, scale bar=20 µm.

Figure 16:
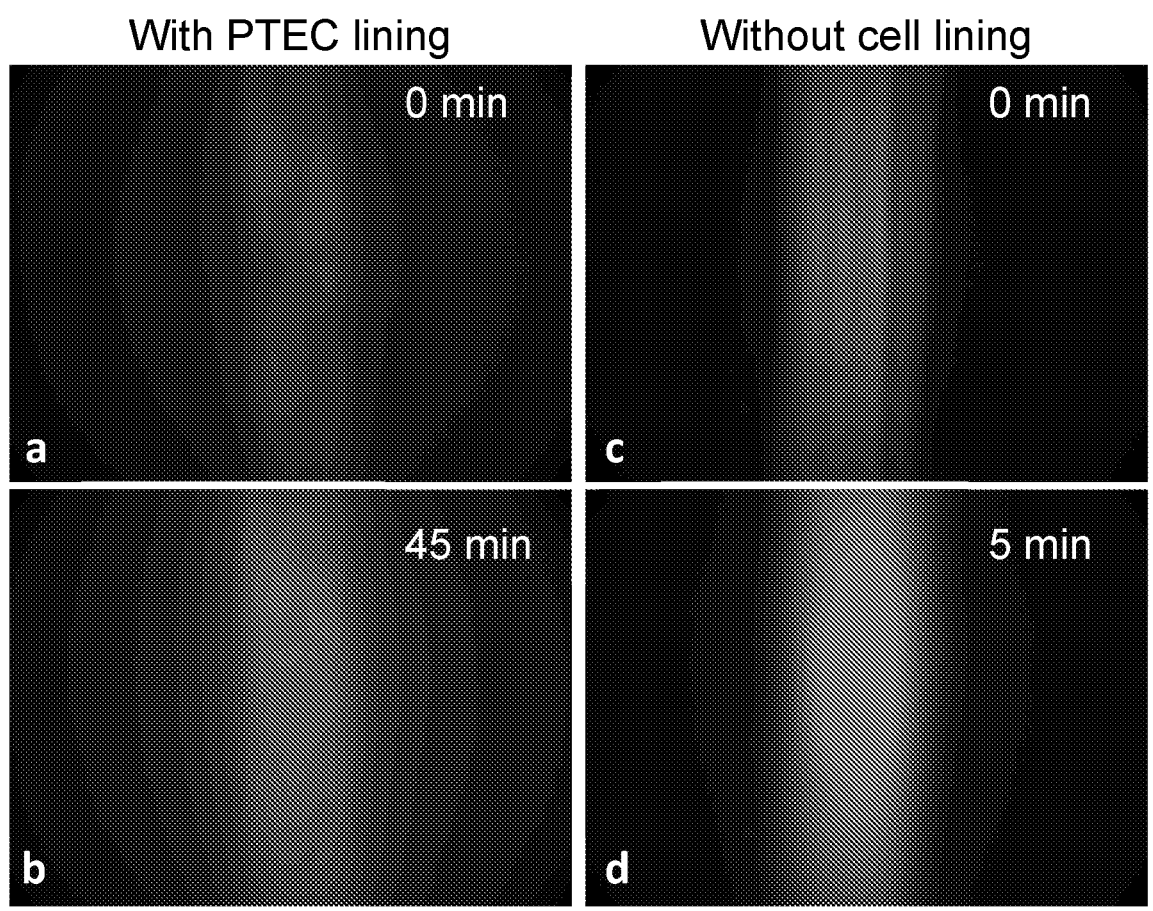

FIG. 16 depicts diffusional permeability measurements for the Cyclosporine A study. FITC labeled dextran (70 kDa) solution is perfused through the 3D PT lined with confluent PTECs and fluorescent images are captured at varying times: (A) t=0 min and (B) t=45 min for cell lined channels, and (C, D) t=0 min and 5 min, respectively, for control samples composed of a bare 3D PT (without PTECs), in which the FITC-labeled dextran diffuses much faster into the surrounding ECM, scale bars=200 µm.

Figure 17A:
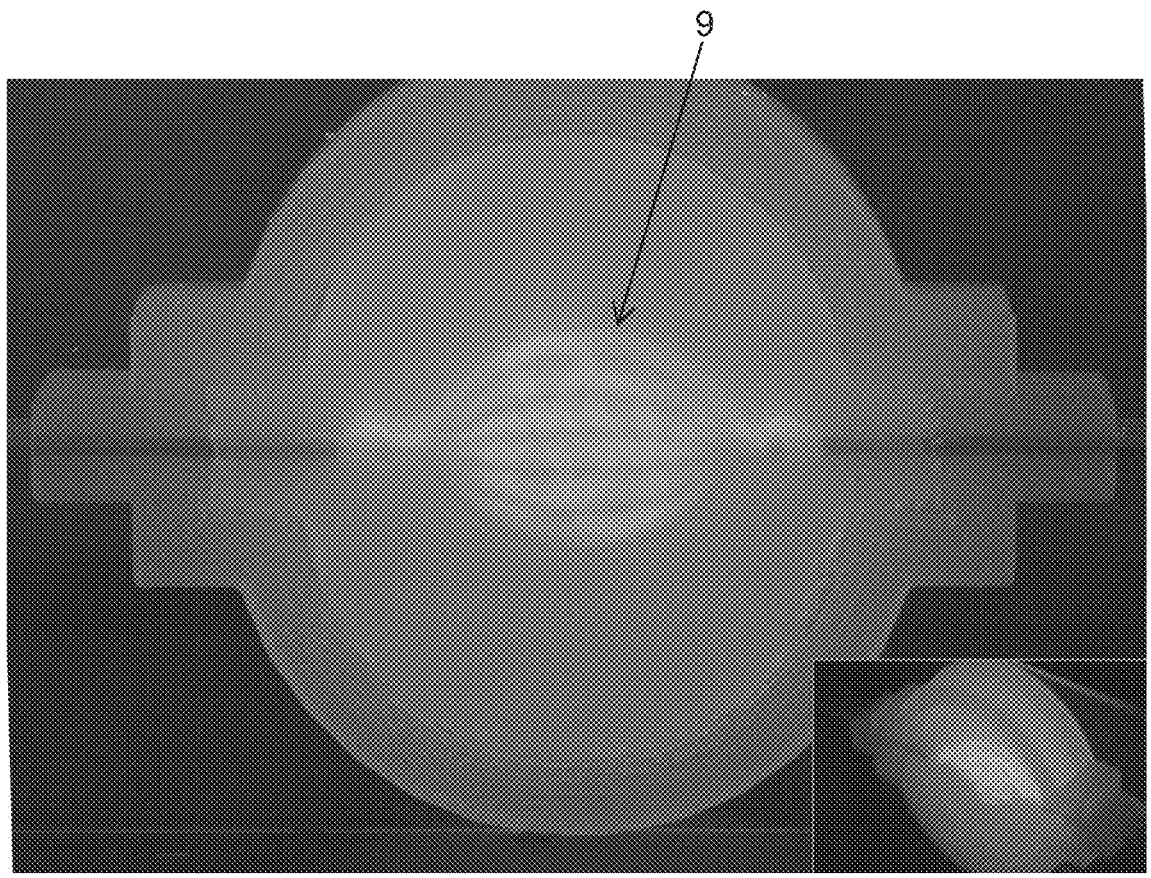

FIG. 17A depicts a photograph of our PT model constructed with 3 layers of independently addressable perfusable tubes. The inset shows the 3 pins connected to 3 separate tubes perfused with fluorescent dyes. This multilayer model is a demonstration showing how bioprinting can be combined with microfluidics to interface vascular layers and proximal tubules in 3D.

Figure 17B:
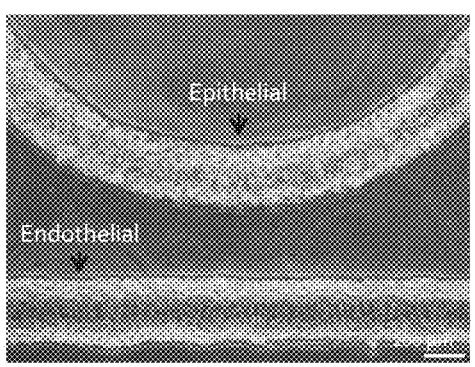

FIG. 17B depicts cells loaded in two channels surrounded by extracellular matrix. Specifically, in the endothelial channel, endothelial cells, such as GMECs or HUVECs, are loaded and maturing in the channel under perfusion. In the epithelial channel, epithelial cells, such as PTECs, are loaded and maturing in the channel under independently controlled perfusion. This figure demonstrates that bioprinted channels can get close enough on perfusable chip to exchange proteins and other biological signaling molecules. The distance between the channels can be as low as 20 um or less, shown here is a separation of ~300 um.

Figure 17C:
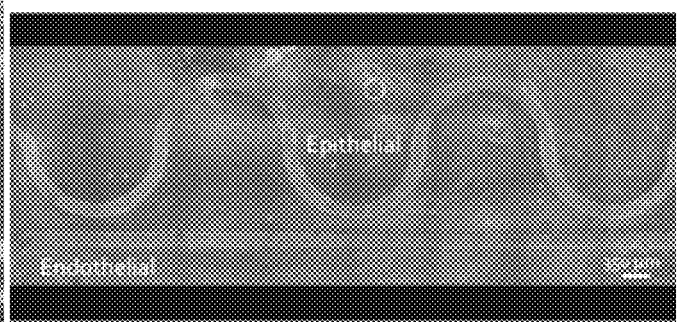

FIG. 17C depict s a backed out view of the image in 17B where the macroscopic architecture is shown. Many different architectures of combining epithelial and endothelial tubules are possible. In this configuration, one tubule is curved and the other is straight. They can both also be straight, curved, or weaving in and out of plane in three dimensions in other embodiments.

Figure 18:
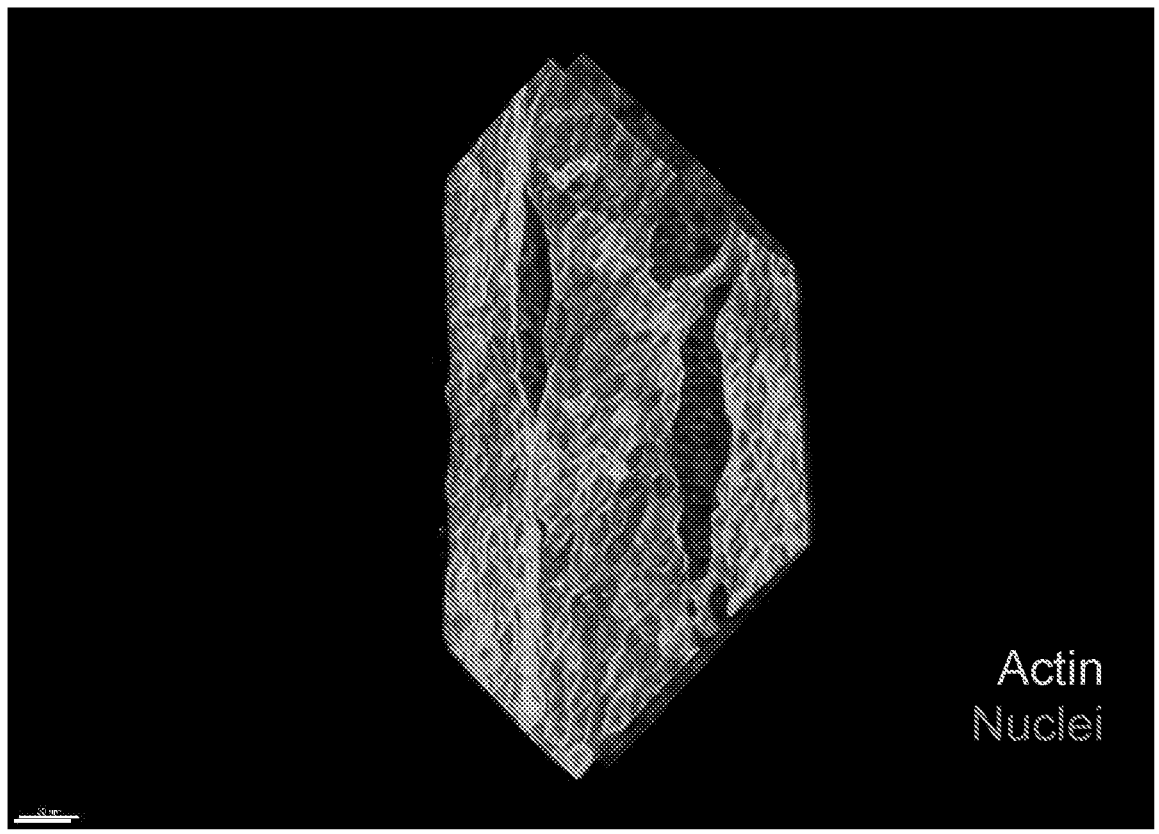

FIG. 18 depicts 3D rendering of a printed and perfused 3D proximal tubule after dosing with 100 µM Cyclosporine A for 24 h. The PT is stained with phalloidin and dapi to visualize actin filaments and cell nuclei, respectively.

Figure 19:
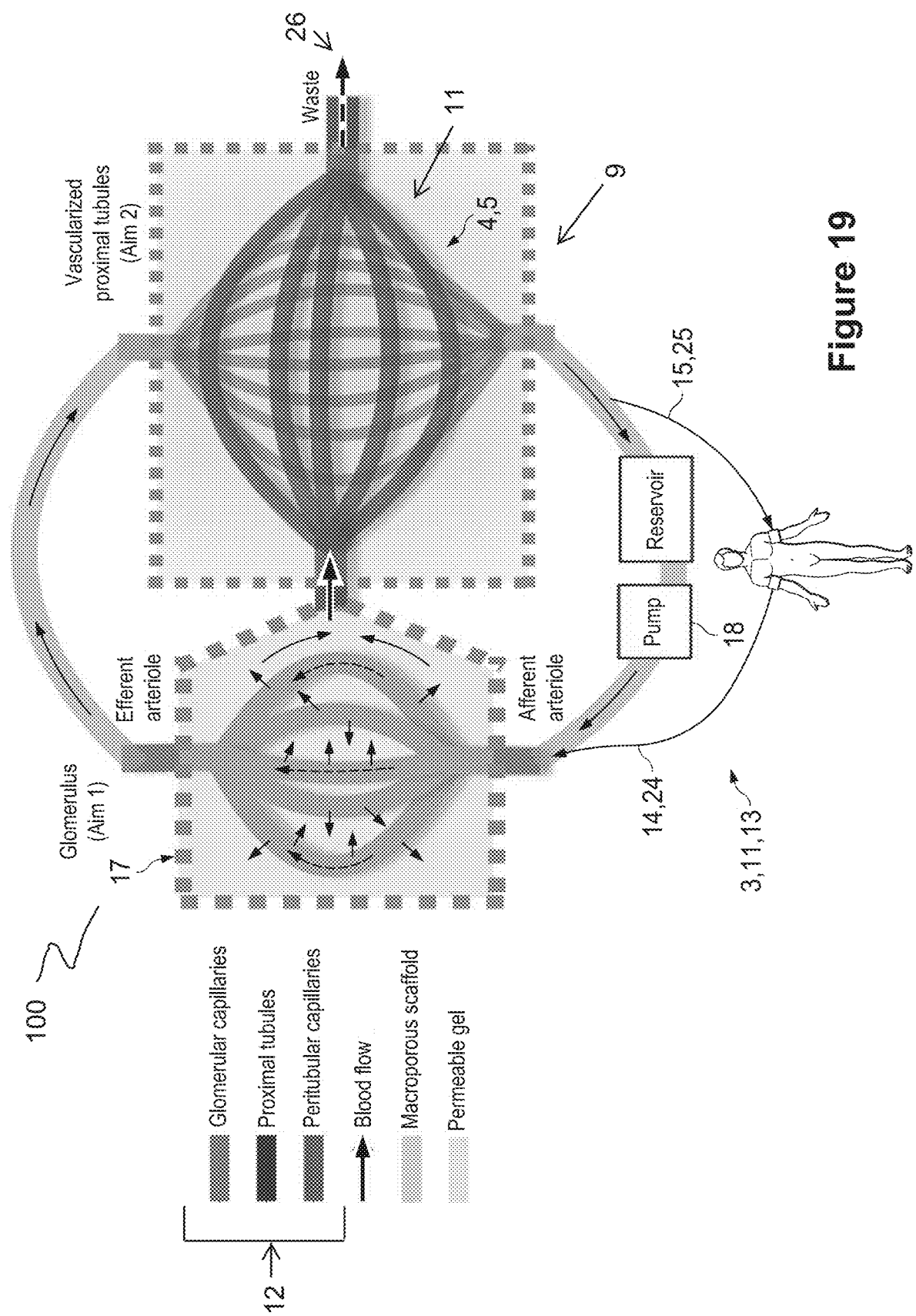

FIG. 19 depicts a schematic of the blood flow in the proposed the Living Integrated Filtration-Reabsorption Extracorporeal (LIFE) device system 100. The LIFE device will mimic the physiological flow configuration, in which the plasma flows through the glomerulus and then proximal tubules. Subsequently, the nutrients in the plasma are reabsorbed by the PT and transferred to the blood stream that will again flow through the glomerulus.

Figure 20:
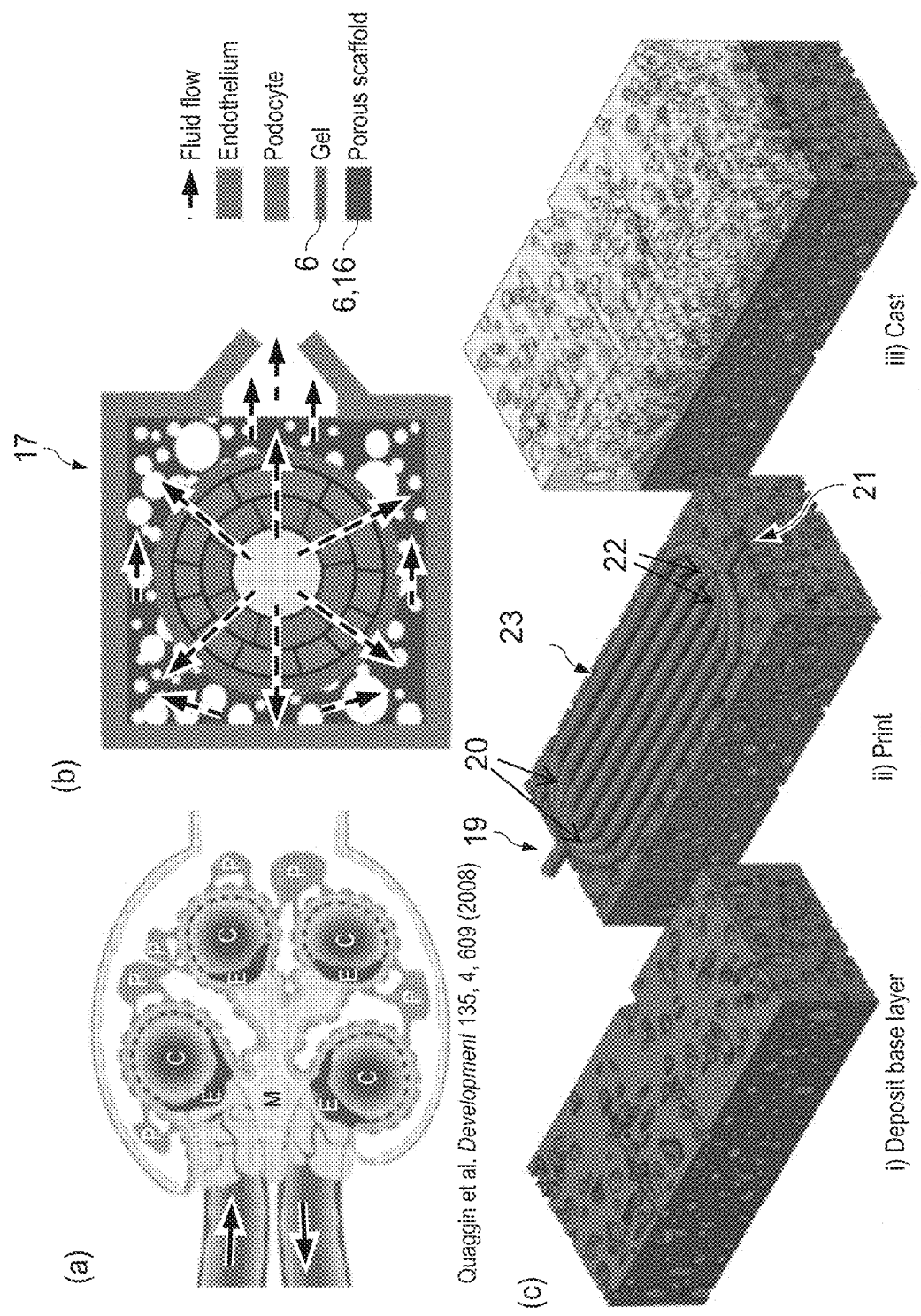
Figure 2I:
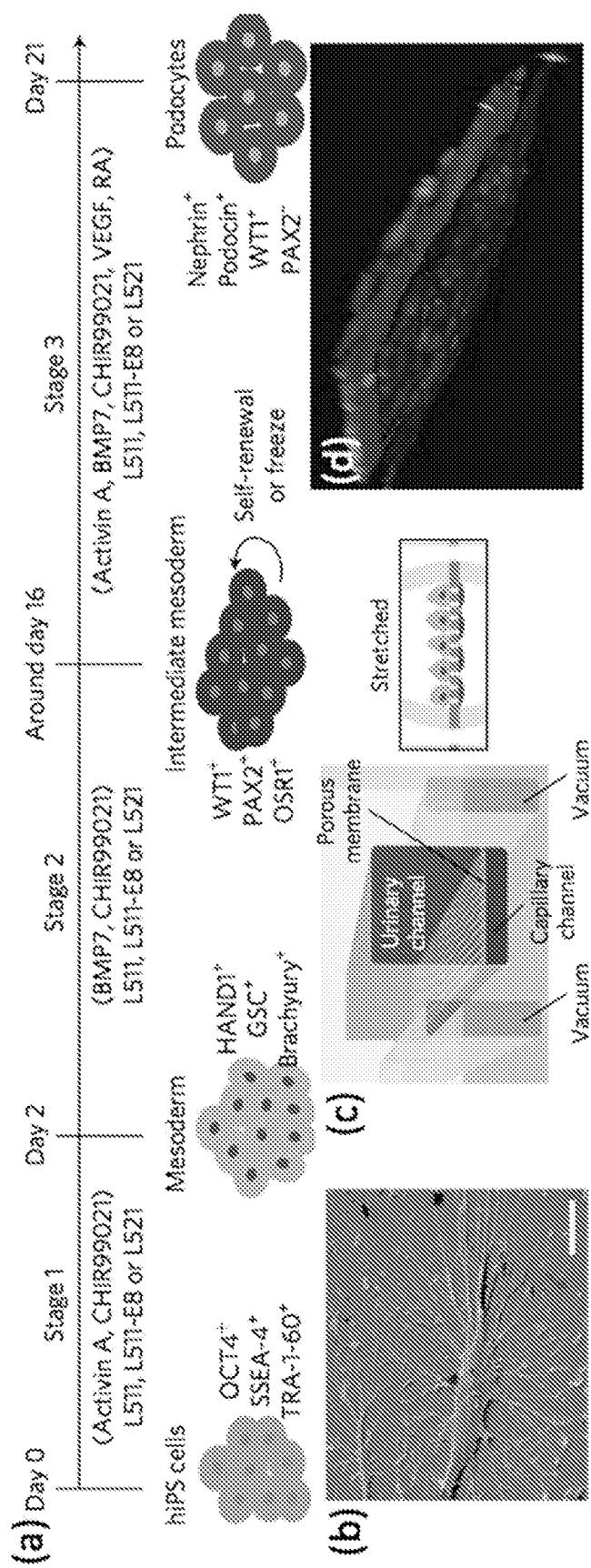

FIG. 20 depicts schematics of the 3D glomerulus model design and manufacturing steps: (A) In vivo, glomerular capillaries (C) are tightly packed channels stabilized by podocytes (P), and are supported by the mesangium (M) enclosed in the Bowman's capsule (BC), (B) the three distinct layers of the bioprinted glomerular capillary: endothelium, podocytes, and degradable gel supported by a macroporous scaffold, and (C) method of manufacture of the bioprinted glomerular capillary.

FIG. 21 depicts: (A) Schematic overview of the timeline for directed differentiation of iPSCs into podocytes. BMP7, (B) SEM images showing that the iPSC-derived podocytes exhibit primary and secondary cell processes, (C) schematic of the previously used microfluidic device with microchannels replicating the urinary and capillary compartments of the glomerulus, (D) 3D reconstructed confocal image of the tissue-tissue interface formed by iPSC-derived podocytes (top, green) and human glomerular endothelial cells (bottom, magenta).

Figure 22:
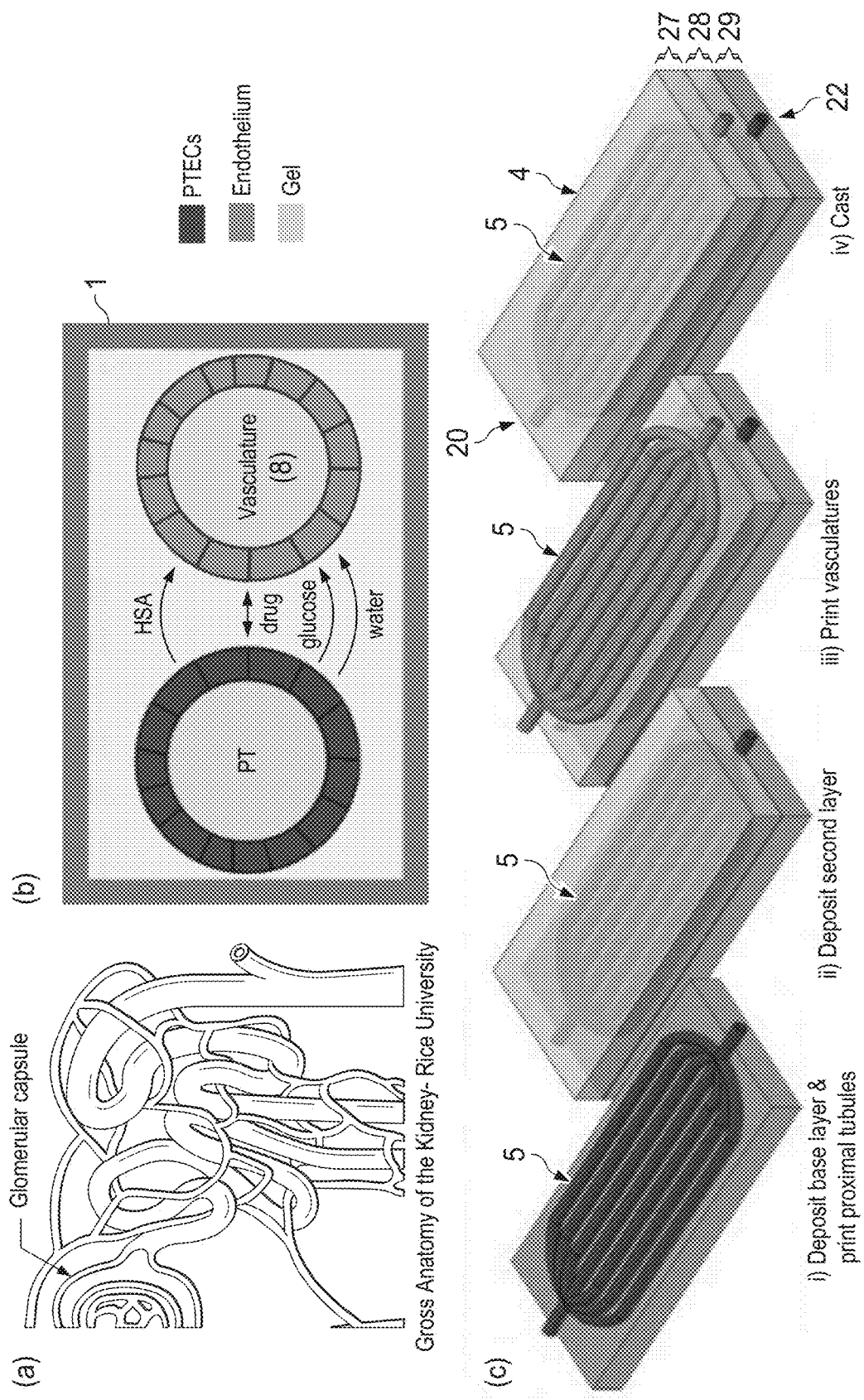

FIG. 22 depicts schematic views showing the design criteria and manufacturing steps of the 3D vascularized proximal tubule (PT) model: (A) In vivo the peritubular capillary network surrounds the convoluted segments of tubules, (B) two side-by-side channels within a permeable hydrogel to enable molecule and fluid exchange between the PT and vasculature via diffusion, osmosis, and active cell transport, (C) 3D bioprinting method of a double-layered tubule network (the blue tubules denote proximal tubules, and the red tubules are the vascular conduits; the thin gel layer separating these two networks is highly permeable, and thus allows molecules to diffuse across efficiently).

Figure 23:
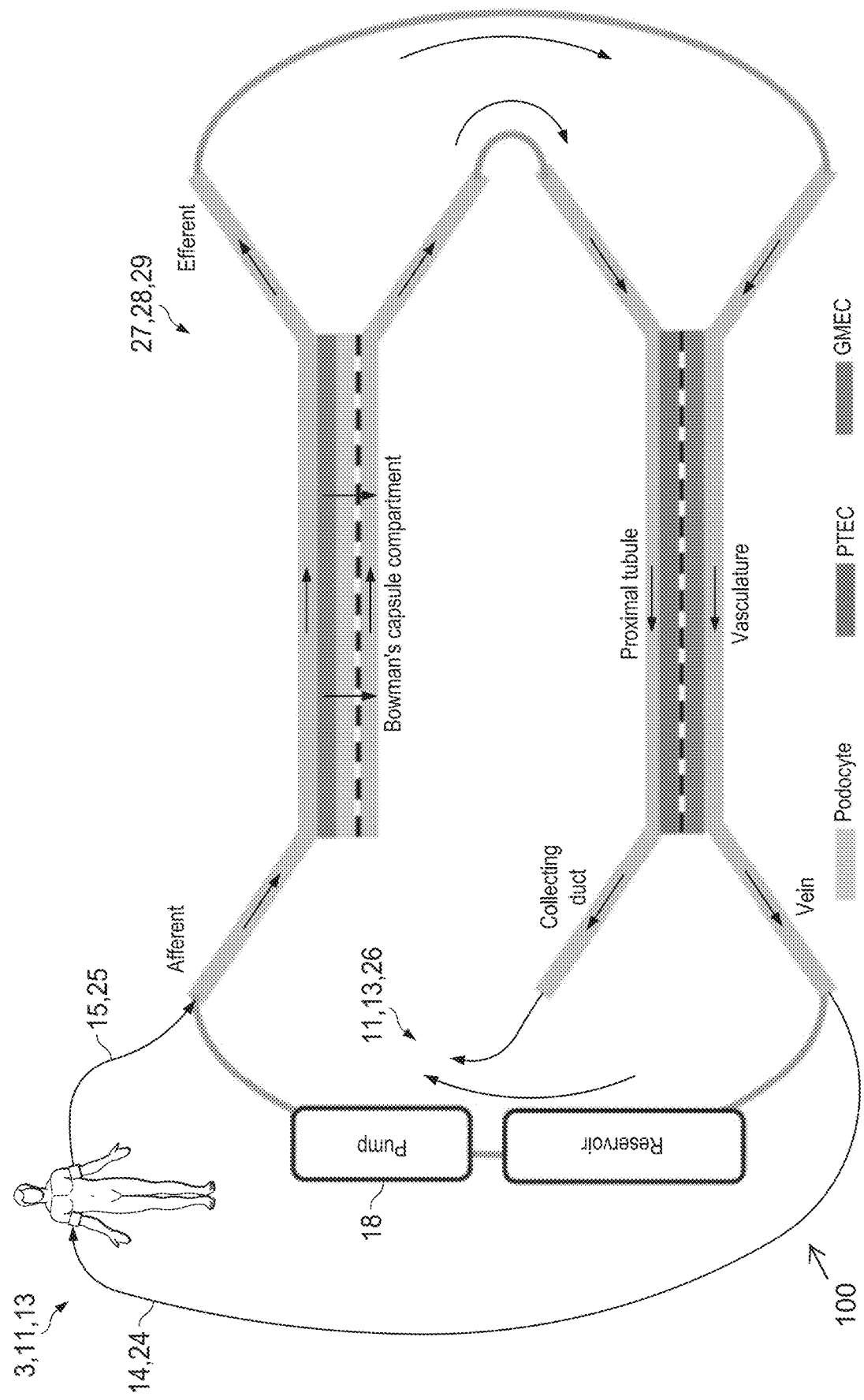

FIG. 23 depicts a diagram illustrating the flow of the blood (could be substituted by perfused media or other biological-like fluids) in the LIFE device. The main stream of the perfusate is driven by the pump flowing through each part of the device in the following order: afferent arteriole, glomerular capillary, Bowman's capsule compartment, proximal tubule, and then outlet to collecting duct. In this device configuration, the cells are on thin membrane sheets instead of surrounded in 3D by ECM materials.

DETAILED DESCRIPTION OF THE DRAWINGS AND THE PRESENTLY PREFERRED EMBODIMENTS

U.S. Provisional Patent Application No. 61/900,029, filed on Nov. 5, 2013; International Patent Application No. PCT/US2014/063810, filed on Nov. 4, 2014, all are hereby incorporated by reference in their entirety.

U.S. Provisional Patent Application No. 62/127,549, filed Mar. 3, 2015; and U.S. Provisional Patent Application No. 62/250,338, filed on Nov. 3, 2015; International Patent Application No. PCT/US2016/020601, filed Mar. 3, 2016 are hereby incorporated by reference in their entirety.

U.S. Provisional Patent Application No. 62/157,286, filed May 5, 2015; and International Patent Application No. PCT/US2016/030710, filed May 4, 2016 are hereby incorporated by reference in their entirety.

U.S. Provisional Patent Application No. 62/294,118, filed Feb. 11, 2016 is hereby incorporated by reference in its entirety.

Figure 1:
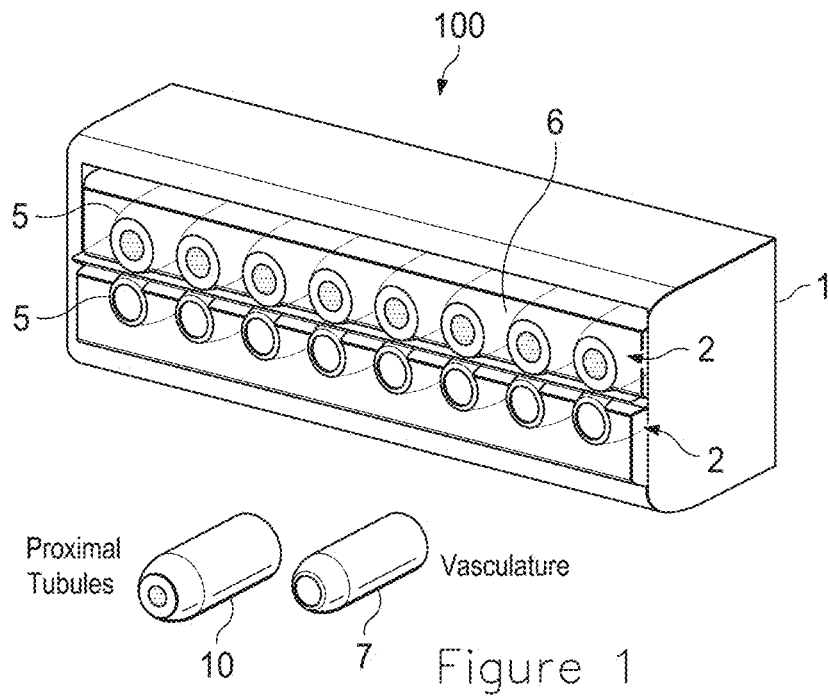
FIG. 1 depicts an exemplary embodiment of the described apparatus 100.
Figure 2:
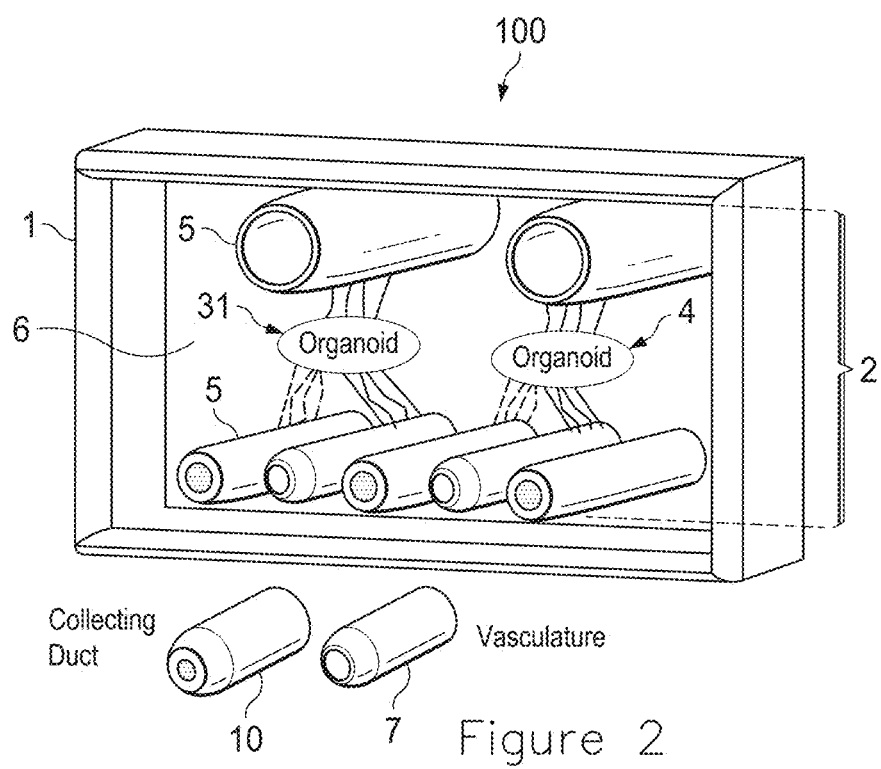
FIG. 2 depicts another exemplary embodiment of the described apparatus 100.

Referring to FIGS. 1 and 2, described is an apparatus 100 capable of housing biocompatible and living (e.g., human or animal) components 2 that can be perfused with bodily fluids to recondition the blood of a patient. The apparatus 100 may be adapted for extracorporeal use, or may be an implantable apparatus with a hard casing (i.e., "housing" 1) or no casing at all.

As such, certain embodiments relate to an apparatus 100 for use in connection with organ replacement or organ assist therapy in a patient. The apparatus may include a housing 1 defining an interior cavity, a programmable mammalian (e.g., human or animal, e.g., cat, dog, horse, cow, etc.) tissue construct 2 comprising viable cells disposed in the housing 1, and a patient interface 3 (as seen in FIGS. 19 and 23) for communication of bodily fluids between the patient and the tissue construct 2 disposed in the housing 1. As bodily fluid comes in contact with the programmable (external) mammalian tissue, a multitude of different tissue functions may be enacted on the fluid including filtration, reabsorption, metabolism, concentrating, excretion, composition modification, conditioning, or immune modulation, or any other organ function.

The term "housing" refers to any hollow structure adapted to and dimensioned to contain a viable tissue construct. The housing can be of any suitable shape, such as sphere, cube, cuboid, cylinder, capsule, kidney bean, or any other suitable shape. Exemplary device 100 is shown in FIG. 1 and FIG. 2. As shown in FIG. 1 and FIG. 2, the housing 1 defines an interior space and can contain the tissue construct 2.

The term "tissue construct" refers to any viable cells or tissues, including but not limited to viable cells, which may be patient-derived, organoids, single or mixed-population organoids, embryoid bodies, endothelial sprouts, autologous tissue, allogeneic tissue, xenogeneic tissue, printed tissue constructs, or the like. The tissue construct may be a human tissue construct. The tissue construct may be an animal (e.g., cat, dog, horse, cow, etc.) tissue construct. The tissue construct may be a tree-dimensional-printed tissue construct; however, the tissue construct is not limited to a three-dimensional-printed tissue construct. The term "a programmable mammalian tissue construct" relates to design and assembly of mammalian tissue constructs with programmed structure and function. The tissue construct 2 may be selected from viable cells, organoids, embryoid bodies, endothelial sprouts, autologous tissue, allogeneic tissue, xenogeneic tissue, and a three-dimensional-printed tissue constructs. The autologous, allogeneic, or xenogenic tissue may be patient (e.g., human or animal)-specific, off the shelf, or from another animal species.

The term "patient" refers to a human or animal (e.g., cat, dog, horse, cow, etc.) subject.

The tissue construct may be a tubular tissue construct. Exemplary tubular tissue constructs include, but are not limited to a nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

In certain embodiments, the tubular tissue construct is a human proximal tubule or tubules in addition to embedded vasculature 9.

In certain other embodiments, the tissue construct is an epithelial tissue construct.

In certain embodiments, these tissue constructs 2 include embedded vasculature 8 (see, e.g., FIG. 22B). 3D printed tissues constructs and organoids, and methods of producing the same were previously described in PCT Pub. No. WO 2015/069619 and its corresponding U.S. patent application Ser. No. 15/146,613, filed May 4, 2016; Application No. PCT/US2016/030710, filed May 4, 2016, entitled "Tubular Tissue Construct and a Method of Printing;" U.S. Prov. Application 62/294,118, filed Feb. 11, 2016, entitled "Mixed Population Organoids and Methods of Producing the Same," which are all incorporated by reference in their entirety.

The term "embryoid body" refers to a plurality of cells containing pluripotent or multipotent stem cells formed into a three-dimensional sphere, spheroid, or other three dimensional shape. The term "organoid" refers to an embryoid body whose cells have undergone a degree of differentiation. We acknowledge that the distinction between an organoid and embryoid body remains undefined, and the use of the terms should be considered interchangeable.

Referring to FIGS. 1, 2, 19, 20, and 22, a tissue construct 2 may include (i) one or more tissue patterns 4 (tissue pattern varieties are shown in FIGS. 2, 19, and 22), each tissue pattern 4 comprising a plurality of viable cells of one or more predetermined cell types, (ii) a network of channels 5 interpenetrating the one or more tissue patterns 4, said interpenetrating channels being 3D-printed with the tissue pattern 4, and, optionally, (iii) an extracellular matrix composition 6 at least partially surrounding the one or more tissue patterns 4 and the network of vascular channels 7. In an alternative embodiment, the channels can be molded; for example, arrays of fibers or pins can be created, with a matrix cast, where the pins are later removed.

A tissue construct suitable for placement into the housing of the described apparatus 100 is adapted for and capable of at least one of the following when in use:

(a) organ-like function selected from one or more of filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; and/or (b) production, secretion, and transfer of at least one of the same or another essential component or cell product into the patient's bodily fluid.

The viable cells of one or more cell types can be patient-derived cells.

The patient derived cells may include, but are not limited to, at least one of renal proximal tubule cells, loop of Henle cells, renal distal tubule cells, collecting duct cells, mesangial cells, renal microvascular cells, renal cell progenitors, pluri or multipotent stem cells, other endothelial lineage cells, endothelial cells, fenestrated glomerular endothelial cells, or iPSCs-derived patent-specific cell lines.

In certain embodiment, as shown in FIGS. 1 and 2, the tissue construct 2 may be at least partially surrounded by a biocompatible material. In certain embodiments, the biocompatible material may be an extracellular matrix material 6. The extracellular matrix material may include various components including, but not limited to, one or more of gelatin, fibrin, collagen I, or any other collagen type, alginate, PEG hydrogels, and gelatin methacrylate.

Referring to FIGS. 19 and 23, the described apparatus 100 also includes a patient interface 3 that comprises an extracorporeal circuit 13. The housing 1 is coupled with the extracorporeal circuit 13. The extracorporeal circuit 13 may include tubes 14, 15 for communication with an organ of a patient, blood vessel and/or a bioduct. For example, in certain embodiments, the extracorporeal circuit 13 may include (i) a first tube 14 configured for communication with an organ of the patient and allowing the flow of patient's bodily fluid from the patient's organ through the first tube 14 to the tissue construct 2; and (ii) a second tube 15 configured for communication with a blood vessel or a bioduct of the patient and allowing the flow of patient's bodily fluids from the tissue construct 2 through the second tube 15 to the patient.

In certain embodiments, the apparatus 100 is configured so that the tissue construct can be exposed to one or more biological agents, a biological agent gradient, a pressure, and/or an oxygen tension gradient.

In certain embodiments, the housing 1 of the described apparatus 100 is configured and dimensioned to be carried or worn by a patient. As such, in certain embodiments, the described apparatus 100 may be an extracorporeal device that is capable of replacing tissue or organ-level function (e.g., filtration, reabsorption, metabolism, concentrating, modifying or immune modulating). An extracorporeal device or apparatus has the advantage of being easily taken out of the circulation system compared to the efforts required to remove an implanted device, if needed.

In certain alternative embodiments, the apparatus 100 may be configured to be implanted into the patient's body as an organ replacement or assist.

As noted above, with reference to FIGS. 19, 20 and 23, the apparatus 100 also includes a patient interface. The patient interface may comprises an inlet manifold 19 on an inlet side of the housing 1 for distributing the bodily fluid to a plurality of inlet ports 20 of the network of interpenetrating channels and an outlet manifold 21 on the outlet side of the housing 1 for collecting the bodily fluid from a plurality of outlet ports 22 of the network of interpenetrating channels 5, 23. The network of interpenetrating channels 5 may comprise a first channel 24 for communication of arterial blood supply to the tissue construct, a second channel 25 for communication of venous blood away from the tissue construct, and a third channel 26 for communication of material extracted by the tissue construct from the arterial blood supply. The outlet manifold 21 can comprise at least three sections 27, 28, 29, a first section 27 coupled with the first channel of the network of interpenetrating channels, a second section 28 coupled with the second channel of the network of interpenetrating channels, and a third section 29 coupled with the third channel of the network of interpenetrating channels. Bodily fluids, such as blood or urine can be perfused through the channels where the cellular components mediate exchange.

Surprisingly, the device 100 is adapted for and capable of resorption of the essential components or cell products of the patient's bodily fluids undesirably excreted due to a disease or dysfunction of the patient's organ(s) and re-conditioning the biological fluids with these essential components and/or cell products. Also, the device is capable of producing and thereafter secreting the same or different essential components or cell products into the blood stream or body fluid.

In certain embodiments, the extracorporeal device is capable of resorption of the essential components of the patient's bodily fluids, which may be undesirably excreted due to a disease or dysfunction of the patient's organ(s), such as due to, e.g., Fanconi's Syndrome, and re-conditioning the biological fluids with these essential components. The device resorbs and delivers these essential components directly into the blood stream or body fluid. In addition, the device is adapted to produce and thereafter secrete the same or different essential components or cell products into the blood stream or body fluid.

The term "essential components" refers to various small molecules, ions, water, and proteins of metabolism. Essential components include, but are not limited to, for example, glucose, amino acids, uric acid, phosphate, bicarbonate, albumin, hormones, and others. In certain disease conditions, these essential components are being passed into the urine instead of being reabsorbed back into a patient's blood.

In certain further embodiments, the device may be also adopted for delivering therapeutically effective amounts of therapeutic agents, such as medicines (e.g., anti-coagulant, immunomodulator agents, or the like), hormones, growth factors, etc. directly into the blood stream or body fluid of the patient.

In certain embodiments, referring to FIGS. 19 and 23, the patient interface 3 of the described apparatus 100 may also include an anchoring element (not shown), which anchors the device to an inner surface of a tube that circulates bodily fluids, such as blood extracorporeally and forms an "extracorporeal circuit" 13. The term "extracorporeal circuit" means any tube or conduit outside the body that may be connected to the circulatory system or body fluid compartment in a mammal and provides for the flow of bodily fluid, such as blood or fluid through the tube or conduit by natural (e.g., heart) or artificial (e.g., mechanical pump) circulation. In certain embodiments, the housing 1 of the described device is being coupled with the extracorporeal circuit.

The term "anchoring element" refers to a structure that may be inserted into the lumen of an extracorporeal circulatory system blood tube or conduit and that, once inserted, may be anchored, for example, by hooks, barbs, or stents, to an inner surface of the tube or conduit. In an exemplary embodiment, the anchoring element may be a blood clot filter-type structure. A variety of blood clot anti-migration filters are known in the art. One example of an anchoring element is an anti-migration filter known as a "Greenfield® vena cava filter". Useful Greenfield® vena cava filters are described in detail in U.S. Pat. Nos. 4,817,600 and 5,059,205, the entire disclosures of which are incorporated herein by reference.

In certain further embodiments, referring to FIGS. 19 and 20, the described apparatus 100 may include a porous barrier 16 between the tissue construct and the bodily fluid present when in use. For example, the porous barrier 16 may be a filter 17, such as a hemofilter, that produces an ultrafiltrate.

In certain embodiments, the device 100 may include a semi-permeable membrane filter with pores, preferably of a size sufficient to permit the diffusion of essential components and cell products there through but yet small enough to exclude the passage of cells there through. The pores preferably are designed to permit the essential components produced or reabsorbed by the cells to diffuse directly into the blood stream, preventing the cells from migrating out of the tissue construct and into the systemic circulation.

In certain alternative embodiments, the device includes a cellular filter.

In certain embodiments, the apparatus is adapted to remove the immunogens from the bodily fluids before returning a filtrate to the patient's bodily fluids.

In certain further embodiments, the described apparatus 100 may also include at least one pump 18 (FIGS. 19 and 23) to simulate patient's blood pressure and flow rates.

Devices of increased complexity are also disclosed, whereby cells in the extratubular space can also mediate exchange or modulate the immune system. For instance, encapsulation of beta islets, organoids, follicular cells, or general cell spheroids, in, around, or near epithelialized or endothelialized tubules can mediate exchange. In some embodiments, the biocompatible and living components in the device may constitute an implantable therapeutic either with or without an outer casing.

In certain further embodiments, the described device 100 is capable of housing organoids 31 that hook cellularly into an arterial flow (top large tubes in FIG. 2) and collecting duct 10 and vasculature 7 below that drain into a collection bag and the renal vein (not shown), respectively. This device 100 is capable of both filtration and resorption. This device 100 can be extracorporeal in early embodiments, but has the capability to be implanted both, with or without a hard outer casing.

In certain embodiment, referring to FIGS. 19 and 23, the tissue construct 2 may be a tissue construct having an interpenetrating vascular network integrated with a cellular glomerular filtration unit and a patient interface device, 11 (e.g., a microfluidic platform). Importantly, fluid can flow between compartments of the device and can be driven by pumps, heart pressure, air pressure, or gravity flow.

The term "integrated with" means next to or nearby, such that fluid exchange is possible from cells in the vascular network to and from cells in the glomerular or epithelial network, either through a purely fluids interface, through a porous gel, or through a porous mesh of any type. In certain embodiments, the glomerular cells can also be sitting on top of, next to, nearby, or inside of vascular cells lining microfluidic devices, membranes or channels inside those devices.

The term "microfluidic platform" refers to any platform whereby media, blood, or any other biological fluids can be perfused through the platform using any type of pump, gravity fed pressures, or air pressure systems to control the flow.

An exemplary tissue construct having an interpenetrating vascular network integrated with a cellular glomerular filter on a microfluidic platform as well as method of producing the same is described in more detail in Example 2 below and schematically shown in FIG. 19.

In certain embodiments, the cellular glomerular filtration unit may include iPSC-derived intermediate mesoderm cells.

In certain other embodiments, the cellular glomerular filtration unit may include iPSC-derived podocytes.

The described device may be used in treatment of various diseases and conditions or in disease modeling of various conditions.

In certain embodiments, the described device can be used for renal replacement or assist therapy. For example, epithelial tubules and endothelial tubules, or open channels in a biomaterial matrix, may be placed in close proximity (between about 2 μm and about 500 μm). Urine from the ureter or from a patient's excreted waste may be perfused through the proximal tubules in the device. Essential components passed in the urine that patients lose in diseases, such as Fanconi's Syndrome would be resorbed by the proximal tubules in our device and transferred via the vasculature or basal-side access tubules back to the blood.

FIG. 1 shows an exemplary device 100, where the proximal tubules are in close proximity to blood vessels and perfused through a manifold system (not shown).

Certain further embodiments relate to an apparatus for use in connection with renal replacement or assist therapy in a patient in need of renal replacement or assist therapy. The apparatus 100 includes a housing 1 defining an interior space; a programmable mammalian tissue construct 2 disposed in the housing 1, and a patient interface 3 for communication of fluid between the patient and the tissue construct 2 disposed in the housing 1. In this embodiment, the tissue construct can include a plurality of proximal epithelial tubules, a plurality of endothelial tubules, and, optionally, a biocompatible material, in a form of e.g., a liquid, gel, paste, or a matrix (e.g., extracellular matrix material including, e.g., comprises one or more of gelatin, gelma, fibrin, matrigel, collagens, alginate, PEG hydrogels, hyaluronic acid, and gelatin methacrylate); wherein the epithelial tubules and endothelial tubules are in a close proximity to each other, and at least partially surrounded by the extracellular matrix material; the proximal epithelial tubules are adapted for and capable of resorption of at least one essential component of the patient's bodily fluid excreted due to a disease or dysfunction of the patient's kidney, and transfer of the resorbed at least one essential component or cell product back to the patient's bodily fluid; and the proximal epithelial tubules and the endothelial tubules are capable of production, secretion, and transfer of at least one of the same or another essential component or cell product into the patient's bodily fluid. The tissue construct may further include a plurality of capillaries of glomerulus or other structural elements of the kidney.

For example, the described device may be used for treatment of Fanconi syndrome or Fanconi's syndrome, which is a syndrome of inadequate reabsorption in the proximal renal tubules of the kidney. The syndrome can be caused by various underlying congenital or acquired diseases, by toxicity (for example, from toxic heavy metals), or by adverse drug reactions. It results in various small molecules of metabolism being passed into the urine instead of being reabsorbed from the tubular fluid (for example, glucose, amino acids, uric acid, phosphate, and bicarbonate). Fanconi syndrome affects the proximal tubules, namely, the proximal convoluted tubule (PCT), which is the first part of the tubule to process fluid after it is filtered through the glomerulus, and the proximal straight tubule (pars recta), which leads to the descending limb of the loop of Henle.

Different forms of Fanconi syndrome can affect different functions of the proximal tubule, and result in different complications. The loss of bicarbonate results in type 2 or proximal renal tubular acidosis. The loss of phosphate results in the bone diseases rickets and osteomalacia (even with adequate vitamin D and calcium levels), because phosphate is necessary for bone development in children and even for ongoing bone metabolism in adults.

Certain other embodiments relate to using the described device for liver assistance (incorporating hepatic organoids), insulin production (beta islet incorporation), or hormone production (parathyroid or thymus components).

Certain further embodiments relate to a method for the extracorporeal extraction of toxic material from mammalian body fluids in connection with diagnosis or treatment of a mammalian condition or disease in the patient, wherein the toxic material is completely or partially cleared from the blood circulation by passing the mammalian blood or plasma through the described apparatus.

Certain further embodiments relate to a method of treating a patient in need of organ replacement or organ assist, comprising: (a) providing the described apparatus having an extracorporeal circuit adapted for bodily fluid exchange between the patient and the apparatus: (b) passing bodily fluid withdrawn from the patient through the apparatus thereby re-conditioning the bodily fluid; and (c) reinserting the withdrawn bodily fluid as the re-conditioned bodily fluid back into the patient's body; thereby treating the patient in need of organ replacement or organ assist.

Certain further embodiments relate to a method of treating a patient in need of organ replacement or organ assist, comprising: (a) implanting into the patient the described apparatus adapted for bodily fluid exchange between the patient and the apparatus; (b) passing bodily fluid from the patient through the apparatus thereby re-conditioning the bodily fluid; and (c) returning to the patient the re-conditioned bodily fluid; thereby treating the patient in need of organ replacement or organ assist. The term "reconditioned bodily fluid" refers to the bodily fluid that has been treated by the described device having organ-level functions, such as filtration, reabsorption, metabolism, concentrating, excretion, composition modification, conditioning, or immune modulation, or any other organ function.

In certain embodiments, the device may be adapted for self-treatment, objectively analyzing the results, logging the data to a local or central storage unit, and providing a comprehensive interface for the patient and healthcare professional to analyze and observe results and correlate these results with progress within a therapy program. Such self-treating may be according to a protocol that is monitored and altered in real time to adapt to specific circumstances of the patient's needs.

Certain further embodiments relate to a method of making an apparatus for use in connection with organ replacement or organ assist therapy in a patient. The method includes (a) providing a housing defining an interior cavity; (b) disposing a programmable tissue construct in the housing; and (c) providing a patient interface for communication of fluids between the patient and the tissue construct disposed in the housing. The tissue construct is adapted for and capable of at least one of the following when in use: organ-like function selected from one or more of filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; or production, secretion, and transfer of at least one of the same or another essential component or cell product into the patient's bodily fluid In certain embodiments, the step of disposing an artificially-derived mammalian tissue construct in the housing is by the printing and can comprise depositing one or more cell-laden filaments each comprising a plurality of viable cells to form one or more tissue patterns, each of the tissue patterns comprising one or more predetermined cell types; depositing one or more sacrificial filaments to form a vascular pattern interpenetrating the one or more tissue patterns, each of the sacrificial filaments comprising a fugitive ink; optionally, at least partially surrounding the one or more tissue patterns and the vascular pattern with an extracellular matrix composition, and removing the fugitive ink to create vascular channels in the extracellular matrix composition, thereby forming an interpenetrating vascular network in a tissue construct.

In an alternative embodiment, the channels can be molded, e.g., arrays of fibers or pins can be created, where after the matrix is cast, the pins are removed.

In certain embodiments, a substrate may be used to deposit the tissue construct components; in alternative embodiments, a substrate-free method incorporating embedded-printing may be used. Other methods of deposing a programmable mammalian tissue construct in the housing are also contemplated. For example, the step of disposing a programmable mammalian tissue construct in the housing may be by using a pin pull-out to create both the vascular and epithelial networks. Some alternative methods of printing three-dimensional living organs, producing organoids, embryoid bodies, endothelial sprouts, with or without embedded vasculature were previously described in PCT Pub. No. WO 2015/069619 and its corresponding U.S. patent application Ser. No. 15/146,613, filed May 4, 2016; Application No. PCT/US2016/030710, filed May 4, 2016, entitled "Tubular Tissue Construct and a Method of Printing;" U.S. Prov. Application 62/294,118, filed Feb. 11, 2016, entitled "Mixed Population Organoids and Methods of Producing the Same," which are all incorporated by reference in their entirety. In certain embodiments, the plurality of viable cells are patient-derived cells or from allogenic sources (e.g., engineered iPSCs). The patient derived cells include, but are not limited to at least one of renal proximal tubule cells, loop of Henle cells, renal distal tubule cells, collecting duct cells, mesangial cells, renal microvascular cells, renal cell progenitors, pluri or multipotent stem cells, other endothelial lineage cells, endothelial cells, fenestrated glomerular endothelial cells, or iPSCs-derived patent-specific cell lines.

The tissue construct may be selected from the group consisting of viable cells, organoids, embryoid bodies, endothelial sprouts, autologous tissue, allogeneic tissue, xenogeneic tissue, and a tree-dimensional-printed tissue constructs. The tissue construct may comprise embedded vasculature. The tissue construct may be a tubular tissue construct, such as a nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

Certain further embodiment relate to a method of making an apparatus configured to be implanted into a patient's body for use in connection with organ replacement or organ assist therapy in the patient. The method includes transplanting into the patient in vivo completely living organ/tissue construct. In this embodiment, the organ/tissue construct may be created in vitro, matured in an apparatus as described herein, and then implanted it in vivo. In certain embodiments, the organ/tissue construct 2 may be implanted with the housing 1. In alternative embodiments, the organ may be transplanted without the housing. In either case, the organ/tissue construct is capable of replacing any organ functions. The method comprises: (a) providing a housing defining an interior cavity; (b) disposing a programmable mammalian, living tissue construct comprising viable cells into the housing; (c) providing a patient interface for communication of fluids between the patient and the tissue construct disposed in the housing; and (d) implanting the apparatus into the patient's body. The tissue construct is adapted for and capable of at least one of the following when in use: (i) organ-like function selected from one or more of filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; or (ii) production, secretion, and transfer of at least one of the same or another essential component or cell product into the patient's bodily fluid.

In certain embodiments, the tissue construct may be created in vitro prior to disposing into the housing. The tissue construct may be allowed to mature in vitro prior to disposing into the housing.

In certain embodiments, the tissue construct is disposed into the housing by printing the tissue construct with embedded vasculature 9 (FIGS. 1, 2, 17A-C, 19, 20, and 22 show tissue constructs with embedded vasculature) as described above.

In certain embodiments, by combining iPSC directed differentiation techniques, microfluidics, and 3D bioprinting, the tissue construct may include an interconnected 3D glomerulus and proximal tubule models that exhibit renal filtration and reabsorption at the macroscopic scale (Example 2).

Certain further embodiments relate to a manufacturing method to construct densely packed, perfusable vascular and proximal tubules that are circumscribed by confluent endo- and epithelium, respectively, and embedded within extracellular matrices that contain podocytes or other cells of interest.

The devices and methods described herein are applicable to kidney research, drug development, and disease modeling at both the cell- and physiological scales. Importantly, the devices and methods described herein provide a foundational step to building extracorporeal living medical devices for replacing both filtration and reabsorptive kidney functions.

Incorporated by reference in their entirety are the following patent documents and patent publications: U.S. Pat. Nos. 6,582,955; 5,741,334; 6,561,997; 6,913,588; 7,048,856; 7,540,963; 8,048,419; U.S. Pat. Pub. Nos. 2008/0112995; 2006/0286078; 2003/0118559; 2004/0024342; 2004/0124147; 2006/0213836; 2007/0269489; and PCT Pub. Nos. WO 2006/138537; WO 2003/020104; WO 2000/064510; WO 2004/024300; and WO 2007,092735.

EXAMPLES

Example 1

Engineering human tissues, and ultimately organs, that recapitulate native function for use in drug screening, disease modeling, and regenerative medicine is a grand challenge. Incidence rates of chronic and acute kidney injury are spiking due to increased use of prescription drugs[1,2,3]. Although roughly 25% of acute renal failure observed in the clinic is drug induced[2], predicting nephrotoxicity in preclinical in vitro or animal studies remains difficult. In fact, renal toxicity accounts for only 2% of failures in preclinical drug testing, yet it is responsible for nearly 20% of failures in Phase III clinical trials[3,4,5]. Hence, there is a critical need for improved kidney tissue models that can both predict human drug toxicity in longitudinal preclinical testing and serve as a modular building block for engineering human nephrons and, ultimately, kidneys.

While renal injury can occur in many locations, including the renal vascular network, glomerulus, tubulointerstitium, and collecting ducts, the convoluted proximal tubule (PT) is the site most frequently damaged (FIG. 3(A))[1]. The PT is responsible for 65-80% of nutrient absorption and transport from the renal filtrate to the blood, and thus, circulating drugs and their metabolites often accumulate in the PT at high concentrations in both intra- and intercellular spaces. Unfortunately, compared to their in vivo counterparts, proximal tubule cells grown in traditional 2D cell culture often lack, or rapidly lose, key phenotypic and functional aspects such as cell polarity, apical brush border, and significant receptor-mediated transport, hindering accurate longitudinal predictions of in vivo nephrotoxicity[6]. In vitro models that recapitulate the in vivo phenotype and function of proximal tubule cells could lead to more predictive nephrotoxicity models.

Towards this objective, several kidney PT models have been developed[7]. Proximal tubule cells have been cultured on biomimetic basement membrane coatings or on hollow fibers[8,9,10,11], improving their proliferation and ability to self-organize and maintain a differentiated state[12,13,14].

Researchers have also attempted to recreate the complex 3D microenvironments of the kidney. For example, differentiated proximal tubule cells have been shown to assemble into 3D structures within thin gels[15,16], and, more recently, induced pluripotent stem cell-derived kidney organoids have been created that contain various nephronal features[17,18,19,20,21]. While the emerging tissue complexity is compelling, kidney organoids are limited to roughly one millimeter in size and lack addressable inlet and outlets. Hence, proximal tubules within these organoids cannot be directly probed, nor can their perfusate be easily collected and analyzed. To date, perfusion has only been achieved within kidney-on-a-chip devices, which consist of a single layer of proximal tubule cells seeded on a porous membrane[22]. Despite their planar arrangement, the proximal tubule cells in these devices are subjected to a controlled shear stress environment[23] that significantly enhances their differentiated state as well as their response to nephrotoxic drugs. However, each of these existing models lack one or more characteristic features, i.e., 3D convolution, open luminal architecture, perfusion at physiological shear stresses, and longevity[7,24], required to achieve a truly biomimetic PT model.

One emerging approach suitable for producing complex, luminal tissue architectures is 3D bioprinting, which we originally developed for vascularized human tissues[25,26]. Here, we report a method that combines bioprinting, 3D cell culture, and organ-on-a-chip concepts to create a 3D convoluted renal proximal tubule (PT) composed of a perfusable open lumen that possesses a programmable architecture, which can support extratubular cellular heterogeneity. These 3D convoluted PTs consist of an open lumen architecture circumscribed by proximal tubule epithelial cells (PTECs), embedded in an extracellular matrix, and housed within a perfusable tissue chip, where they are subjected to physiological shear stresses. PTECs form a confluent epithelial monolayer that exhibits primary cilia and expresses $Na^+/K^+$ ATPase, Aquaporin 1 (AQP1), and K cadherin. Furthermore, cytokines produced by PTECs can be analyzed by collecting tubule perfusate. The unique combination of their 3D geometry and controlled perfusion gives rise to a more differentiated, polarized PTEC phenotype that develops an enhanced brush border, basement membrane protein deposition, basolateral interdigitations, enhanced cell height, megalin expression, and albumin uptake relative to both perfused and non-perfused 2D controls. The effects of the nephrotoxin, cyclosporine A, are analyzed by directly imaging as well as quantifying the diffusional permeability of the epithelium. To our knowledge, this is the first demonstration of bioprinted 3D convoluted proximal tubules with an addressable open lumen that can be maintained longitudinally.

Methods

Extracellular Matrix Preparation and Rheology

The ECM is comprised of a network of gelatin and fibrin. To prepare the ECM components, a 15 wt/v % gelatin solution (Type A, 300 bloom from porcine skin, Sigma) is first produced by adding gelatin powder to a warm solution (70° C.) of DPBS (1× Dulbelco's phosphate buffered saline without calcium and magnesium). The gelatin is allowed to fully dissolve by stirring for 12 h at 70° C., and the pH is then adjusted to 7.5 using 1 M NaOH. The solution is sterile filtered and stored at 4° C. in aliquots for later usage in casting (<3 months). A fibrinogen solution (50 mg/mL) is produced by dissolving lyophilized bovine blood plasma protein (Millipore) at 37° C. in sterile DPBS without calcium and magnesium. The solution is held at 37° C. without agitation for at least 45 min to allow complete dissolution.

The transglutaminase (TG) solution (60 mg/mL) is prepared by dissolving lyophilized powder (Moo Gloo) in DPBS without calcium and magnesium and gently mixing for 20 sec. The solution is then held at 37° C. for 20 min and sterile filtered before using. A $CaCl_2$ stock solution (250 mM) is prepared by dissolving $CaCl_2$ powder in DPBS without calcium and magnesium (Corning). To prepare stock solution of thrombin, lyophilized thrombin (Sigma Aldrich) is reconstituted at 500 U/mL using sterile DPBS and stored at −20° C. Thrombin aliquots are thawed immediately prior to use.

A controlled stress rheometer (DHR-3, TA Instruments, New Castle, Del.) with a 40 mm diameter, 2° cone and plate geometry is used for ink rheology measurements. The shear storage (G') and loss (G") moduli are measured at a frequency of 1 Hz and an oscillatory strain (γ) of 0.01. Time sweeps are conducted by rapidly placing a premixed ECM solution that contains thrombin onto the Peltier plate held at 37° C.

Ink Formulations

Two inks are required for 3D bioprinting of perfusable PT models. One ink, which is used to create the perfusion chip gasket, is composed of a two-part silicone elastomer (SE 1700, DOW Chemical) with a 10:1 base to catalyst (by weight) that is homogenized using a centrifugal mixer for 2 min (2000 rpm, AE-310, Thinky Corp, Japan). The silicone ink is printed within 2 h of mixing with catalyst. This ink is loaded in a syringe (EFD Inc., East Providence, R.I.) and centrifuged to remove any air bubbles before printing at room temperature. The other ink, a fugitive ink used to print the tubule, is composed of 38 wt % Pluronic F127 (Sigma) and 100 U/mL thrombin in deionized, ultrafiltrated (DIUF) water. The fugitive ink is dyed pink through the addition of a Risk Reactor dye for visualization in FIG. 3. To prepare this ink, a 40 wt % Pluronic F127 solution in water is homogenized using a Thinky mixer until the powder is fully dissolved, and subsequently stored at 4° C. Prior to use, a 2000 U/mL thrombin solution is added to the fugitive (Pluronic) ink at a ratio of 1:20, and homogenized using a Thinky mixer. The fugitive ink is then loaded in a syringe (EFD Inc., East Providence, R.I.) at 4° C. and centrifuged to remove any air bubbles. Before printing, this ink is equilibrated at room temperature for at least 15 min.

Bioprinting of Perfusable 3D Proximal Tubule Constructs

3D PT constructs are fabricated using a custom-designed, multimaterial 3D bioprinter equipped with four independently addressable printheads mounted onto a 3-axis, motion-controlled gantry with a build volume of 725 mm×650 mm×125 mm (AGB 10000, Aerotech Inc., Pittsburgh, Pa. USA). Inks are housed in separate syringe barrels to which nozzles of varying size (i.e., 50 mm-4101 m diameter) are attached via a luer-lock (EFD Inc., East Providence, R.I., USA). Inks are extruded through deposition nozzles by applying air pressure (800 Ultra dispensing system, EFD Inc., East Providence, R.I., USA), ranging from 10-90 psi, corresponding to print speeds between 1 mm/s and 5 cm/s. We first print the customized perfusion chip gasket by depositing the silicone ink through a tapered 410 mm nozzle onto 50 mm×75 mm glass slides. The gasket design is created using a custom MATLAB script that generates G-code for a final gasket structure. After printing, the perfusion chip gasket is cured at 80° C. in an oven for >1 h and stored at room temperature prior to use.

Patterning 3D PTs within the perfusion chip requires a combination of casting the ECM and printing the fugitive ink. First, the ECM solution is created by combining 10 mg/mL fibrinogen, 7.5 wt % gelatin, 2.5 mM $CaCl_2$ and 0.2 wt % TG. This solution is then equilibrated at 37° C. for 15-20 min before use to improve optical clarity of the ECM[25]. Next, the solution is rapidly mixed with thrombin at a ratio of 500:1, resulting in a final thrombin concentration of 1 U/mL. Within 2 min at 37° C., polymerization of fibrinogen into fibrin gel ensues. For this reason, the ECM solution must be cast onto the base of the perfusion chip immediately after mixing with thrombin. The base ECM layer is then allowed to dry slightly under nitrogen, such that it forms a flat surface. The fugitive Pluronic F127 ink (with 100 U/mL thrombin) is printed on the base ECM layer in the form of a convoluted filament (tubule) using a tapered 200/m nozzle. A custom Python script (MeCode) is used to specify the toolpath in G-code. Directly after fugitive ink printing, metal hollow perfusion pins interfaced through the silicone gasket are brought into contact with the printed ink. A top layer of ECM is then formed by casting the ECM solution over the printed tubule, as described above, to within 1-2 mm of the height of the gasket walls. If cells, such as HNDFs, are incorporated in the ECM (FIG. 12), they are mixed in directly after the equilibration period, prior to thrombin mixing and subsequent casting. After the top ECM layer is cast, the construct is covered with a glass slide to prevent evaporation or contamination and is held at 37° C. for 1 h to allow fibrin polymerization to terminate and TG to crosslink the network. The construct is then cooled to 4° C. for 15-20 min to liquefy the printed fugitive ink, which is flushed out of the device using cold cell media, leaving behind open conduits that serve as the desired tubular network embedded within the ECM with or without cells in the extratubular ECM space.

Using this method, we also produced 3D architectures in a layer-by-layer build sequence. For example, each individual layer of the three-layer structure shown in FIG. 16 has been constructed using a modified printing protocol that incorporates the materials and methods previously discussed. After printing the first tubules with fugitive ink, a layer of ECM is cast over the print and permitted 20 min to gel at 37° C. before the next proximal tubule layer is printed with fugitive ink on top of the recently gelled layer. This successive construction introduces 3D geometry and permits successful evacuation of all channels independently after construction. Aqueous-based risk reactor dyes are perfused through the channels and excited with UV light for visualization.

To complete the 3D tissue chip assembly process, each PT construct is placed onto a machined stainless steel base and a thick acrylic lid is placed on top. The lid and base are clamped together by four screws, forming a seal around the printed silicone gasket. Next, sterile two-stop peristaltic tubing (PharMed BPT, 0.25 mm internal diameter) is filled with media and connected to the outlet of a sterile filter that is attached to a 10 ml syringe barrel (EFD Nordson), which serves as a media reservoir. PTEC media (designed for growth, so ATCC formulation plus 1% FBS, 1% aprotinin, and 1% anti-anti) that has been equilibrating for >3 h in an incubator at 37° C., 5% $CO_2$ is added to the media reservoir, and tubing from the reservoir is connected to the outlet of the chip (metal hollow perfusion pin). A syringe is then used to exert slight pressure on the media in the barrel, forcing it to enter and completely fill the attached tubing. Filling the tubing with media prior to connecting it to the circuit prevents the introduction of air bubbles into the system. To complete the perfusion circuit, silicone tubing from the reservoir is connected to the inlet metal perfusion pin on the chip. Hose pinch-off clamps are added at the inlet and outlet of the perfusion chip to prevent uncontrolled flow when disconnected from the peristaltic pump, which can damage the epithelium or permit air bubbles to enter the system. The media reservoir is equilibrated with atmospheric conditions in the incubator at all times by means of a sterile filter on top of the media reservoir.

Cell Culture

Human immortalized PTECs (RPTEC/TERT1, ATCC CRL-4031) are cultured per ATCC's instructions and are used for all PT model studies up to passage 20. For gene expression analysis, human primary RPTEC (Cell Science), immortalized PTECs (RPTEC-TERT1, Evercyte) and A498 (ATCC HTB-44) renal cancer cells are used and cultured per supplier's instructions. Human neonatal dermal fibroblasts (HNDF), GFP expressing (Angio-Proteomie) are cultured per supplier's instructions and used up to passage 15.

Gene Expression Analysis

Human primary RPTEC (Cell Science), immortalized RPTEC-TERT1 (Evercyte) and A498 (ATCC HTB-44) renal cancer cells are grown in 96-well plates according to supplier's instructions and collected at Day 3 post-confluency by replacing culture medium with 100 μl/well of 1×RNA lysis mixture (QuantiGene Sample Processing Kit, QS0101). Then 40/l of lysate is mixed with an mRNA-capture magnetic bead set (Panomics QuantiGene Plex Set 12631, catalog number 312631), incubated overnight, processed for branched DNA amplification, and analyzed according to the manufacturer's instructions (Panomics QuantiGene Plex Assay kit, QP1015). The PPIB probe is used as a housekeeping gene for normalization. Fluorescence Intensity (FI) data are presented as average and standard deviation of 3 biological replicates.

Cytokine Analysis of Media Perfusate

Media perfusate is collected from a tubule over a period of 25 days post cell seeding and stored at −80° C. prior to analysis. For cytokine profiling, supernatants are thawed on ice, diluted 2× in sample dilution buffer (BioRad catalog #M60-009RDPD) and analyzed by Luminex technology-based ELISA using the Bio-Plex Pro™ Human Chemokine IL-6 (Set #171BK29MR2), IL-8 (Set #171-BK31MR2) and MCP-1 (Set #171-BK36MR2) and the Bio-Plex 200 Systems (BioRad) according to the manufacturer's instructions. Data are reported as average cytokine concentrations and standard deviations of technical triplicates.

Epithelialization and Longitudinal Culture

Each 3D PT construct is perfused for several hours with PTEC media in the incubator prior to cell loading/seeding. PTECs (PTEC/TERT1, ATCC) are trypsinized from their culture dish and concentrated in media to ~2×10$^7$ cells/mL. The cell suspension is then loaded into the perfusion chip through the outlet (FIGS. 10, B and C). The loaded construct is placed laterally in the incubator for several hours and flipped 180° over the course of multiple half-hour intervals to allow for uniform seeding of the tubule walls, then incubated in the tubule with no flow overnight. The next day, non-adherent cells are flushed out of the tubule under flow by gravity. Perfusion of fresh media is then started and the remaining cells begin to cluster and then grow from those colonies (FIG. 10F) until they reach confluency at around 3 weeks post seeding (FIG. 10K). During the growth phase, PTECs are fed PTEC media prepared per ATCC guidelines plus 1% aprotinin (EMD Millipore, used to slow down the degradation of the ECM), 1% fetal bovine serum (FBS), and 1% antibiotic-antimycotic (Gibco). After maturation, FBS is removed, and PTECs pack into a tight epithelial monolayer (Movie S2). At Day 1 post-seeding, the PTECs are exposed to continuous, unidirectional flow at 1.1/min, equating to shear stresses that vary between 0.1 and 0.5 dynes/cm$^2$ depending on the tubule cross section. Media is fed via a peristaltic pump in a closed loop circuit and changed every 2 days.

Albumin Uptake Study

Albumin uptake is assessed for the printed 3D PT models as well as 2D controls. The first control consists of PTECs grown on tissue culture plastic, while the second control consists of PTECs grown on our ECM. In each case, PTECs are grown to confluency and allowed to mature in serum free media. Human serum albumin conjugated with FITC (HSA-FITC, Abcam ab8030) is suspended in PTEC media at 501 g/mL. All samples are incubated with HSA-FITC in their media for 2 h (in the case of perfusion, it is perfused through the open lumen). After exposure, all samples are washed with 3× volume and then trypsinized with 10× trypsin to collect the individual cells. Cells are fixed and counterstained with primary and secondary antibodies for megalin (Table 2 lists the specific antibodies used; the list is non-limiting; many other stainings are possible and this is just a short list for preliminary characterization).

TABLE 2

Exemplary immunostaining reagents:

| Antibody or strain: | Source | Catalog # | Host Species & Reactivity | Concentration |
|---|---|---|---|---|
| Megalin | abcam | ab76969 | Rabbit anti-human | 1:300 |
| AQPI | Santa Cruz | SC25287 | Mouse anti-human | 1:300 |
| Na/K ATPase | abcam | ab76020 | Rabbit anti-human | 1:400 |
| Acetylated alpha tubulin | abcam | ab24610 | Mouse anti-human | 1:300 |
| Antibody to lamimin | abcam | ab11575 | Rabbit anti-human | 1:230 |
| K Cadherin | abcam | ab133632 | Rabbit anti-human | 1:200 |
| OCT2 | abcam | ab170871 | Rabbit anti-human | 1:300 |
| LTL | Vector Lab | B-1325 | N/A | 1:200 |
| ActinGreen | Life Technologies | R37110 | N/A | 2 drops per mL |
| NucBlue | Life Technologies | R37605 | N/A | 2 drops per mL |

Cells from those samples, and naked cells, are analyzed by flow cytometry (BD LSR Fortessa) and data is collected from n=10,000 cells per sample. To obtain images of HSA-FITC and megalin in PTECs, samples are fixed in place with formalin instead of being trypsinized after the wash step. Those samples are counterstained for megalin and imaged using confocal microscopy (Zeiss LSM710).

Cyclosporine A Testing

The effect of CysA on both 2D controls and bioprinted 3D PTs is explored. In 2D, cells are seeded in a 96-well format on tissue culture plastic and grown to confluency. They are fed media per ATCC's guidelines. CysA (Sigma-Aldrich, SML1018) is suspended in their media at various concentrations and incubated with cells for 24 h. A viability assay using (3-(4,5-dimethylthiazol-2-yl)-5-(3-carboxymethoxyphenyl)-2-(4-sulfophenyl)-2H-tetrazolium) in the presence of phenazine methosulfate (MTS) is run at the 24 h mark post exposure. This assay is completed on PTECs at early confluency, by giving CysA to the cells on the day they reached confluency, as well as late confluency, by giving CysA several days after they reached confluency. Notably, the toxicity results are similar for each case (FIG. 7N). For 3D PTs, CysA is fed at various concentrations through the open lumen of mature tubules after reaching confluency (at ~3 week mark), where no serum is included in the media for a minimum of 10 days. At the 24 h mark post CysA exposure, a FITC-dextran leak test (described below) is performed to assess and quantify perturbations to the barrier function of PTECs. Directly following, the PT is fixed using 10% buffered formalin for 1 h and counterstained for actin and DAPI (Table 2 lists the specific stains used).

Diffusional Permeability Measurements

To assess barrier function of the epithelium in 3D, diffusional permeability is quantified by perfusing PTEC media in the open lumen containing 25 og/mL FITC-conjugated 70 kDa dextran (FITC-Dex, Sigma product 46945) at a rate of 15 DL/min for 3 min and 1 iL/min thereafter for ~30-45 min. The entire test is performed under live cell imaging with both the tubule and the surrounding ECM in the field of view (FIG. 16). The diffusion pattern of FITC-Dex is detected using a wide-field fluorescent microscope (Zeiss Axiovert 40 CFL). Fluorescence images are captured before perfusion and every 3 to 5 min over a 30-45 min period. Diffusional permeability of FITC-Dex is calculated by quantifying changes in fluorescence intensity over time using the following equation[34];

$$P_d = \frac{1}{I_1 - I_b}\left(\frac{I_2 - I_1}{t}\right)\frac{d}{4}$$

$P_d$ is the diffusional permeability coefficient, $I_1$ is the average intensity at an initial time point, $I_2$ is an average intensity at t~30-45 min, $I_b$ is background intensity (image taken before perfusion of FITC-Dex), and d is the diameter of the channel. Other researchers have reported that PTECs can resorb dextran[39], which would lead to slightly higher values for the measured diffusional permeability.

We also investigated the barrier properties of our epithelial lined tubules using a low molecular weight compound, inulin (4.5 kDa) that is neither resorbed nor secreted in vivo by PTECs using the same method described above. Specifically, inulin-FITC (Sigma product F3272) is dissolved in warmed PTEC media at 100 bg/mL and perfused in the open lumen at a rate of 20 L/min for 3 min and 1.5 iL/min thereafter for ~15 min. The entire test is performed under live cell imaging with both the tubule and the surrounding ECM in the field of view (FIG. 14). The diffusion pattern of FITC-inulin is detected using a wide-field fluorescent microscope (Leica). Fluorescence images are captured with a gated light source and motion controlled stage before perfusion and every 3 to 5 min over the 15 min period to collect technical triplicate measurements.

Electron Microscopy

For transmission electron microscopy (TEM), PTECs in 2D or 3D architectures or healthy human kidney tissue obtained from a standard biopsy prior to transplant are fixed using 2.5% glutaraldehyde, 1.25% paraformaldehyde, and 0.03% picric acid in 0.1 M sodium cacodylate buffer (pH 7.4) for a minimum of several hours. Small samples (1 mm×1 mm) are removed and washed in 0.1 M cacodylate buffer and bathed in 1% osmiumtetroxide (OsO$_4$) (EMS) and 1.5% potassiumferrocyanide (KFeCN$_6$) (Sigma) for 1 h, washed in water 3× and incubated in 1% aqueous uranyl acetate (EMS) for 1 h followed by 2 washes in water and subsequent dehydration in varying grades of alcohol (10 min each; 50%, 70%, 90%, 2×10 min 100%). The samples are then put in propyleneoxide (EMS) for 1 h and incubated overnight in a 1:1 mixture of propyleneoxide and TAAB Epon (Marivac Canada Inc. St. Laurent, Canada). The following day the samples are embedded in TAAB Epon and polymerized at 60° C. for 48 h. Ultrathin sections (about 60 nm) are cut on a Reichert Ultracut-S microtome, placed on copper grids stained with lead citrate and examined in a JEOL 1200EX Transmission electron microscope and images are recorded with an AMT 2k CCD camera. Image analysis is performed using ImageJ software.

For scanning electron microscopy (SEM), perfused PTECs in 3D are fixed using 10% buffered formalin for 1 h. The samples are thinly sliced (~1 mm thick) to expose cells circumscribing the open lumen. The fixative is washed away using PBS×2 and subsequent dehydration in varying grades of ethanol (20 min each; 30%, 50%, 70%, 90%, 3×20 min 100%). The samples are then placed in 50% ethanol and 50% hexamethyldisilazane (HMDS) for 30 min followed by 100% HMDS 3×30 min. All steps are performed in a closed and sealed glass container. After the final washing with HMDS, the samples are removed and placed in an open container under N$_2$ in the fume hood to dry. Dried samples are mounted to aluminum pin mounts using conductive carbon tape, sputter coated with gold, and imaged with a Tescan Vega SEM.

Immunostaining

Immunostaining followed by confocal microscopy is used to assess the cellular localization of proteins in 2D and 3D PTEC models. Prior to immunostaining, each construct is washed with PBS and then fixed for 20 min to 1 h using 10% buffered formalin. The fixative is removed using several washes in PBS for several hours and then blocked overnight using 1 wt % bovine serum albumin (BSA) in PBS. Primary antibodies to the cell protein or biomarker of interest are incubated with the constructs for 1 day at the dilutions listed in Table 2 in a solution of 0.5 wt % BSA and 0.125 wt % Triton X-100. Removal of unbound primary antibodies is accomplished using a wash step against a solution of PBS or 0.5 wt % BSA and 0.125 wt % Triton X-100 in PBS for 1 day. Secondary antibodies are incubated with the constructs for 1 day at the dilutions listed in Table 2 in a solution of 0.5 wt % BSA and 0.125 wt % Triton X-100 in PBS. Samples are counter-stained with NucBlue or ActinGreen for 2 h and then washed for 1 day in PBS prior to imaging.

Image Rendering and Analysis

Phase contract microscopy is performed using an inverted Leica DM 1L scope with objectives ranging from 1.25× to 40×. Confocal microscopy is performed using an upright Zeiss LSM 710 with water immersion objectives ranging from 5× to 40× employing spectral lasers at 405, 488, 514, 561, and 633 nm wavelengths. Image reconstructions of z-stacks are performed in ImageJ using the z-projection function with the maximum pixel intensity setting. Any increases in brightness are performed uniformly across an entire z-projected image. 3D image reconstructions and rotating movies (Movie S3) are performed using Imaris software. The new CytoSMART (Lonza) in incubator system is used to capture time-lapse imaging (Movie S2). Image analysis for quantification of diffusional permeability is performed using custom MATLAB scripts employing previously reported methods[34]. TEM image analysis is performed using ImageJ software to measure cell height (n≥50), microvilli density (n≥25), and microvilli length (n≥150) over at least 3 independent samples for each condition.

Statistical Analysis

Data are expressed as means±standard deviation. Statistical analysis is performed using MATLAB and statistical significance is determined at a value of p<0.05 as determined by an ANOVA using Tukey's multiple pairwise comparison test. Different significance levels (p values) are indicated with asterisks and specific p values are provided in each figure legend.

Results

Printing, Seeding, and Longitudinal Culture of 3D Proximal Tubules on Chip

Our bioprinting method is used to construct a 3D convoluted proximal tubule segment of a nephron, as depicted in FIG. 3A. First, as shown in FIGS. 3B-C, a silicone gasket is printed on a glass slide that demarcates the outer border of the 3D tissue chip. A layer of engineered extracellular matrix (ECM), which is composed of a gelatin-fibrin hydrogel[25], is then evenly deposited within the gasket. Next, a fugitive ink, shown in pink, is printed onto the ECM layer. The term "fugitive ink" refers to a printed material that will ultimately be liquefied and removed from the final 3D PT construct. After printing, the fugitive ink is connected to hollow metal pins interfaced through the gasket walls and additional ECM is cast over the printed structure. The 3D tissue model is then housed within a perfusable chip, where it is cooled to 4° C. to liquefy and subsequently remove the fugitive ink yielding an open convoluted tubular channel embedded within the ECM. Finally, cell media is perfused through the 3D convoluted tubular architecture on chip via an external peristaltic pump. Notably, our method can create 3D proximal tubule models in myriad configurations with precisely controlled size, curvature, and location. For instance, if multiple tubules are required to increase statistical relevance of an assay or provide basal-side access channels, they can be printed alongside one another (FIG. 8) and either perfused independently or collectively through a single inlet.

The composition and rheological properties of the ECM and fugitive ink are specifically tailored for our biofabrication method. The ECM consists of fibrinogen, gelatin, and two enzymes (thrombin and transglutaminase)[25]. The dual enzyme scheme enables rapid solidification of the ECM around printed features, through thrombin action on fibrinogen to make fibrin. The second enzyme, transglutaminase, provides a slower crosslinking of gelatin with fibrin, enabling a seamless integration of the upper and lower ECM layers during assembly (FIG. 9A). Furthermore, the elastic modulus of the ECM (~3.5 kPa) mimics that of the cortex of a healthy kidney (~4 kPa)[27]; both matrix stiffness and composition are important for the retention of tissue-specific cell functionality[12,28]. The fugitive ink is composed of a triblock copolymer of polyethylene-polypropylene-polyethylene (Pluronic® F127), which forms a viscoelastic gel above a critical micelle concentration in water at room temperature. This ink exhibits a gel-to-fluid transition as the perfusable tissue chip is cooled to 4° C., enabling its removal from the ECM under those conditions[26,29]. The fugitive ink also contains a high concentration of thrombin (100 U/mL). Upon surrounding this ink with ECM during the casting process, soluble fibrinogen is rapidly transformed to insoluble fibrin, templating fibrin around the lumen and facilitating the desired, long-term perfusion of cell media.

Prior to introducing cells, we perfuse the 3D tissue chip with cell media overnight at 37° C. to remove any residual fugitive ink or enzymes and equilibrate the matrix at 37° C. and 5% $CO_2$ in the incubator. We then introduce PTEC-TERT1 cells that consist of human proximal tubular cells immortalized through stable expression of the catalytic subunit of human telomerase reverse transcriptase (TERT) [30]. PTEC-TERT1 were developed as a cell model that maintains morphological and functional properties of primary PTEC cells with an additional replicative advantage over primary cells that have a finite lifespan in vitro due to telomere shortening[16,30]. Genomic stability of PTEC-TERT1 up to 90 population doublings has been demonstrated[30]. We further profiled PTEC-TERT1 by carrying out gene expression analysis on 33 key PTEC genes and comparing them with primary PTEC and the renal cancer cell line A498 (FIG. 9B). The mRNA levels demonstrate that PTEC-TERT1 cells are transcriptionally close to primary renal PTEC cells. Given the need for scalable, stable cellular systems in drug discovery and safety platforms, we optimized our 3D PT model with PTEC-TERT1 (hereby referred to as PTECs).

To circumscribe the convoluted tubules with a confluent PTEC monolayer, the cells are first trypsinized from a tissue culture plastic dish, concentrated, and perfused into the open lumen of the printed structure. The cells incubate in the tubule overnight with no flow to facilitate adherence to the ECM and are then flushed lightly at Day 1 to remove any non-adherent cells. A time sequence of their maturation process in the tubule is provided (FIG. 10). Notably, PTECs grow to confluency within the tubule, circumscribing the open lumen in 3D over a period of approximately 3 weeks. Furthermore, since PTECs actively participate in pro-inflammatory cytokine production in vivo and in vitro[1,31], we measured the accumulation of IL6, IL-8 and MCP1 in the tubule perfusate over time. The cytokine profile shows distinct concentrations in the growth and maturation phase, suggesting the tubule stabilizes after confluency (FIG. 11). Moreover, the decrease of 11-6 concentration after serum removal is consistent with the previously reported inductive effect of albumin on IL-6 production in primary human PTECs[32].

For increasing levels of complexity, support cells, such as fibroblasts or immune cells, can be suspended in the ECM surrounding the printed tubules[25,26]. As shown in FIG. 12, fibroblasts can survive adjacent to the tubule in the extratubular space of the ECM. While tubule diameters ranging from 150 μm to 700 μm can be printed, we carried out assays and quantitative measurements on PTs with diameters ranging from 400 μm to 550 μm under a flow rate of ~1 μL/min. Images of a mature PT at low and higher magnifications (FIGS. 3D-F) reveal that PTECs circumscribe the lumen and adopt a cuboidal morphology, as expected for their in vivo phenotype. These engineered 3D convoluted PTs are maintained longitudinally by perfusing media in a closed-loop system. Media is replaced every two days and the tubules remain viable for extended periods; the longest period tested exceeds two months (65 days).

3D Proximal Tubules Form a Polarized Epithelium

Figure 3:
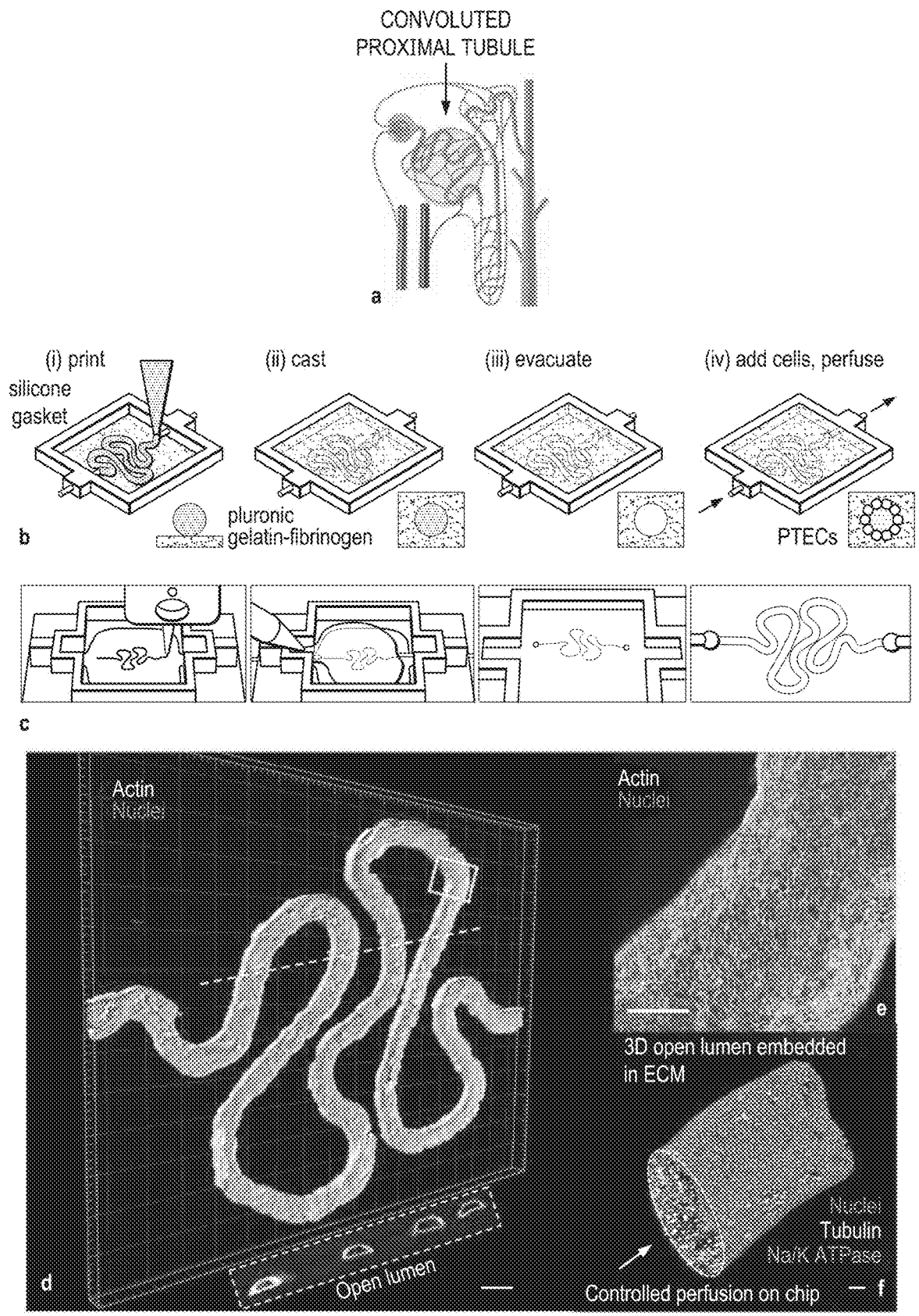
FIG. 3 depicts: (A) schematic of a nephron highlighting the convoluted proximal tubule, (B, C) corresponding schematics and images of different steps in the fabrication of 3D convoluted, perfusable proximal tubules, in which a fugitive ink is first printed on a gelatin-fibrinogen extracellular matrix (ECM) (i), additional ECM is cast around the printed feature (ii), the fugitive ink is evacuated to create an open tubule (iii), and PTEC cells are seeded within the tubule and perfused for long time periods (iv); (D) a 3D rendering of the printed convoluted proximal tubule acquired by confocal microscopy, where actin is stained in red and nuclei are blue.

After PTECs are seeded and grown to maturity in the tubule, a combination of light microscopy, scanning electron microscopy (SEM) and transmission electron microscopy (TEM) are used to characterize the printed and perfused 3D PT (FIGS. 2 and 3). Specifically, low (FIG. 4A) and high (FIG. 4B) magnification views in phase microscopy reveal that PTECs grow throughout the tubule packing together in a columnar fashion. TEM images of the tubule cross-section further show that PTECs assemble into a tightly packed, columnar renal tubular epithelium (FIGS. 4C-D). As shown schematically in FIG. 4E, native epithelium forms a basement membrane on the basal side and a brush border of microvilli on the apical side facing the open lumen with cells in a columnar morphology. From the TEM images, we quantified the increase in cell height, owing to the columnar cell morphology within the 3D proximal tubule (FIG. 4C) compared to the same cells grown for the same duration in 2D on ECM without perfusion (FIG. 4D). Importantly, the PTECs in our printed and perfused 3D PT constructs exhibit a two-fold increase in cell height relative to the planar controls without perfusion and a 40% increase relative to perfused 2D controls on our ECM (FIG. 4F). Moreover, the cell height of 14.1±2.4 µm observed in our 3D PT constructs approaches that found in healthy human proximal tubules (20.3±4.1 µm).

SEM images of the apical side of the 3D PT (FIG. 4G) reveal the formation of a confluent cell layer and the presence of primary cilia (one per cell, akin to that observed in vivo). The primary cilium is a sensory organelle that extends into the open lumen and responds to shear stress; it is important for the maintenance of the epithelial cell phenotype and is often lost once cells are isolated and cultured in 2D in the absence of shear stress[22]. Primary cilia are also observed in our PT using immunofluorescence, by staining for acetylated tubulin (shown in red in the 3D rendering in FIG. 2h and S6). Furthermore, we confirmed the expression of the epithelial marker Na$^+$/K$^+$ ATPase (FIGS. 4H-I), and its appropriate sub-cellular localization to the basolateral plasma membrane (FIG. 13A), which is again akin to the in vivo PTEC phenotype. The proximal tubule-specific (versus distal tubule) water channel Aquaporin 1 (AQP1) is also predominant throughout our tubule (FIG. 4J) and the AQP1 staining at higher magnification has a speckled pattern on the membrane surface (FIG. 4K) as others have shown[33]. We also observe proper apical expression of lotus tetragonolobus lectin (LTL) (FIG. 13C) and basal expression of organic cation transporter (OCT2) (FIG. 13D).

Cell polarity is a fundamental feature needed for vectorial transport. We explored PTEC polarity by first characterizing the apical side of our 3D PT using TEM (FIG. 5A). At the apical surface, microvilli are present and form a brush border that is more pronounced than in 2D (compare FIGS. 4C and 7A with FIG. 4D). At the basal (FIG. 5B) surface, basolateral interdigitations (BI) are prominent. These BI extend the surface area of the lateral and basal borders in vivo. By contrast, PTEC cells in the 2D controls (FIG. 4D) lack BI. The presence of circular invaginations in the lateral membrane, denoted by white arrows in FIG. 5B, suggest that mechanisms of active transport are present at the lateral surface. Furthermore, there is a distinct difference between the ECM morphology and basement membrane (BM) proteins deposited by the PTECs. Further exploration of the BM protein composition reveals that in mature 3D PT constructs, PTECs deposit laminin and collagen IV (FIG. 5C). Tight junctions between neighboring cells are observed (FIG. 5D) along with the presence of cell-cell junction proteins, such as K cadherin in FIG. 5E, that link cells in a characteristic cobblestone pattern. Lastly, properties of the brush border are quantified by image analysis. We find that the average microvilli length in the 3D printed and perfused PTs is ~200% longer than the 2D non-perfused and ~40% higher than the 2D perfused controls (FIG. 5F). Concurrently, microvilli density is also significantly higher for the printed and perfused 3D PT constructs compared to all 2D control conditions (all 2D controls are statistically similar) (FIG. 5G). Once again, the microvilli length (1.24±0.3 µm) and density (4.13±0.5 µm) observed in our 3D PT constructs is closer to that of healthy human proximal tubules, which are 2.89±0.6 µm and 7.81±1.0/µm, respectively.

PTECs should form near leak tight barriers against the traffic of certain proteins, like low molecular weight inulin, when healthy and confluent. To assess their barrier function[34], we perfused FITC-labeled inulin (4.5 kDa) through the open lumen of mature PTs and the measured dye intensity using a wide-field fluorescence scope as a function of time. From these data, we determined the diffusional permeability and compared this value to a control measurement carried out in a 3D tubule without epithelial lining (FIG. 14). We observed a dramatic reduction in the diffusional permeability coefficient (greater than an order of magnitude) between these two samples, indicating that the epithelial barrier in the printed and perfused 3D PT construct is tight and functional.

Albumin Uptake

Receptor-mediated endocytosis by PTEC cells is essential for body fluid homeostasis. Reabsorption of plasma proteins from the glomerular filtrate relies partially on the megalin-cubilin complex located in the brush borders[35,36,37] and can be modeled in vitro by monitoring albumin uptake by PTECs. We tested the ability of PTECs, grown either on perfused 3D PT constructs or 2D controls, to uptake FITC-labeled human serum albumin (HSA). After exposure to FITC-HSA for 2 h, PTECs are collected, stained for megalin expression, and analyzed by flow cytometry. The results for albumin uptake are provided in FIG. 6A. Large populations of cells in the 2D controls exhibit fluorescence intensity similar to the non-fluorescent control, whereas cells lining the perfused 3D PT constructs exhibit a significant increase in the FITC-HSA intensity. Results for megalin, one of the transporters for albumin, show that its expression is also highest in the 3D PT (FIG. 6B). Mean values for the fluorescence intensity of the populations analyzed by flow cytometry are provided below:

| Mean Intensity | Albumin | Megalin |
| --- | --- | --- |
| 2D on Plastic | 201 | 571 |
| 2D on Printing Matrix | 310 | 1127 |
| 3D Printed (Perfused) | 1452 | 1670 |

Contrary to the 2D controls, we find that enhanced megalin expression is strongly correlated with superior albumin functional uptake in the perfused 3D PTs, suggesting that both their 3D architecture and perfusion improve epithelial function likely due to enhanced cell polarity and brush border (FIG. 5). Lastly, images of FITC-HSA (FIG. 6C), megalin (FIG. 6D), and the combination thereof (FIG. 6E) reveal an overlapping distribution of albumin and megalin in PTECs that line the 3D PT. Thus, our engineered 3D PT constructs exhibit superior albumin uptake function relative to either 2D control.

Drug Toxicity Testing

Cyclosporine A, a drug commonly given following transplant surgery to prevent rejection, is a known nephrotoxin that damages proximal tubule cells. To study its effect on the perfused 3D PT model, we exposed them to various concentrations of Cyclosporine A (CysA) and monitored alterations of cell morphology and cytoskeleton organization by immunostaining of actin filaments. Bright field images of the tubules (FIGS. 7A-D) and corresponding 3D renderings of actin staining (FIGS. 7E-L) reveal dose-dependent manifestation of CysA-induced damage. Minor breaks in cell-cell junctions (FIG. 15) and reorganization of actin (FIG. 7J) are observed at 10 µM CysA, whereas discrete areas devoid of cells are readily evident at 50 µM CysA (FIGS. 7G, 7K) and those areas become more pronounced at 100 µM CysA (FIGS. 7D, 7H, 7L, and 20). We also note that cell layers tighten and buckle at 50 µM and 100 µM CysA (FIGS. 7G, 7K, FIG. 18, and FIG. 19). Finally, we assessed CysA-induced disruption of the epithelial barrier function by quantifying the diffusional permeability of FITC-dextran (70 kDa) in treated tubules (FIG. 16). As shown in FIG. 7M, exposure to 50 and 100 µM CysA increases the epithelial barrier permeability by almost 4-fold and 6-fold, respectively. We also find that the respective cell viability of PTECs grown on 2D culture plastic dishes decreases by 40% and 60% after treatment with 50 and 100 µM CysA (FIG. 7N). Overall, these results indicate that the 3D PT constructs can be used to qualitatively (immunostaining) and quantitatively (diffusional permeability measurements) assess nephrotoxicity.

Discussion

Recent advances in bioprinting enable the integration of pervasive and interconnected channels within engineered extracellular matrices[26,38]. We previously showed that these channels can be lined with endothelial cells and perfused to create tissues with embedded vasculature[25,26]. By combining bioprinting, 3D cell culture, and organ-on-chip methods, we demonstrate a customizable platform for fabricating perfusable, convoluted 3D proximal tubules on chip. Our ability to programmably define tubule size and geometry, including convolution, overcomes the limitations of pin pullout approaches that can only produce straight tubules in gels[31]. Our engineered ECM, which is based on enzymatic crosslinking of fibrinogen and gelatin[25], promotes improved adhesion of PTECs relative to prior matrices[23] allowing the cells to form a confluent layer that can be sustained for >60 days. This epithelium exhibits several morphological features and functional markers akin to native PTECs in vivo. Unlike kidney-on-a-chip devices based on cell monolayers[19,36], our perfusable 3D PTs enable collection of hundreds of thousands of cells for analysis, far greater than that required (~10,000 cells) for accurate sampling via flow cytometry.

Our 3D PT models can be used to elucidate mechanisms of drug-induced tubule damage, including weakening of cell-cell junctions, cell ejection from the monolayer, and cell death. In the future, we will investigate the morphology and function of PTECs seeded within printed 3D tubules whose diameter (~60 µm) and curvature more closely mimics in vivo PTs to determine whether further improvements to the epithelium structure and function can be achieved. We also envision creating more complex 3D kidney models, in which both multiple tubules and vascular networks are patterned alongside one another to facilitate basal side access and studies of interactions between adjacent channels (FIGS. S1 and S10). By incorporating multiple cells types in the extratubular space (FIG. 12), we can introduce additional complexity required for studying cell-cell interactions. Ultimately, we plan to explore seeding and maturation of iPSC-derived renal progenitors in our perfusable 3D PT constructs.

In summary, we have reported the fabrication and characterization of 3D convoluted renal proximal tubules embedded within an extracellular matrix on customized perfusion chips. These perfusable 3D PTs promote the formation of a tissue-like epithelium with improved phenotypic and functional properties relative to the same cells grown on 2D controls. Our bioprinting method opens new avenues for creating 3D organs-on-a-chip that better recapitulate in vivo microenvironments, which could enable advances in drug screening, mechanistic drug studies, disease models, and ultimately, regenerative medicine.

REFERENCES

1. Tiong, H. Y. et al. Drug-induced nephrotoxicity: clinical impact and preclinical in vitro models. Mol Pharm 11, 1933-1948, doi:10.10211mp400nOw (2014).
2. Deccloedt, E. Drug-induced renal injury. Continuing Medical Education 29, 252-255 (2011).
3. Choudhury, D. & Ahmed, Z. Drug-associated renal dysfunction and injury. Nat Clin Pract Nephrol 2, 80-91, doi:10.1038/ncpneph0076 (2006).
4. Naughton, C. A. Drug-induced nephrotoxicity. Am. Fam. Physician 78, 743-750 (2008).
5. Redfern, W. S. et al. Impact and prevalence of safety pharmacology-related toxicities throughout the pharmaceutical life cycle. J Pharmacol. Toxicol. Methods 62, e29, doi:http://dx.doi.org/IO.1016/j.vascn.2010.11.098 (2010).
6. Jenkinson, S. E. et al. The limitations of renal epithelial cell line HK-2 as a model of drug transporter expression and function in the proximal tubule. Pfluger'S Arch. 464, 601-611, doi:10.1007/s00424-012-1163-2 (2012).
7. Desrochers, T. M., Palma, E. & Kaplan, D. L. Tissue-engineered kidney disease models. Adv Drug Deliv Rev 69-70, 67-80, doi:10.1016/j.addr.2013.12.002 (2014).
8. Jansen, J. et al. Human proximal tubule epithelial cells cultured on hollow fibers: living membranes that actively transport organic cations. Scientific reports 5, 16702, doi:10.1038/srep16702 (2015).
9. Jansen, J. et al. Bioengineered kidney tubules efficiently excrete uremic toxins. Scientific reports 6, 26715, doi: 10.1038/srep26715 (2016).
10. Oo, Z. Y., Kandasamy, K., Tasnim, F. & Zink, D. A novel design of bioartificial kidneys with improved cell performance and haemocompatibility. J Cell Mol Med 17, 497-507, doi:10.11111jcmm.12029 (2013).
11. Schophuizen, C. M. et al. Development of a living membrane comprising a functional human renal proximal tubule cell monolayer on polyethersulfone polymeric membrane. Acta Biomater 14, 22-32, doi:10.1016/j.actbio.2014.12.002 (201S).
12. Jansen, J. et al. Biotechnological challenges of bioartificial kidney engineering. Biotechnol Adv 32, 1317-1327, doi:10.1016/j.biotechadv.2014.08.001 (2014).
13. Zhang, R., Tasnim, F., Ying, J. Y. & Zink, D. The impact of extracellular matrix coatings on the performance of human renal cells applied in bioartificial kidneys. Biomaterials 30, 2899-2911, doi:10.1016/j.biomaterials.2009.01.046 (2009).
14. Zhang, R. et al. Generation of easily accessible human kidney tubules on two-dimensional surfaces in vitro. J Cell Mol Med 15, 1287-1298, doi:10.11111j.1S82-4934.2010.01113.x (2011).
15. Guimaraes-Souza, N. K., Yamaleyeva, L. M., AbouShwareb, T., Atala, A. & Yoo, J. J. In vitro reconstitution of human kidney structures for renal cell therapy. Nephrol. Dial. Transplant. 27, 3082-3090, doi:10.1093/ndt/gfr78S (2012).
16. DesRochers, T. M., Suter, L., Roth, A. & Kaplan, D. L. Bioengineered 3D human kidney tissue, a platform for the determination of nephrotoxicity. *PLoS One* 8, eS9219, doi:10.13711joumal.pone.00S9219 (2013).
17. Takasato, M. et al. Directing human embryonic stem cell differentiation towards a renal lineage generates a self-organizing kidney. *Nat Cell Bioi* 16, 118-126, doi: 10.1038/ncb2894 (2014).
18. Takasato, M., Maier, B. & Little, M. H. Recreating kidney progenitors from pluripotent cells. *Pediatr. Nephrol.* 29, 543-552, doi:10.1007/s00467-013-2592-7 (2014).
19. Freedman, B. S. et al. Modelling kidney disease with CRISPR-mutant kidney organoids derived from human pluripotent epiblast spheroids. *Nat Commun* 6, 8715, doi:10.1038/ncomms9715 (2015).
20. Morizane, R. et al. Nephron organoids derived from human pluripotent stem cells model kidney development and injury. *Nat. Biotechnol.* 33, 1193-1200, doi:10.1038/nbt.3392 (2015).
21. Takasato, M. et al. Kidney organoids from human iPS cells contain multiple lineages and model human nephrogenesis. *Nature* 526, 564-568, doi:10.1038/nature15695 (2015).
22. Jang, K. J. et al. Human kidney proximal tubule-on-a-chip for drug transport and nephrotoxicity assessment. *Integrative biology: quantitative biosciences from nano to macro* 5, 1119-1129, doi:10.1039/c3ib40049b (2013).
23. Grabias, B. M. & Konstantopoulos, K. Epithelial-mesenchymal transition and fibrosis are mutually exclusive responses in shear-activated proximal tubular epithelial cells. *FASEB J* 26, 4131-4141, doi:10.1096/fj.12-207324 (2012).
24. Little, M. H. et al. Defining kidney biology to understand renal disease. Clinical journal of the American Society of Nephrology: CJASN9, 809-811, doi:10.2215/CJN.10851013 (2014).
25. Kolesky, D. B., Homan, K. A., Skylar-Scott, M. A. & Lewis, J. A. Three-dimensional bioprinting of thick vascularized tissues. *Proc. Natl. Acad. Sci. U S. A.* 113, 3179-3184, doi:10.1073/pnas.1521342113 (2016).
26. Kolesky, D. B. et al. 3D Bioprinting of Vascularized, Heterogeneous Cell-Laden Tissue Constructs. *Adv. Mater.* 26, 3124-3130, doi:10.1002/adma.201305506 (2014).
27. Bensamoun, S. F., Robert, L., Leclerc, G. E., Debernard, L. & Charleux, F. Stiffness imaging of the kidney and adjacent abdominal tissues measured simultaneously using magnetic resonance elastography. *Clin. Imaging* 35, 284-287, doi:10.1016/j.clinimag.2010.07.009 (2011).
28. Furness, P. N. Extracellular matrix and the kidney. *J Clin. Pathol.* 49, 355-359 (1996).
29. Wu, W., DeConinck, A. & Lewis, J. A. Omnidirectional printing of 3D microvascular networks. *Adv Mater* 23, H178-183, doi:10.1002/adma.201004625 (2011).
30. Wieser, M. et al. hTERT alone immortalizes epithelial cells of renal proximal tubules without changing their functional characteristics. *American journal of physiology. Renal physiology* 295, F1365-1375, doi:10.1152/ajprenal.90405.2008 (2008).
31. Adler, M. et al. A quantitative approach to screen for kidney toxic compounds in vitro. *J Am. Soc. Nephrol.* (2015).
32. Pearson, A. L., Colville-Nash, P., Kwan, J. T. & Dockrell, M. E. Albumin induces interleukin-6 release from primary human proximal tubule epithelial cells. *JNjournal of nephrology* 21, 887 (2008).
33. Hara-Chikuma, M. & Verkman, A. S. Aquaporin-1 facilitates epithelial cell migration in kidney proximal tubule. *J Am. Soc. Nephrol.* 17, 39-45, doi: 10.16811ASN.2005080846 (2006).
34. Price, G. & Tien, *J. in Biological Microarrays Vol. 671 Methods in Molecular Biology* (eds Ali Khademhosseini, Kahp-Yang Suh, & Mohammed Zourob) Ch. 17, 281-293 (Humana Press, 2011).
35. Cui, S., Verroust, P., Moestrup, S. K. & Christensen, E. I. Megalin/gp330 mediates uptake of albumin in renal proximal tubule. *American Journal of Physiology-Renal Physiology* 271, F900-F907 (1996).
36. Gekle, M. Renal proximal tubular albumin reabsorption: daily prevention of albuminuria. *Physiology* 13, 5-11 (1998).
37. Norden, A. G. et al. Urinary megalin deficiency implicates abnormal tubular endocytic function in Fanconi syndrome. *J Am. Soc. Nephrol.* 13, 125-133 (2002).
38. Miller, J. S. et al. Rapid casting of patterned vascular networks for perfusable engineered three-dimensional tissues. *Nature materials* 11, 768-774, doi:10.1038/nmat3357 (2012).
39. Wang, Y. et al. CIC-5: role in endocytosis in the proximal tubule. *American journal of physiology. Renal physiology* 289, F850-862, doi:10.1152/ajprenal.000110.2005 (2005).
40. Miller, K. & Levine, J. in *Prentice Hall Biology* Ch. 38, 987 (Prentice Hall, 2008).
41. Mescher, A. in *Junqueira's Basic Histology: Text and Atlas* 85 (McGraw-Hill Education, 2013).

Example 2

Background and Significance:

About 31 million people (10-11% of the adult population) in the United States suffers from chronic kidney disease (CKD). Moreover, every year more than 650,000 patients in the United States are treated for end stage renal disease (ESRD), which is increasing by 5% annually. Despite the urgency and prevalence of chronic and end stage renal disease, there are only two treatments available: transplantation and dialysis. While transplantation is a better treatment, the gap between the patients in need of a new kidney (>100,000) and the number of donor organs (~17,000) continues to grow ~8% per year. Dialysis, which relies the same technology invented 50 years ago, has a high risk of infection, clotting, fatal bleeding, and other complications, leading to about 25% of mortality of the dialysis patients within 12 months. The current paradigm of thrice-weekly in-center hemodialysis for 4-hour sessions also reduces the patients' life quality, and causes anemia, hypertension, depression, and need for medications (phosphate binders and anti-hypertensives). It has been hypothesized that many of these shortcomings can be significantly improved if the current intermittent therapy could be replaced by a continuous dialysis strategy, such as a wearable or implantable artificial kidney.

Some previous studies investigated creating living renal tissues, including genetically-edited animal tissues for immune-tolerant xenotransplantation, re-cell/decellularization of human kidney scaffolds, and growing kidney organoids. However, each of these prior art methods suffers from key limitations, including: (1) lack of patient-specific cells to reduce organ rejection, (2) inability to effectively place the appropriate cells within the intricate sub-structures of the nephron, and (3) absence of integrated tubules and perfusable vasculature, which combine to limit the scalability and applicability of such systems.

The goal of the study is to develop a biological device that assists renal functions (e.g., filtration, reabsorption, etc.).

The development of a fully integrated renal filtration-reabsorption device at human physiological scales requires the ability to: (1) develop stable, well-characterized renal specific cell sources for the glomerulus and proximal tubular microenvironments, (2) create glomerular compartments that promote filtration that are coupled to (3) perfusable, densely packed 3D proximal tubules embedded in ECM that promote proper cell phenotype and enable reabsorption.

Towards this objective, iPSC biology, microfluidics, and 3D bioprinting can be combined to assemble perfusable renal tissues 12 (shown in various Figures, see, e.g., FIGS. 1, 2, 19, 20, 22) with nephron-like functionality. Specifically, based on the recent advances in iPSC-derived podocytes that form foot processes on a synthetic porous membrane in microfluidic devices (Musah S., et al., *Nature Biomedical Engineering*, 1(5), pp. s41551-017 (2017)) and bioprinted perfusable PTs (described in Example 1 above) a living integrated filtration-reabsorption extracorporeal (LIFE) device 13 (FIGS. 19 and 23) that recapitulates renal physiological function in vitro at scale can be produced.

Specifically, FIG. 19 shows a schematic of the fluid flow in the proposed LIFE system. The LIFE device will mimic the physiological flow configuration, in which the plasma flows through the glomerulus and the filtrate is then perfused through the PT. Subsequently, the nutrients in the filtrate are reabsorbed by the PT and transferred to the blood stream leading back to the body. The main purpose of the LIFE device is to replace current dialysis techniques with both a cellular filter (glomerular portion) and cellular reabsorption (proximal tubule portion) components.

Part 1: Design, Manufacture, and Characterization of a 3D Glomerulus Model that Exhibits a Physiological Filtration Rate.

A physiologically functioning glomerulus model requires three key elements: (1) fully differentiated podocytes that are stabilized by the endothelium in (2) 3D perfusable channels embedded in a (3) highly permeable engineered extracellular matrix (ECM).

Based on the protocol described in Musah et al. (Musah et al., *Nature Medical Engineering*, 1, Article number: 0069: 1-12 (2017)), a directed differentiation of iPSC into podocytes within 3D bioprinted and perfusable channels will be performed, followed by seeding the endothelial cells to create glomerular capillaries.

Compared to conventional 2D membrane systems, it is anticipated that the 3D microphysiological environment will substantially enhance the cell phenotype and transporter expression. Also, a novel macroporous ECM to support the tubules and enable efficient fluid filtration and transport will be developed.

1.1: 3D Bioprinting of Vasculature Embedded within Macroporous Extracellular Matrices.

In vivo, glomerular capillaries are tortuous and tightly packed channels that are supported by the mesangium (FIG. 21A). Such architectures are difficult to directly replicate by bioprinting due to their complexity and size scale. The aim of this study is to construct a highly permeable scaffold that physically supports the glomerular capillaries (FIG. 21B). Specifically, a biocompatible and crosslinkable hydrogel-based macroporous matrix, in which the fluid coming out of the glomerular capillaries can readily flow through the interstitial space between pores will be produced. These porous matrices will be generated by either hydrogel foam casting or direct foam writing.

To create vascular channels within these macroporous matrices, a bioprint-cast-evacuate approach will be used. This method relies on first printing a thermally reversible fugitive ink (Pluronic F-127) (Wu, W., et al., *Advanced Materials*, 23(24) (2011)) in a prescribed vascular architecture, then surrounding the printed features with the porous matrix and finally removing the fugitive ink by cooling the structure to 4° C., where the ink liquefies and can be flushed away leaving behind open, interconnected cylindrical channels that can be lined with endothelium.

FIG. 21C provides a schematic illustration of the three key steps in the fabrication process.

Step (i) will include depositing a layer of the macroporous material. Examples of macroporous materials include macroporous polymers, macroporous biomaterials (such as collagen, fibrin, etc.), or macroporous structures of gelatin, chitosan, alginate, etc.

Step (ii) will include 3D printing hollow, tubular structures onto this base layer using a custom-made core-shell nozzle with an inner core of fugitive ink and an outer core of cell-adherent hydrogel. U.S. Provisional Application Ser. No. 62/431,653, entitled "3D printed core-shell filament and method of printing a core-shell filament;" U.S. Provisional Patent Application Ser. No. 62/431,723, filed Dec. 8, 2016, entitled "Core-shell nozzle for three-dimensional printing and method of use;" and U.S. Provisional Patent Application No. 62/535,557, filed Jul. 21, 2017, entitled "Methods of producing tubular multi-layered constructs," describe bioprinting methods using a multicore-shell approach, and are hereby incorporated by reference in their entirety.

Step (iii) will include casting additional macroporous matrix around the printed feature and cross-linking, seamlessly binding to the bottom layer of material. After cross-linking, the fugitive core will be removed, generating an open lumen within the macroporous matrix. We will engineer the printed hydrogel (such as gelatin-fibrinogen mixture) shell to degrade over time through the metalloproteinase process, such that ultimately the seeded podocytes will deposit basement membrane protein directly on the macroporous scaffold, forming a contiguous glomerular tissue. After degradation, the direct contact between podocytes and porous scaffold will lead to a highly permeable interface, which is crucial for recapitulating the physiological renal filtration process.

1.2: Directly Differentiate iPSCs into Podocytes in Perfused Channels

We plan to directly differentiate iPSCs into podocytes within the constructed channels. While many labs have worked toward developing mechanical filters to perform filtration in the human body, these synthetic and acellular filters usually have a limited lifetime and need to be replaced frequently due to fouling, which could limit the lifetime of an implantable mechanical kidney. In contrast, human kidneys are able to maintain high filtration efficiency (~130 liters per day) for tens of years, due to the ability for the cellular glomeruli to efficiently clear accumulated macromolecules and waste in the body. Thus, we hypothesize that making a cellular glomerular filter will maintain durability with minimal fouling on chip. However, to construct this device, there is a need to create a readily expandable and scalable source of podocytes, the key functional cell in the glomerulus. Unfortunately, podocytes isolated from adult kidneys are difficult to isolate, hard to expand, and generally do not maintain a purely glomerular phenotype.

Here, iPSC derived podocytes and endothelium will be used on chip, in which the podocytes will be directly derived in perfused channels and endothelial cells will be seeded subsequently. A directed iPSC differentiation will be performed on chip, as shown in FIG. 21B for the podocyte lineage—relying on an efficient (>90%) and chemically defined protocol developed by Musah et al. (Musah et al., *Nature Medical Engineering*, 1, Article number: 0069: 1-12 (2017)) for directing the differentiation of iPSCs into podocytes that express mature phenotype markers (Morizane, et al., *Nature biotechnology*, 33(11), p. 1193 (2015)) (FIG. 21A-B). As previously shown, the iPSC-derived podocytes form foot processes (both primary and secondary) with the endothelium in their 2D microfluidic device (FIG. 21C-D). However, the 2D sheet geometry in their original devices (versus the proposed herein 3D channel structure) limits the total surface area of the membrane leading to a low filtration rate.

The iPSC-derived intermediate mesoderm cells will be seeded directly in the printed 3D channel structure described above for directed differentiation. The differentiation efficiency will be optimized by varying the hydrogel composition, basement membrane coating, small molecule induction (FIG. 21A, stage 3), and the perfusion stress. After the matured podocytes form a confluent monolayer on the hydrogel matrix, glomerular microvascular endothelial cells (GMECs) will be subsequently seed in the lumen, so they can expand and deposit their glomerular basement membrane (GBM) directly on the podocyte layer. The final three-layer structure: podocyte interdigitating processes, GBM, and fenestrated endothelium (see FIG. 21B), will closely mimic the physiological filtration membrane in vivo.

1.3 Characterize the Glomerular Filtration Rate (GFR) and Renal Clearance of the Glomerulus Model Upon completion of our 3D printed glomerulus model (1.1-1.2 above), an assay platform to characterize its two essential renal functions, GFR and renal clearance, will be developed. In glomeruli, the GFR is directly regulated by the blood pressure. To mimic this in vivo mechanism, a microflow valve will be installed after the perfusion outlet in the system tuning the pressure drop across our biological filtration membrane (~40 mmHg or 5.3 kPa) (Johnson, Richard J., et al., Comprehensive Clinical Nephrology E-Book. Elsevier Health Sciences (2014)). In the experiment, we will tune the pressure drop and monitor the resulting GFR by measuring the real-time change in the perfusion media volume.

To test the renal clearance, fluorescently labeled compounds with different molecular weights will be flowed into our 3D glomerulus model, and their distribution over time will be measured using confocal microscopy. To quantify the renal clearance, the compound concentration difference will be compared across the filter for human serum albumin (hydrodynamic radius, $R_h$~3.5 nm), inulin ($R_h$~1.5 nm), and glucose ($R_h$~0.4 nm).

Alternative Approaches:

In certain embodiments, the full-differentiated podocytes may be coated with basement membrane proteins, such as laminin or collagen IV, prior to introducing the (GMEC) endothelial cells. Alternatively, mesangial-like cells can be included into the core-shell printing ink to help facilitate basement membrane deposition and cell-cell interactions that support endothelial adhesion.

Due to the proposed sequential lining strategy, it may be possible that both cells will have the same polarization toward the lumen wall, resulting in two separate basement membrane layers at the podocyte-scaffold and podocyte-endothelium interfaces. In doing this, it may be possible to reorient the podocyte polarization, and thus promote basement membrane deposition at the podocyte-endothelium interface to mimic the in vivo configuration.

Part 2: Design, Manufacturing, and Characterization of a 3D Vascularized Proximal Tubule (PT) Model that Exhibits a Physiological Reabsorption Rate.

The renal vasculature is essential for sustained renal reabsorption. Therefore, bioprinting, which enables the rapid and programmable fabrication of highly complex architectures, will be used to construct a double-layered tubule network, creating a vascularized PT model. Furthermore, to achieve the physiological reabsorption level, the multiplex printing method will be used to scale up the surface area of the proximal tubules.

The renal vasculature plays an essential role in kidney function including sustained reabsorption, immune cell recruitment, blood pressure regulation, and hormone secretion. The aim of this study is to build vascular conduits near PTs on perfusable chips. Channels will be embedded within a highly permeable hydrogel, and perfused independently. In addition, we will line the vascular conduits and PTs with GMECs, and proximal tubular epithelial cells (PTECs), respectively. To validate the reabsorption function of our vascularized PT, the water transport and the trafficking of various compounds including human serum albumin (HSA), glucose, and inulin (as negative control) between the PT and vasculature will be monitored.

2.1: 3D Bioprinting Vascularized Proximal Tubules Embedded in Hydrogel.

Vascular conduits near proximal tubules will be printed as described in Example 1 above (FIGS. 5A-C). Specifically, a multi-layered print strategy will be used to stack two independently addressable tubular networks, vertically separated by a thin hydrogel layer. The vertical stacking geometry allows maximum contact area between the PT and vascular networks. Conditions will be identified that minimize the separation between these two networks to allow for efficient fluid and molecule exchange.

The four main steps of the fabrication are illustrated in FIG. 22C. First, a layer of gelatin-fibrinogen (Gelbrin) hydrogel will be deposited on the substrate as the base layer. We will print the PT structures (blue tubules in FIG. 22C) on the base layer using a fugitive ink that will eventually be evacuated. After printing, a small amount of Gelbrin will be cast around the printed features creating another flat printing surface. We will then print the vascular conduits (red tubules in FIG. 22C) on this new surface, and cast Gelbrin over them. Finally, the open lumen of the PT and vasculature are created by evacuating the fugitive ink. We will seed proximal tubular epithelial cells (PTECs) and glomerular microvascular endothelial cells (GMECs) into the PT and vascular channels 5, 7 (see, e.g., FIGS. 2, 22), respectively. Here, we use Gelbrin as the matrix, since it is a cell-adhering ECM, and promotes the expression of many relevant transporters of PTECs, as shown in our previous work.

2.2: Characterization of the Reabsorption Rate of the 3D Vascularized PT Model.

The reabsorptive function of our 3D PT model will be assessed at both the cellular and macroscopic levels. At the cellular level, a systematic analysis will be performed using immunochemistry, polymerase chain reaction (PCR), and flow cytometry to characterize cell morphology, protein expression, and cell surface markers. For example, the expression level of various transporters of PTECs, such as $Na^+/K^+$ ATPase, AQP1, megalin, and SGLT2 will be measured. Several epithelial markers (LTL, ZOI, K-Cadherin and E-Cadherin), the primary cilia, microvilli, and the basement membrane protein deposition (Laminin and Col IV) will also be investigated. Similar to these measurements for PTECs, the function and phenotype of the endothelium will be characterized by investigating several markers of phenotypically healthy endothelial cells including CD-31, vWF, and VE-Cadherin.

In addition to the typical biomarker characterization, which offers the basic validation and understanding of the cellular transport function, the vascularized PT model described herein also allows us to perform the physiological reabsorption test at a macroscopic scale. To conduct this assay, we plan to develop an experimental platform, in which we will administer fluorescently labeled glucose, human serum albumin (HSA), urea, inulin, or other drugs through either the PT or vascular channel, and then subsequently monitor the concentration of those compounds in the perfusate for both channels. Specifically, a live cell imaging with a confocal microscope will be performed to monitor the movement of those molecules. Meanwhile, the perfusate from both channels' outlets will be collected using a custom-made fraction collector that can fit in a microscope incubator. To quantify the reabsorption performance of our vascularized PT model, the measured concentration of these compounds will be compared. For instance, in vivo the glucose and HSA are mostly reabsorbed toward the end of PT, and thus their concentrations in the vasculature are much higher than that in the PT. In contrast, the majority of inulin and urea should remain in the PT at all times as the tight cellular barrier blocks them (Johnson, Richard J., et al., Comprehensive Clinical Nephrology E-Book. Elsevier Health Sciences (2014)).

Part 3: Design, Manufacture, and Characterization of a Living Integrated Filtration-Reabsorption Extracorporeal (LIFE) Device, which Combines the Developed 3D Glomerulus and Proximal Models.

A microfluidic platform, LIFE, integrating the 3D glomerulus and proximal tubule models will be created. Further, a study will be designed to determine whether the LIFE system would mimic the physiological flow configuration, in which the plasma flows through the glomerulus and then PT. Also, the study is designed to determine whether the nutrients in the plasma are reabsorbed by the PT and transferred to the blood stream that will again flow through the glomerulus.

The 3D glomerulus (filtration) and vascularized PT (reabsorption) models are the two essential components for building our proposed LIFE device. Therefore, in Parts 1 and 2 of this Example 2 it was proposed to perform substantial characterizations of both sub-systems. This study will focus on integrating these two critical components using a custom-made microfluidic platform, and characterizing various renal functions of this LIFE system.

3.1: LIFE Device Design and Fabrication.

Upon completion of studies described in parts 1 and 2 above, a microfluidic platform that integrates the 3D glomerulus and proximal tubule models will be created to produce the LIFE device.

As depicted in FIG. 23, the LIFE system will mimic the physiological flow configuration of the nephron, in which the plasma flows through the glomerulus, then PT, and into a collecting duct. Within the PT nutrients in the plasma are reabsorbed by the PT and transferred to the blood stream that will again flow through the glomerulus, then the non-reabsorbed and compounds and fluid will be collected from the outlet of the device.

Specifically, FIG. 23 shows a diagram illustrating the flow of the blood (perfused media) in the LIFE device. The main stream of the perfusate is driven by the pump flowing through the each part of the device in the following order: afferent arteriole, glomerular capillary, Bowman's capsule compartment, proximal tubule, and then outlet to collecting duct. In the glomerular capillary section, the internal hydrostatic pressure may be regulated by tuning the micro-flow valve, so that 20% of the perfusate is filtered, as in vivo. The rest 80% of the perfusate exits through the efferent arteriole and then flows into the vasculature next to the proximal tubule.

3.2: LIFE Device Characterization of Renal Functions and Stability.

To characterize renal functions and stability of LIFE device, the concentration of HSA, glucose, inulin, and urea in the reservoir media (FIG. 23) that is cyclically perfused through the device will be monitored. In the human body, the HSA and glucose are concentrated, while urea and inulin should be actively removed from the plasma. Therefore, it is expected to observe a qualitatively similar trend in the LIFE device. Also, the concentration and removal of the specific molecular entities will be confirmed by measuring the concentration of those compounds by analyzing the fluid waste from the device outlet. These two complementary measurements are analogous to sampling blood or urine tests and will offer insights into the efficiency and specificity of the LIFE device over time.

Finally, evaluation of the stability of the LIFE device will be performed.

Maintaining the primary cell linage and phenotype in conventional culture or even organ-on-chip systems over a long duration remains an open challenge. Moreover, in both in vivo and our in vitro glomeruli, podocytes are terminally differentiated, and thus do not divide or repair. Therefore, the long-term cell behavior and renal functions in the LIFE device will be observed for at least one month. This timespan is about 3-5 times longer than the typical Acute Kidney Injury (AKI) duration and can be critical for evaluating the applications toward extracorporeal devices. Additionally, we plan to simulate hyper- and hypo-perfusion states by modulating the flow rates within the device; this will allow us to derive an optimal operating range for extending the device lifetime.

In certain embodiments, if it is observed that the waste liquid coming out of the PT still contains a considerable amount of protein and glucose, the LIFE device will be capable to direct a fraction of the fluid back to the reservoir to conserve the important media components.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, are intended to define the spirit and scope of this invention.

The invention claimed is:

1. An apparatus for use in connection with organ replacement or organ assist therapy in a patient, comprising:
   (a) a housing defining an interior cavity;
   (b) a programmable mammalian tissue construct disposed in the housing and comprising:
      (i) one or more tissue patterns, each tissue pattern comprising a plurality of viable cells; and
      (ii) a network of channels interpenetrating the one or more tissue patterns, the interpenetrating channels being 3D-printed with the tissue pattern, and having configurations with highly controlled size, curvature, and location, and an addressable open lumen that can be maintained longitudinally, wherein any space between the printed network of channels is occupied with one of more tissue patterns,
wherein the network of interpenetrating channels comprises a first channel for communication of arterial blood supply to the programmable mammalian tissue construct, a second channel for communication of venous blood away from the programmable mammalian tissue construct and a third channel for communication of material extracted by the programmable mammalian tissue construct from the arterial blood supply,
wherein the programmable mammalian tissue construct is at least partially surrounded by a biocompatible material, and
wherein in use the programmable mammalian tissue construct has organ-like function selected from one or more of: filtration, reabsorption, metabolism, concentrating, modifying or immune modulating of at least one essential component or cell product of the patient's bodily fluid excreted due to a disease or dysfunction of the patient's organ, and transfer of the at least one essential component or cell product back to the patient's bodily fluid; or
production, secretion, and transfer of at least one of the same or another essential component or cell product into the patient's bodily fluid; and
(c) a patient interface device comprising an extracorporeal circuit for communication of fluids between the patient and the programmable mammalian tissue construct disposed in the housing, and wherein the housing is occupied with the extracorporeal circuit.

2. The apparatus of claim 1, wherein the programmable mammalian tissue construct further comprises an extracellular matrix composition at least partially surrounding the one or more tissue patterns and the network of vascular channels.

3. The apparatus of claim 1, wherein the viable cells are patient-derived cells.

4. The apparatus of claim 1, wherein the viable cells comprise at least one of renal proximal tubule cells, loop of Henle cells, renal distal tubule cells, collecting duct cells, mesangial cells, renal microvascular cells, renal cell progenitors, pluri or multipotent stem cells, other endothelial lineage cells, endothelial cells, fenestrated glomerular endothelial cells, or iPSCs-derived patient-specific cell lines.

5. The apparatus of claim 4, wherein the programmable mammalian tissue construct further comprises a plurality of capillaries of glomerulus or other structural elements of the kidney.

6. The apparatus of claim 1, wherein the programmable mammalian tissue construct is selected from the group consisting of viable cells, organoids, embryoid bodies, endothelial sprouts, autologous tissue, allogeneic tissue, xenogeneic tissue, and a three-dimensional-printed tissue constructs.

7. The apparatus of claim 1, wherein the programmable mammalian tissue construct comprises embedded vasculature.

8. The apparatus of claim 1, wherein the programmable mammalian tissue construct is a tubular tissue construct with embedded vasculature.

9. The apparatus of claim 8, wherein the programmable mammalian tubular tissue construct is a nephron, intestine, milk duct, sweat gland, colon, esophagus, stomach, eustachian tube, airway epithelium, epididymis, seminiferous tubules, urethra, liver bile duct, pancreatic duct, common bile duct, cerebro-spinal ventricles and aquaducts, parotid glands, oral mucosa, fallopian tube, vas deferens, or lymph.

10. The apparatus of claim 8, wherein the programmable mammalian tubular tissue construct is a human proximal tubule with embedded vasculature, wherein the tubular programmable mammalian tissue construct comprises perfusable renal tissues with a nephron-like functionality.

11. The apparatus of claim 8, wherein the programmable mammalian tissue construct is an epithelial tissue construct.

12. The apparatus of claim 1, wherein the programmable mammalian tissue construct comprises an interpenetrating vascular network integrated with a cellular glomerular filtration unit and the patient interface device.

13. The apparatus of claim 12, wherein the cellular glomerular filtration unit comprises at least one of iPSC-derived intermediate mesoderm cells, or iPSC-derived podocytes.

14. The apparatus of claim 1, wherein the extracorporeal circuit comprises:
a first tube configured for communication with an organ of the patient and allowing the flow of patient's bodily fluid from the patient's organ through the first tube to the programmable mammalian tissue construct; and
a second tube configured for communication with a blood vessel or a bioduct of the patient and allowing the flow of patient's bodily fluids from the programmable mammalian tissue construct through the second tube to the patient.

15. The apparatus of claim 1, wherein the apparatus comprises a porous barrier between the programmable mammalian tissue construct and the bodily fluid present when in use.

16. The apparatus of claim 15, wherein the porous barrier is a filter that produces an ultrafiltrate.

17. The apparatus of claim 15, wherein the porous barrier is a hemofilter.

18. The apparatus of claim 15, wherein the porous barrier is a cellular filter.

19. The apparatus of claim 1, wherein the apparatus is adapted to remove the immunogens from the bodily fluids before returning a filtrate to the patient's bodily fluids.

20. The apparatus of claim 1, further comprising at least one pump to simulate patient's blood pressure and flow rates.

21. The apparatus of claim 1, wherein the apparatus is configured so that the programmable mammalian tissue construct can be exposed to one or more biological agents, a biological agent gradient, a pressure, and/or an oxygen tension gradient.

22. The apparatus of claim 1, wherein the housing is configured and dimensioned to be carried or worn by the patient.

23. The apparatus of claim 1, wherein the apparatus is configured to be implanted into the patient's body.

24. The apparatus of claim 1, wherein the patient interface comprises an inlet manifold on an inlet side of the housing for distributing the bodily fluid to an inlet of the network of interpenetrating channels and an outlet manifold on the outlet side of the housing for collecting the bodily fluid from a plurality of outlet ports of the network of interpenetrating channels.

25. The apparatus of claim 24, wherein the outlet manifold comprises at least three sections, a first section coupled with the first channel of the network of interpenetrating channels, a second section coupled with the second channel of the network of interpenetrating channels, and a third section coupled with the third channel of the network of interpenetrating channels.

26. The apparatus of claim 1, wherein the biocompatible material is in a form of a liquid, gel, paste, or a matrix.

27. The apparatus of claim 1, wherein the biocompatible material is an extracellular matrix material.

28. The apparatus of claim 1, wherein the biocompatible material comprises one or more of gelatin, fibrin, matrigel, collagen, elastin, alginate, PEG hydrogels, hyaluronic acid, and gelatin methacrylate.

29. The apparatus of claim 1, wherein the interpenetrating channels comprise a plurality of proximal epithelial tubules and a plurality of endothelial tubules;

wherein the proximal epithelial and endothelial tubules have an addressable open lumen that can be maintained longitudinally;

wherein the epithelial tubules and endothelial tubules are in a close proximity to each other, wherein the proximal epithelial tubules are adapted for and capable of resorption of at least one essential component or cell product of the patient's bodily fluid, wherein the at least one essential component or cell product is selected from small molecules, ions, water, and proteins of metabolism, and is excreted from the patient's bodily fluid due to a disease or dysfunction of the patient's organ; and transfer of the resorbed at least one essential component or cell product back to the patient's bodily fluid; and wherein the proximal epithelial tubules and the endothelial tubules are capable of production, secretion, and transfer of at least one of the same or another essential component or cell product into the patient's bodily fluid.

\* \* \* \* \*